United States Patent [19]
Abrams et al.

[11] Patent Number: 5,201,931
[45] Date of Patent: Apr. 13, 1993

[54] ABSCISIC ACID-RELATED PLANT GROWTH REGULATORS - GERMINATION PROMOTERS

[75] Inventors: Suzanne R. Abrams; Lawrence V. Gusta, both of Saskatoon, Canada

[73] Assignee: Her Majesty the Queen in right of Canada, as represented by the National Research Council of Canada, Ottawa, Canada

[21] Appl. No.: 444,704

[22] Filed: Dec. 1, 1989

Related U.S. Application Data

[63] Continuation-in-part of Ser. No. 280,102, Dec. 1, 1988, abandoned.

[51] Int. Cl.$^5$ .................... A01N 31/04; A01N 43/08; A01N 35/04
[52] U.S. Cl. .................... 504/291; 504/193; 504/288; 504/320; 504/348; 504/313; 504/326; 504/194; 504/201; 504/206
[58] Field of Search .................... 71/65, 77, 122, 123

[56] References Cited

U.S. PATENT DOCUMENTS 4,581,057 4/1986 Noodén .................... 71/28

OTHER PUBLICATIONS

Oritani et al., "Synthesis and Biological Activity etc. . . " Agric. Biol. Chem. 46(3) 817–818, 1982.
Davies et al. "Carotenoids and Related Compounds etc. . . " J. Chem. Soc., Perkin Translation I, 1984, pp. 2147–2157.
Singh et al., "Effect of Temperatures and Concentrations etc." Chem. Abstr. 94:9904y, 1980.
Nickell, "Plant Growth Regulants", Springer-Verlag Berlin Heidelberg, New York, 1982, p. 5.
Singh et al, Trop. Grain Legume Bull., pp. 43–45 (1980).
Tamura et al., Agric. Biol. Chem. 33, 296 (1969).
Young et al., J. Amer. Chem. Soc. 66, 520 (1944).
Widmer et al., Helv. Chim. Acta. 65, 1958 (1982).
D. C. Walton in Abscisic Acid F.T. Addicott, Ed. Paraeger Press, New York (1983), Chap. 4.

Primary Examiner—Richard L. Raymond
Assistant Examiner—Brian Bembenick
Attorney, Agent, or Firm—Oblon, Spivak, McClelland, Maier & Neustadt

[57] ABSTRACT

Composition for enhancing germination and growth of plants which comprises an effective amount of at least one abscisic acid-related compound having the following formula (I):

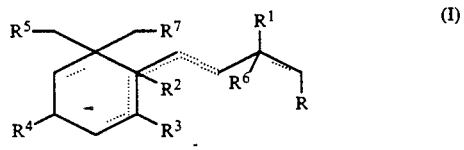

6 Claims, 12 Drawing Sheets

Figure 1 "Root Germination at 0.01 μM"

Figure 2 "Emergence of Katepwa Wheat at 10 C" Imbibed for 4 Hours in Compound (VI)

The Effects of PBI-10 and GA on Germination of Baron Kentucky Bluegrass

Figure 4 "Emergence of Tobin Canola at 10C" Imbibed for 8 hours with Compound 10

"Emergence of Westar at 10C" Imbibed for 8 hours in Compound 10

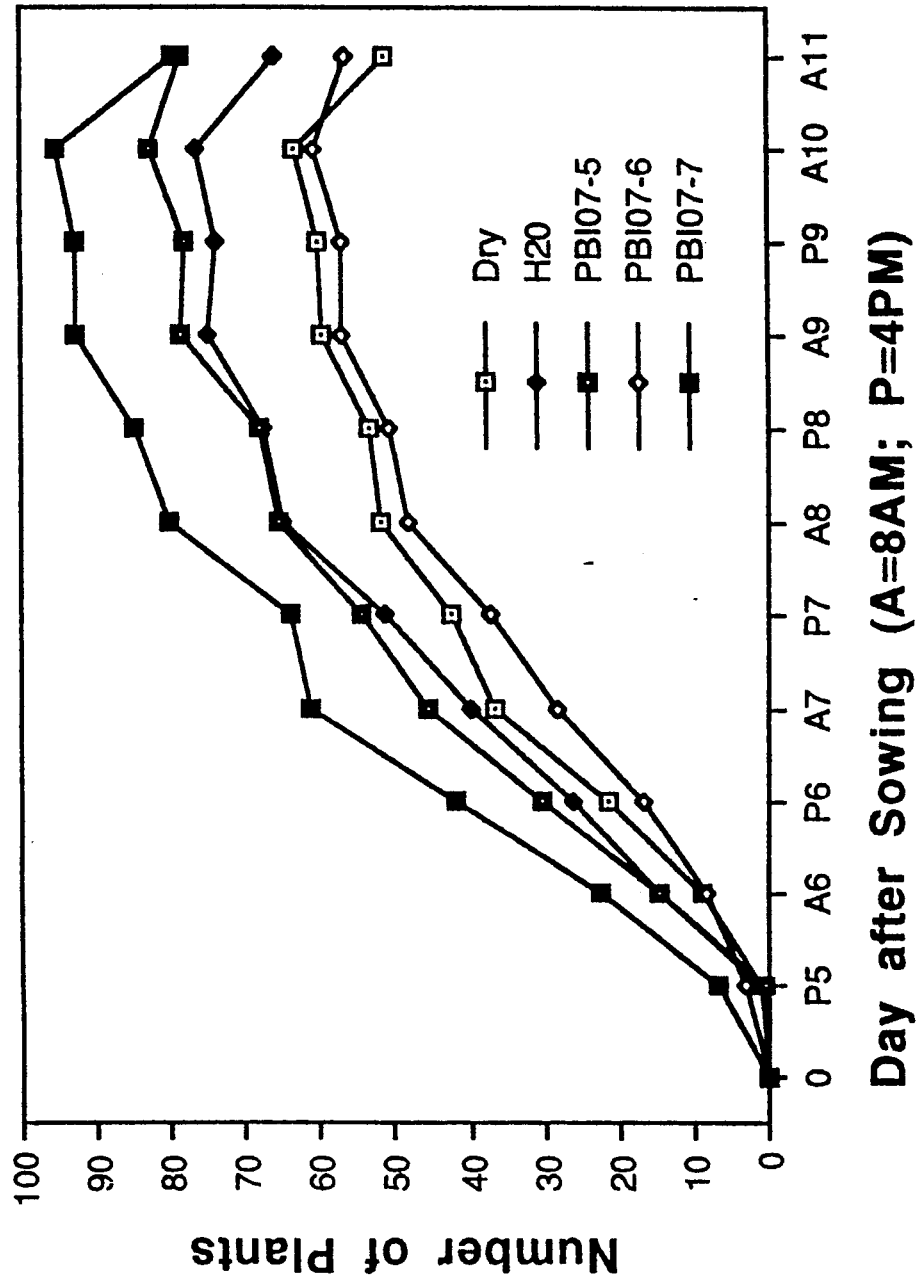
Figure 6 "Emergence of 'Westar' Canola: PBI07"
Number of Plants / 2m Row

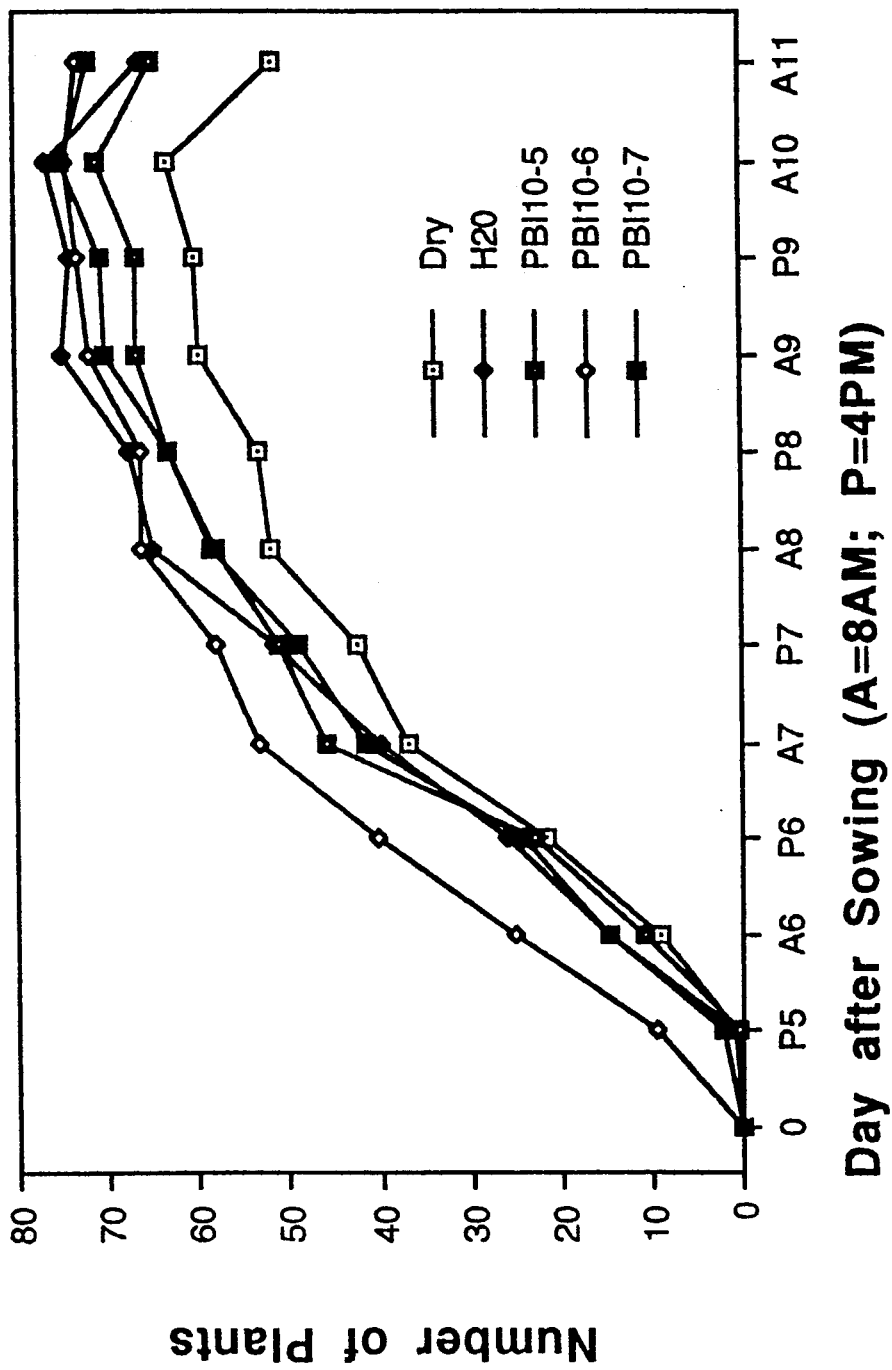
Figure 7 "Emergence of 'Westar' Canola: PBI10" Number of Plants /2m Row

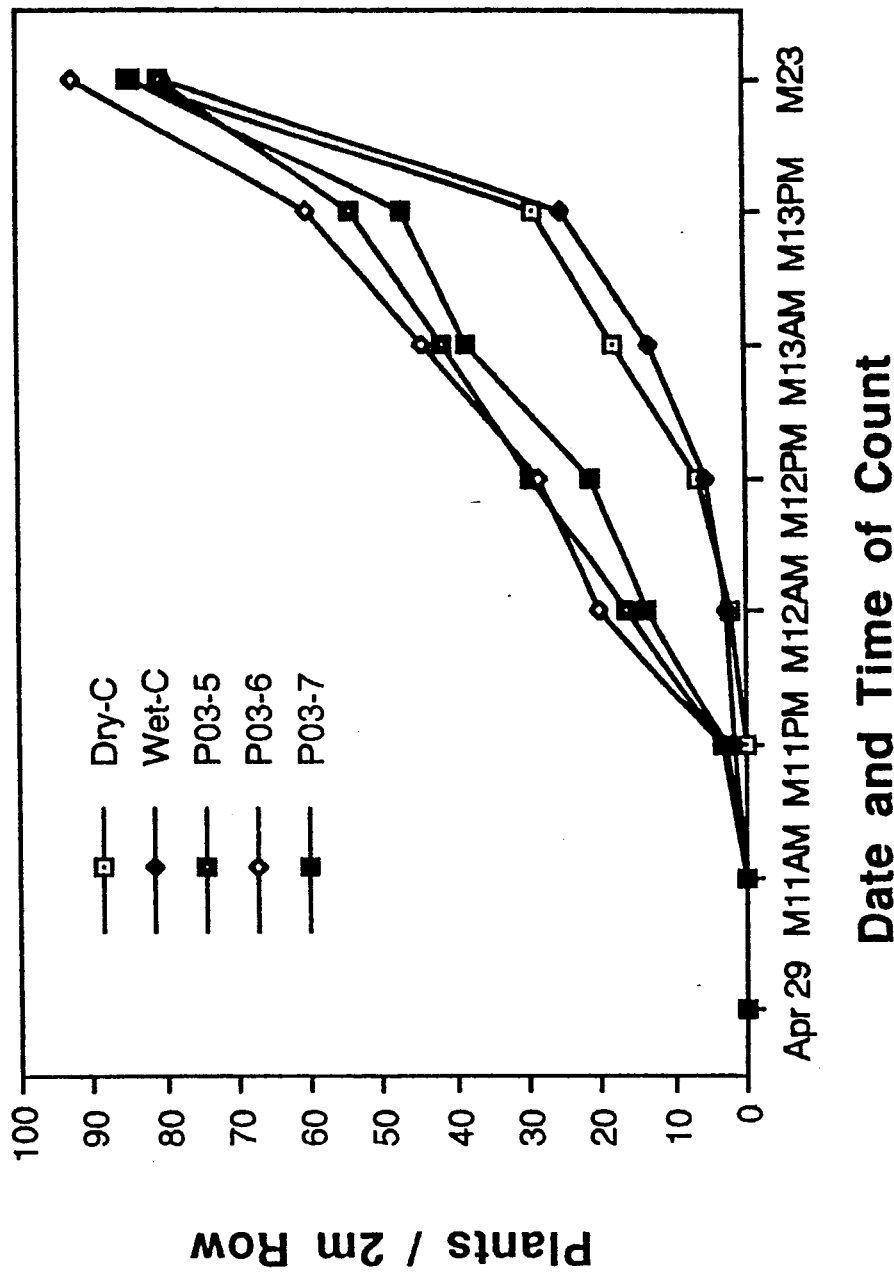
Figure 8 "Emergence of 'Katepwa': Watrous" Dry and Water Controls vs PBI03

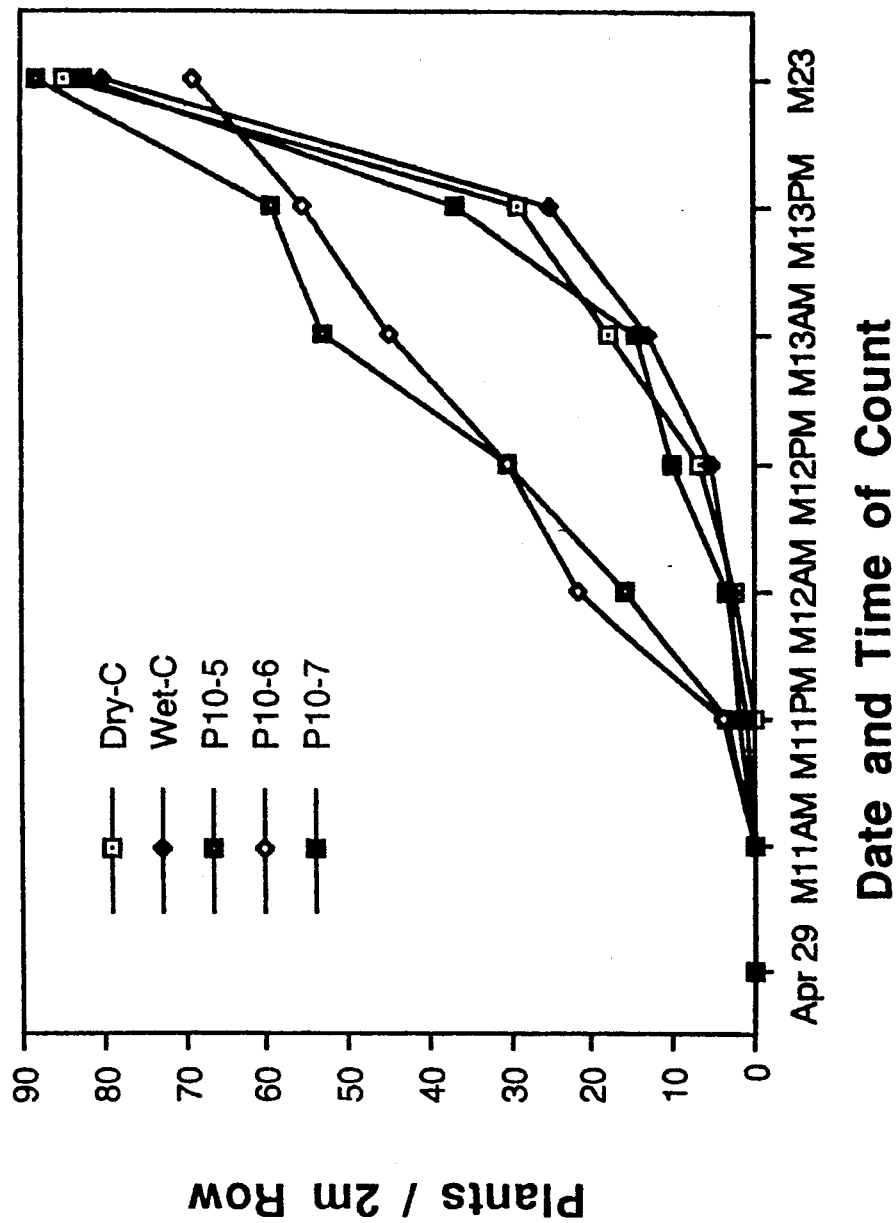
Figure 9 "Emergence of 'Katepwa': Watrous" Dry and Water Controls vs PBI10

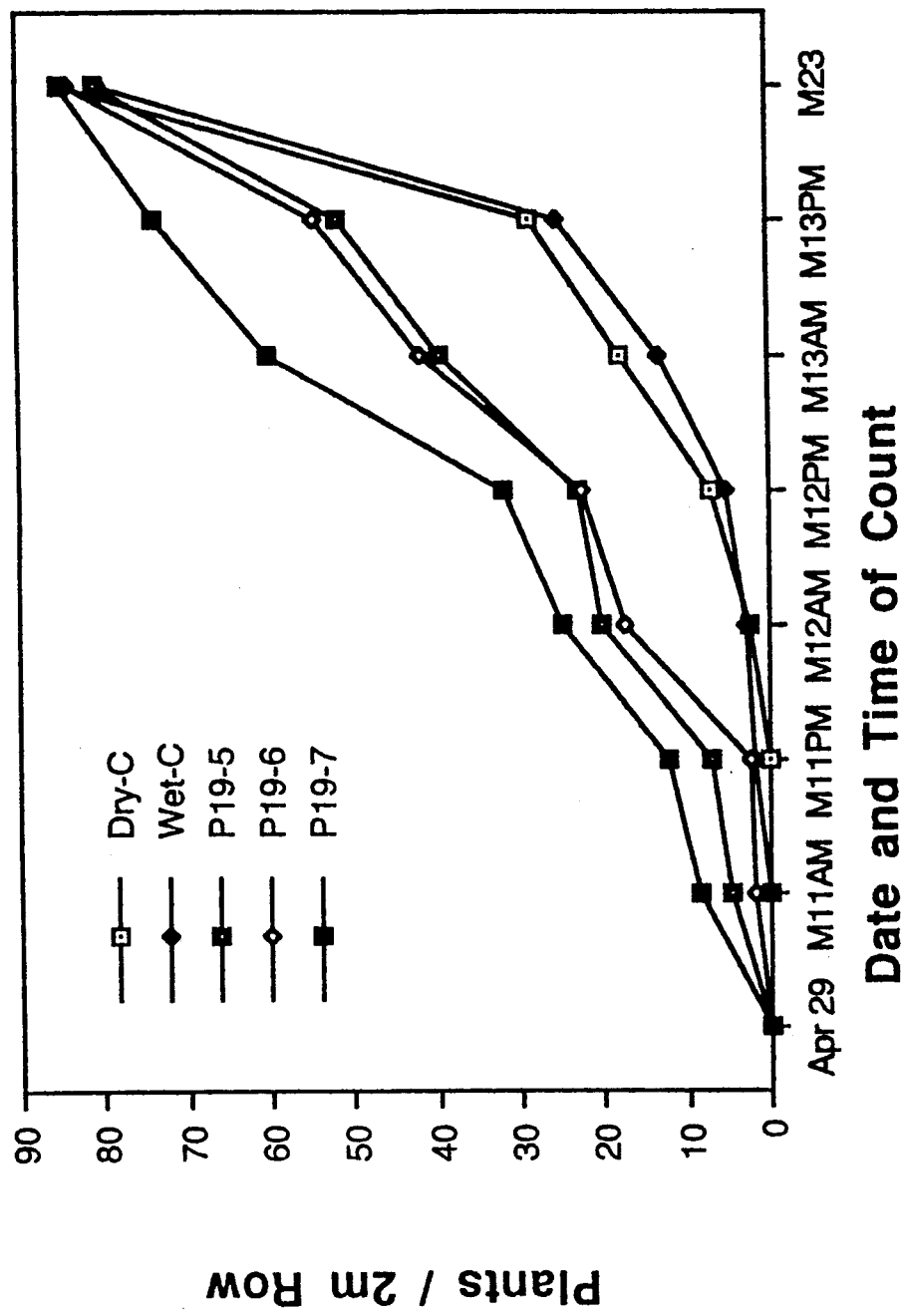
Figure 10 "Emergence of 'Katepwa': Watrous" Dry and Water Controls vs PBI19

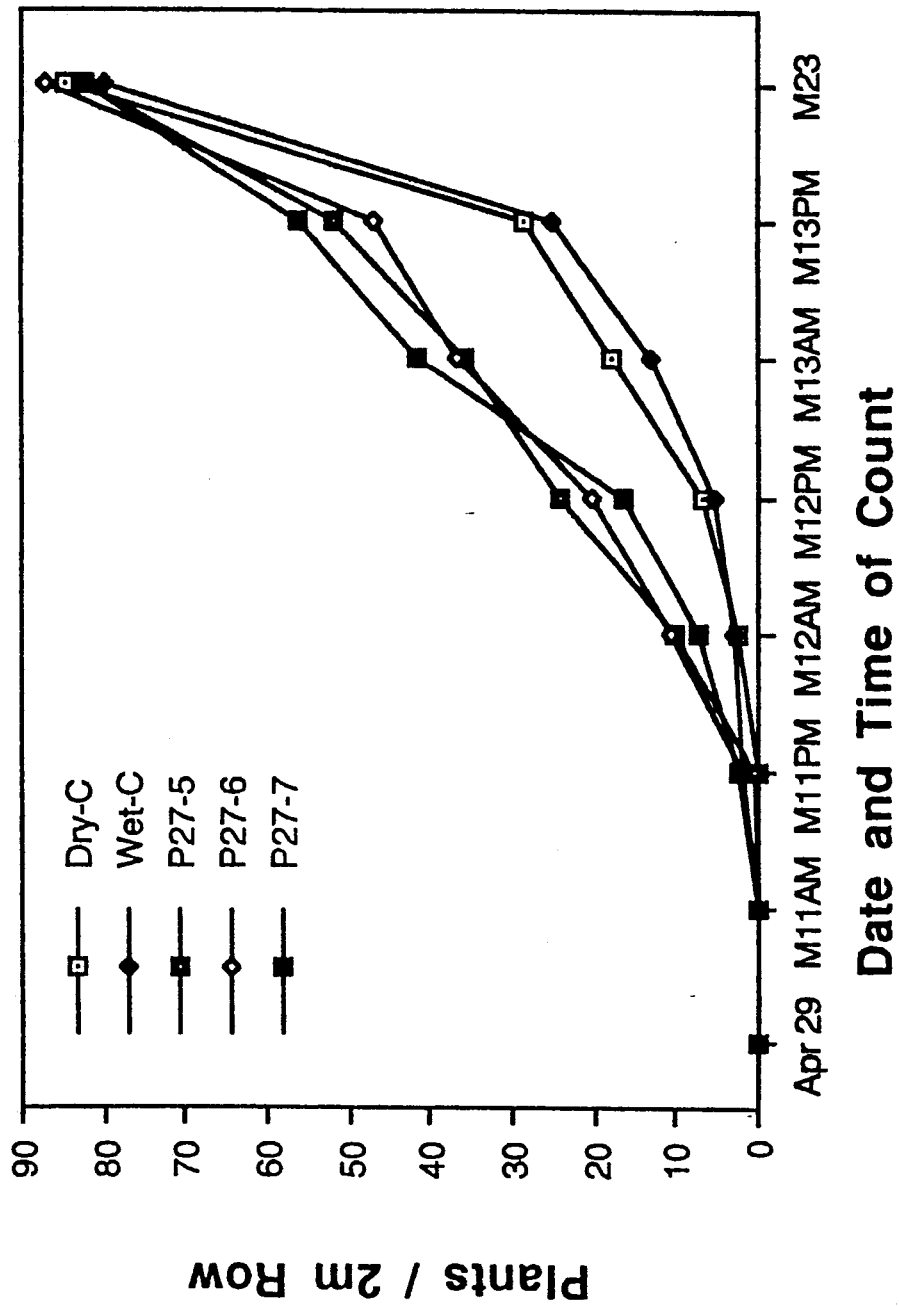
Figure 11 "Emergence of 'Katepwa': Watrous" Dry and Water Controls vs PBI27

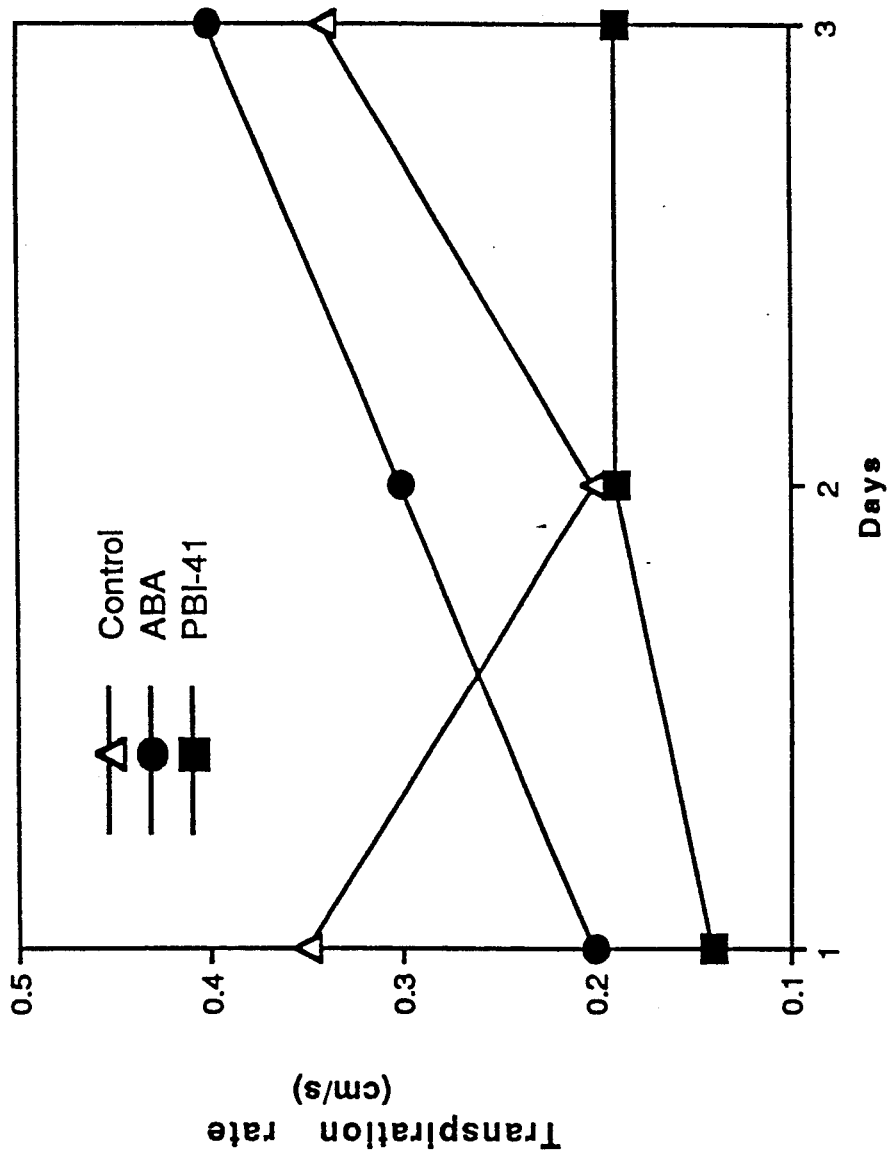
Figure 12 Transpiration Rates of Tomato Leaves 3 Consecutive Days after Soil Drench with ABA and PBI-41

ABSCISIC ACID-RELATED PLANT GROWTH REGULATORS - GERMINATION PROMOTERS

This patent application is a continuation-in-part of co-pending patent application Ser. No. 280,102 filed Dec. 1, 1988 (abandoned).

FIELD OF THE INVENTION

The invention relates to novel abscisic acid derivatives used as germination and growth promoters in plants. The present invention also relates to the use of various abscisic acid derivatives in agricultural compositions generally useful as effective germination and growth promoters for plants. The compositions are also useful for promoting plant emergence and development, the closure of plant stomata as well as increasing freezing resistance of plants and plant cells.

BACKGROUND OF THE INVENTION

Abscisic acid (ABA) is a naturally occurring substance which is known to provoke retardation or inhibition of growth in plants. The response of a plant to abscisic acid may be brief or prolonged. As mentioned at p. 526 of Abscisic acid, Addicott, ed., it may either be a simple, temporary suspension of growth, or it may modify the morphological pattern of growth.

Abscisic acid is a hormone found in all higher plants. Because of the interesting growth properties that were attributed to abscisic acid, extensive research was conducted to find suitable derivatives that could possibly possess the same or superior activities when compared to the natural plant growth regulator.

The ability of abscisic acid to arrest growth of woody shoots and to contribute to the dormancy of apical buds was detected for the first time by Eagles and Wareing in 1963, Nature 199, 874–876. Furthermore, Milborrow demonstrated in 1974 (1974, Rev. Plant Physiol. 25;259–307) that abscisic acid had an inhibiting effect on the germination of intact seeds and isolated embryos. In fact, one standard bioassay for abscisic acid utilizes the germination of wheat embryos, which is affected by concentration of suitable strength.

Six-membered carbocyclic substituted 1,3-butadiene compounds, such as 1-hydroxy-2,6,6-trimethyl-4-oxo-2-cyclohexene-1-penta-2,4-dienoic acid methyl ester have been prepared and described in U.S. Pat. No. 3,576,839. These compounds have been used in pre-emergent herbicidal applications to delay the germination of seeds and in post-emergent applications to defoliate and to effect leaf senescence.

In 1969, Saburo Tamura and Minoru Nagao prepared analogs of abscisic acid and demonstrated that these compounds were useful as growth inhibitors. It was demonstrated that the most active derivatives prepared by Tamura and Nagao possessed a growth inhibitory activity that was comparable or superior to that of abscisic acid. It was also discovered that these compounds significantly counteracted the action of gibberellin $A_3$. In 1981, two other Japanese scientists, Takayuki Oritani and Kyohei Yamashita published another series of results concerning derivatives of abscisic acid, mentioning that these compounds possessed strong growth inhibitory activities on plants that were comparable to those of abscisic acid (Agric. Biol. Chem 46 (3), 817–818 (1982)). The compounds synthesized by these two groups of scientists all had in common the carbon skeleton of abscisic acid.

In 1986, U.S. Pat. No. 4,581,057 issued to Nooden demonstrated a further series of abscisic acid derivatives that could this time be used to enhance the absorption of nutrients by plants. The discovery was important in that it provided a tool that could be used for enhancing the rate of absorption of fertilizers into the plants. It therefore had the implication of reducing the amount of fertilizers that had to be used. The derivatives prepared by Nooden in U.S.Pat. No. 4,581,057 could be used "to obtain the desired enhancement in translocation of nutrients to the reproductive tissues and other plant parts".

Therefore, since abscisic acid was first isolated by Ohkuma et al. in 1963, a large number of derivatives of that compound have been prepared and have been used for inhibiting the growth of plants.

The use of germination and growth promoters in agriculture, forestry, horticulture and malting is a widely developed practice. Growth promoters are products that shorten the time necessary for a crop to mature and thus permit greater security of harvest in short-season climates such as are found in Canada and Northern Europe. However, various problems are associated with the use of these products. In most instances, these products are expensive and must be used in very large amounts thereby causing important environmental problems. Also, problems with secondary growth and yield decrease have been noted.

Therefore, it would be highly desirable to produce and develop germination and growth promoting agents that could be used efficiently in small concentrations.

The freezing tolerance of tissue cultures can be enhanced by treating cultures with abscisic acid. For example, bromegrass cell suspension cultures treated with 75 $\mu$M ABA for 7 days can withstand freezing to $-40°$ C. (Reaney and Gusta 1987, Plant Physiol., 83:423). Results on whole plants are conflicting in that ABA can increase, decrease or have no effect on freezing tolerance. No practical application of ABA or ABA analogs for enhancing freezing tolerance of plants has been reported.

ABA at concentrations as low as $10^{-8}$M acts as an antitranspirant in partially closing stomata (N. Kondo, I. Maruta and K. Sugahara, 1980, Plant. Cell. Physiol., 21:817). Stomata may remain partially closed for as long as 4 days after treatment with $10^{-4}$M ABA and an acetylenic ABA aldehyde analog (H. Schaudolf, 1987, J. Plant Physiol., 131:433). This analog decreases water use in *Helianthus annuus, Triticum aestivum* and *Lycopersicon esculentum* while maintaining yield.

Over 80 percent of transplants (*Capsicum annuum* plants dipped into a solution of ABA prior to planting in dry soil survived while less than 60 percent of control plants survived (G. A. Berkowitz and J. Rabin, 1988, Plant Physiol. 86:344). Furthermore, the treated plants had a 30 percent higher yield.

However, the use of ABa in freezing resistance and antritranspiration experiments on plants presents serious drawbacks. Firstly, abscisic acid is very expensive to product commercially and secondly, the desired effect is only observed for short periods of time because ABA, a naturally occurring hormone, is rapidly degraded by microorganisms found on the plants or by the plants themselves.

SUMMARY OF THE INVENTION

In accordance with the present invention, it has been unexpectedly found that some compounds related in chemical structure to abscisic acid are useful as growth regulators which when applied to seeds promote the germination, emergence, and development of crop plants. These compounds are also useful to promote the closure of plant stomata and to confer chilling and freezing resistance to plants and plant tissues.

In general terms, the present invention first relates to a composition for enhancing germination and growth of plants which comprises an effective amount of at least one abscisic acid-related compound having the following formula (I):

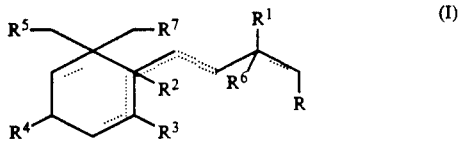

wherein

R may be carboxyl, aldehyde, hydroxy, hydroxyloweralkyl, alkoxyloweralkyl, loweralkoxycarbonyl, loweracyloxyloweralkyl, acetylloweralkyl, loweralkanoyl, loweralkylamino, diloweralkylamino, loweralkoxy, loweracyloxy, loweralkylthio, loweralkyl sulphonyl, loweralkyl sulphinyl, amino, carbonyl, halogen, thio, phosphate, sulfoxide, sulfone or deuterium;

$R^1$ may be hydrogen, oxo, hydroxyloweralkyl, loweralkoxy, halogen, thio, sulfoxide, sulfone, phosphate or deuterium;

$R^2$ may be hydrogen, oxo, hydroxy, halogen, thio, phosphate, sulfoxide, sulfone or deuterium;

$R^3$ may be carboxyl, aldehyde, loweralkyl, hydroxyloweralkyl, alkoxyloweralkyl, loweralkoxycarbonyl, loweracyloxyloweralkyl, acetylloweralkyl, loweralkanoyl, loweralkylamino, diloweralkylamino, loweralkoxy, loweracyloxy, loweralkylthio, loweralkyl sulphonyl, loweralkyl sulphinyl, or carbonyl;

and when $R^2$ is oxo or thio, $R^2$ may be linked to both $C_1$ and $C_2$ carbon atoms to form an epoxy or a thioepoxy ring;

$R^4$ may be hydrogen, oxo, halogen, thio, phosphate, sulfoxide, sulfone, deuterium, hydroxy, loweralkylsiloxane, carboxyl, aldehyde, hydroxyloweralkyl, alkoxyloweralkyl, loweralkoxycarbonyl, loweracyloxyloweralkyl, acetylloweralkyl, loweralkanoyl, loweralkylamino, diloweralkylamino, loweralkoxy, loweracyloxy, loweralkylthio, loweralkyl sulphonyl, loweralkyl sulphinyl, amino, carboxyl, cycloalakyl or cycloalkoxy having from 4 to 6 carbon atoms which is optionally substituted by loweralkyl, halogen, oxygen, hydroxy or loweralkoxy;

$R^5$ may be carboxyl, hydroxy, aldehyde,; hydroxyloweralkyl, alkoxyloweralkyl, loweralkoxycarbonyl, loweracyloxyloweralkyl, acetylloweralkyl, acetylloweralkyl, loweralkanoyl, loweralkylamino, diloweralkylamino, loweralkoxy, loweracyloxy, loweralkylthio, loweralkyl sulphonyl, loweralkyl sulphinyl, amino, carbonyl, halogen, hydroxy, oxo, thio, phosphate, sulfoxide, sulfone or deuterium, and when $R^5$ is oxo, it may be linked to the carbon atom bearing $R^3$;

$R^6$ may be hydrogen, oxo, hydroxyloweralkyl, loweralkoxy, halogen, thio, sulfoxide, sulfone, phosphate or deuterium;

$R^7$ may be carboxyl, hydroxy, aldehyde, hydroxyloweralkyl, alkoxyloweralkyl, loweralkoxycarbonyl, loweracyloxyloweralkyl, acetylloweralkyl, acetylloweralkyl, loweralkanoyl, loweralkylamino, diloweralkylamino, loweralkoxy, loweracyloxy, loweralkylthio, loweralkyl sulphonyl, loweralkyl sulphinyl, amino, carbonyl, halogen, hydrogen, oxo, thio, phosphate, sulfoxide, sulfone or deuterium, and when $R^7$ is oxo, it may be linked to the carbon atom bearing $R^3$; and wherein the dotted lines may each represent a single bond and the double dotted line represents either a double bond or a triple bond, $R^1$ or $R^6$ is absent if the dotted line adjacent to $R^1$ and $R^6$ is a single bond, and isomers and functional derivatives thereof, in admixture with an acceptable agricultural carrier comprising an agriculturally acceptable carrier cation when R, $R^1$, $R^2$, $R^4$, $R^5$, $R^6$ or $R^7$ are phosphate, sulfoxide or sulfone.

The compositions of the present invention can be applied to combination with other fungicides and/or other growth regulators such as auxins, ethylene, gibberellins, cytokinins and brassinolides to form agricultural solutions possessing germination enhancing properties.

The present invention further includes agricultural compositions to increase plant resistance to water loss through stomata by stimulating the closure of plant stomata, to promote plant emergence, to act as hardeners or dehardeners and to promote freeze resistance in plants and to improve plant resistance to low temperature injury.

The use of the compositions of the present invention to stimulate the closure of stomata is especially beneficial when transplanting plants. When such an operation is performed, plants can experience tremendous shock, wilt and die. Closing the stomata of plants prior to transplanting has proved to be efficient in promoting quick recovery.

The compositions disclosed herein are also useful in promoting plant emergence, thereby reducing the time to maturity of the plants and consequently shortening the time to maturity and harvest. Finally, the hardening and dehardening properties of the compositions of the present invention provide the possibility to either enhance or reduce temperature resistance of plants, to enhance plant resistance to herbicides, to overcome both low and high temperature dormancy and to improve drought and freeze resistance in plants.

Most of the compounds comprised in the compositions of the present invention can be synthesized in short efficient sequences from inexpensive starting materials. The structures and stereochemistry of the synthesized compounds can then be easily established.

The composition of the present invention possess unexpected properties since most of the abscisic acid derivatives that have been synthesized over the years have been used as plant growth inhibitors. They therefore represent the first composition comprising abscisic acid-like chemicals having an effect opposite to that of the natural hormone or growth. Also, the enhanced stability of these compounds in the field, when compared to ABA, allows their effective commercial use in applications such as freezing resistance tolerance and inhibition of transpiration in plants.

Also within the scope of the present invention is an abscisic acid-related compound having the following formula (IA):

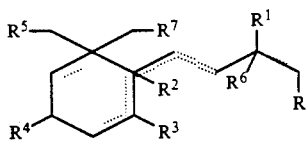

(IA)

wherein

R may be carboxyl, aldehyde, hydroxy, hydroxyloweralkyl, alkoxyloweralkyl, loweralkoxycarbonyl, loweracyloxyloweralkyl, acetylloweralkyl, loweralkanoyl, loweralkylamino, diloweralkylamino, loweralkoxy, loweracyloxy, loweralkylthio, loweralkyl sulphonyl, loweralkyl sulphinyl, amino, carbonyl, halogen, thio, phosphate, sulfoxide, sulfone or deuterium;

$R^1$ may be hydrogen, oxo, hydroxyloweralkyl, loweralkoxy, halogen, thio, sulfoxide, sulfone, phosphate or deuterium;

$R^2$ may be hydrogen, oxo, hydroxy, halogen, thio, phosphate, sulfoxide, sulfone or deuterium;

$R^3$ may be carboxyl, aldehyde, loweralkyl, hydroxyloweralkyl, alkoxyloweralkyl, loweralkoxycarbonyl, loweracyloxyloweralkyl, acetylloweralkyl, loweralkanoyl, loweralkylamino, diloweralkylamino, loweralkoxy, loweracyloxy, loweralkylthio, loweralkyl sulphonyl, loweralkyl sulphinyl, or carbonyl;

and when $R^2$ is oxo or thio, $R^2$ may be linked to both $C_1$ and $C_2$ carbon atoms to form an epoxy or a thioepoxy ring;

$R^4$ may be hydrogen, oxo, halogen, thio, phosphate, sulfoxide, sulfone, deuterium, hydroxy, loweralkylsiloxane, carboxyl, aldehyde, hydroxyloweralkyl, alkoxyloweralkyl, loweralkoxycarbonyl, loweracyloxyloweralkyl, acetylloweralkyl, loweralkanoyl, loweralkylamino, diloweralkylamino, loweralkoxy, loweracyloxy, loweralkylthio, loweralkyl sulphonyl, loweralkyl sulphinyl, amino, carbonyl, cycloalkyl or cycloalkoxy having from 4 to 6 carbon atoms which is optionally substituted by loweralkyl, halogen, oxygen, hydroxy or loweralkoxy;

$R^5$ may be carboxyl, hydroxy, aldehyde, hydroxyloweralkyl, alkoxyloweralkyl, loweralkoxycarbonyl, loweracyloxyloweralkyl, acetylloweralkyl, acetylloweralkyl, acetylloweralkyl, loweralkanoyl, loweralkylamino, diloweralkylamino, loweralkoxy, loweracyloxy, loweralkylthio, loweralkyl sulphonyl, loweralkyl sulphinyl, amino, carbonyl, halogen, hydrogen, oxo, thio, phosphate, sulfoxide, sulfone or deuterium, and when $R^5$ is oxo, it may be linked to the carbon atoms bearing $R^3$;

$R^6$ may be hydrogen, oxo, hydroxyloweralkyl, loweralkoxy, halogen, thio, sulfoxide, sulfone, phosphate or deuterium;

$R^7$ may be carboxyl, hydroxyl, aldehyde, hydroxyloweralkyl, alkoxyloweralkyl, loweralkoxycarbonyl, loweracyloxyloweralkyl, acetylloweralkyl, acetylloweralkyl, loweralkanoyl, loweralkylamino, diloweralkylamino, loweralkoxy, loweracyloxy, loweralkylthio, loweralkyl sulphonyl, loweralkyl sulphinyl, amino, carbonyl, halogen, hydrogen, oxo, thio, phosphate, sulfoxide, sulfone or deuterium, and when $R^7$ is oxo, it may be linked to the carbon atom bearing $R^3$; and wherein the dotted lines may each represent a single bond and the double dotted line represents either a double bond or a triple bond, $R^1$ or $R^6$ is absent if the dotted line adjacent to $R^1$ and $R^6$ is a single bond, and isomers and functional derivatives thereof,
with the proviso that when R is —CHO, —CH$_2$OH or —COOCH$_3$, $R^1$ is CH$_3$, $R^2$ is oxo or OH, $R^3$ is CH$_3$, $R^4$ is oxo or H and $R^5$ is H, the following compounds are excluded from formula (IA):

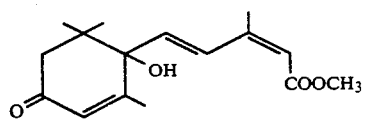

PBI-01

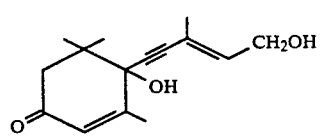

PBI-04

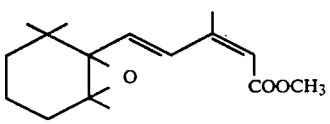

PBI-06

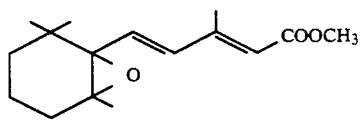

PBI-07

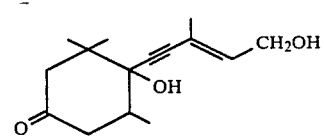

PBI-10

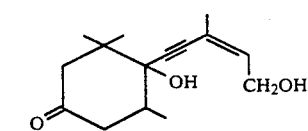

PBI-11

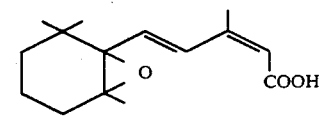

PBI-14

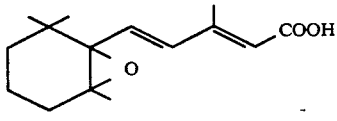

PBI-15

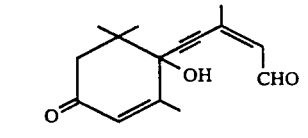

PBI-16

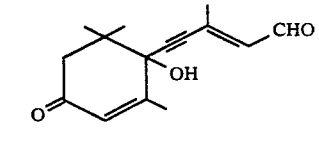

PBI-17

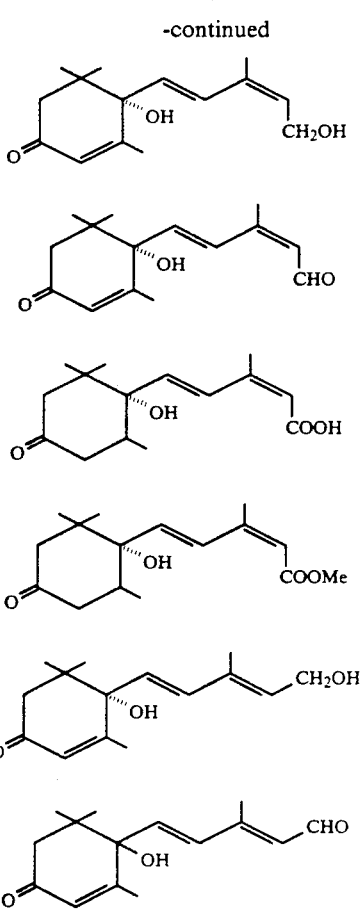

PBI-31

PBI-37

PBI-38

PBI-39

PBI-46

PBI-47

Furthermore, the present invention relates to a method for enhancing germination and growth of plants which comprises treating plant seeds or parts used in propagation with a solution comprising at least one abscisic acid-related compound having the following formula (I):

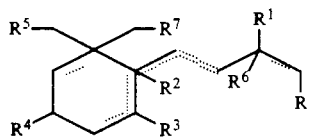

(I)

wherein

R may be carboxyl, aldehyde, hydroxy, hydroxyloweralkyl, alkoxyloweralkyl, loweralkoxycarbonyl, loweracyloxyloweralkyl, acetylloweralkyl, loweralkanoyl, loweralkylamino, diloweralkylamino, loweralkoxy, loweracyloxy, loweralkylthio, loweralkyl sulphonyl, loweralkyl sulphinyl, amino, carbonyl, halogen, thio, phosphate, sulfoxide, sulfone or deuterium;

$R^1$ may be hydrogen, oxo, hydroxyloweralkyl, loweralkoxy, halogen, thio, sulfoxide, sulfone, phosphate or deuterium;

$R^2$ may be hydrogen, oxo, hydroxy, halogen, thio, phosphate, sulfoxide, sulfone or deuterium;

$R^3$ may be carboxyl, aldehyde, loweralkyl, hydroxyloweralkyl, alkoxyloweralkyl, loweralkoxycarbonyl, loweracyloxyloweralkyl, acetylloweralkyl, loweralkanoyl, loweralkylamino, diloweralkylamino, loweralkoxy, loweracyloxy, loweralkylthio, loweralkyl sulphonyl, loweralkyl sulphinyl, or carbonyl;

and when $R^2$ is oxo or thio, $R^2$ may be linked to both $C_1$ and $C_2$ carbon atoms to form an epoxy or a thioepoxy ring;

$R^4$ may be hydrogen, oxo, halogen, thio, phosphate, sulfoxide, sulfone, deuterium, hydroxy, loweralkylsiloxane, carboyl, aldehyde, hydroxyloweralkyl, alkoxyloweralkyl, loweralkoxycarbonyl, loweracyloxyloweralkyl, acetylloweralkyl, loweralkanoyl, loweralkylamino, diloweralkylamino, loweralkoxy, loweracyloxy, loweralkylthio, loweralkyl sulphonyl, loweralkyl sulphinyl amino, carbonyl, cycloalkyl or cycloalkoxy having from 4 to 6 carbon atoms which is optionally substituted by loweralkyl, halogen, oxygen, hydroxy or loweralkoxy;

$R^5$ may be carboxyl, hydroxy, aldehyde, hydroxyloweralkyl, alkoxyloweralkyl, loweralkoxycarbonyl, loweracyloxyloweralkyl, acetylloweralkyl, acetylloweralkyl, loweralkanoyl, loweralkylamino, diloweralkylamino, loweralkoxy, loweracyloxy, loweralkylthio, loweralkyl sulphonyl, loweralkyl sulphinyl, amino, carbonyl, halogen, hydrogen, oxo, thio, phosphate, sulfoxide, sulfone or deuterium, and when $R^5$ is oxo, it may be linked to the carbon atom bearing $R^3$;

$R^6$ may be hydrogen, oxo, hydroxyloweralkyl, loweralkoxy, halogen, thio, sulfoxide, sulfone, phosphate or deuterium;

$R^7$ may be carboxyl, hydroxy, aldehyde, hydroxyloweralkyl, alkoxyloweralkyl, loweralkoxycarbonyl, loweracyloxyloweralkyl, acetylloweralkyl, acetylloweralkyl, acetylloweralkyl, loweralkanoyl, loweralkylamino, diloweralkylamino, loweralkoxy, loweracyloxy, loweralkylthio, loweralkyl sulphonyl, loweralkyl sulphinyl, amino, carbonyl, halogen, hydrogen, oxo, thio, phosphate sulfoxide, sulfone or deuterium, and when $R^7$ is oxo, it may be linked to the carbon atom bearing $R^3$; and wherein the dotted lines may each represent a single bond and the double dotted line represents either a double bond or a triple bond, $R^1$ or $R^6$ is absent if the dotted line adjacent to $R^1$ and $R^6$ is a single bond, and isomers and functional derivatives thereof, in admixture with an acceptable agricultural carrier comprising an agriculturally acceptable carrier cation when R, $R^1$, $R^2$, $R^4$, $R^5$, $R^6$ or $R^7$ are phosphate, sulfoxide or sulfone.

Methods for 1° stimulating the closure of plant stomata through treatment of plant roots or leaves with an agricultural solution comprising at least one compound of formula I, 2° enhancing emergence and maturation of plants through treatment of plant parts used in propagation with an agricultural solution comprising at least one compound of formula I, 3° enhancing plant growth at low temperature and improving plant resistance to low temperature injury through treatment of plant parts used in propagation with an agricultural solution comprising at least one compound of formula I, 4° enhancing freeze resistance in plants through treatment of plant parts with a solution comprising at least one compound of formula I and 5° enhancing the moisture content of plants through treatment of plants with an agricultural solution comprising at least one compound of formula I also fall within the scope of the present invention.

IN THE DRAWINGS

FIG. 6 represents the number of Westar Canola (Brassica napus) seeds previously treated with various concentrations of ABA related compound PBI-07.

FIG. 7 represents the number of Westar Canola plants emerged in the field after sowing Westar Canola seeds previously treated with various concentrations of ABA related compound PBI-10.

FIG. 8 represents the number of Katepwa plants emerged in the field after sowing Katepwa wheat seeds previously treated with various concentrations of ABA related compound PBI-03.

FIG. 9 represents the number of Katepwa plants emerged in the field after sowing Katepwa wheat seeds previously treated with various concentrations of ABA related compound PBI-10.

FIG. 10 represents the number of Katepwa plants emerged in the field after sowing Katepwa wheat seeds previously treated with various concentrations of ABA related compound PBI-19.

FIG. 11 represents the number of Katepwa plants emerged in the field after sowing Katepwa wheat seeds previously treated with various concentrations of ABA related compound PBI-27.

FIG. 12 represents the variation in the transpiration rates of tomato plants treated with ABA related compound PBI-41.

Figure 1:
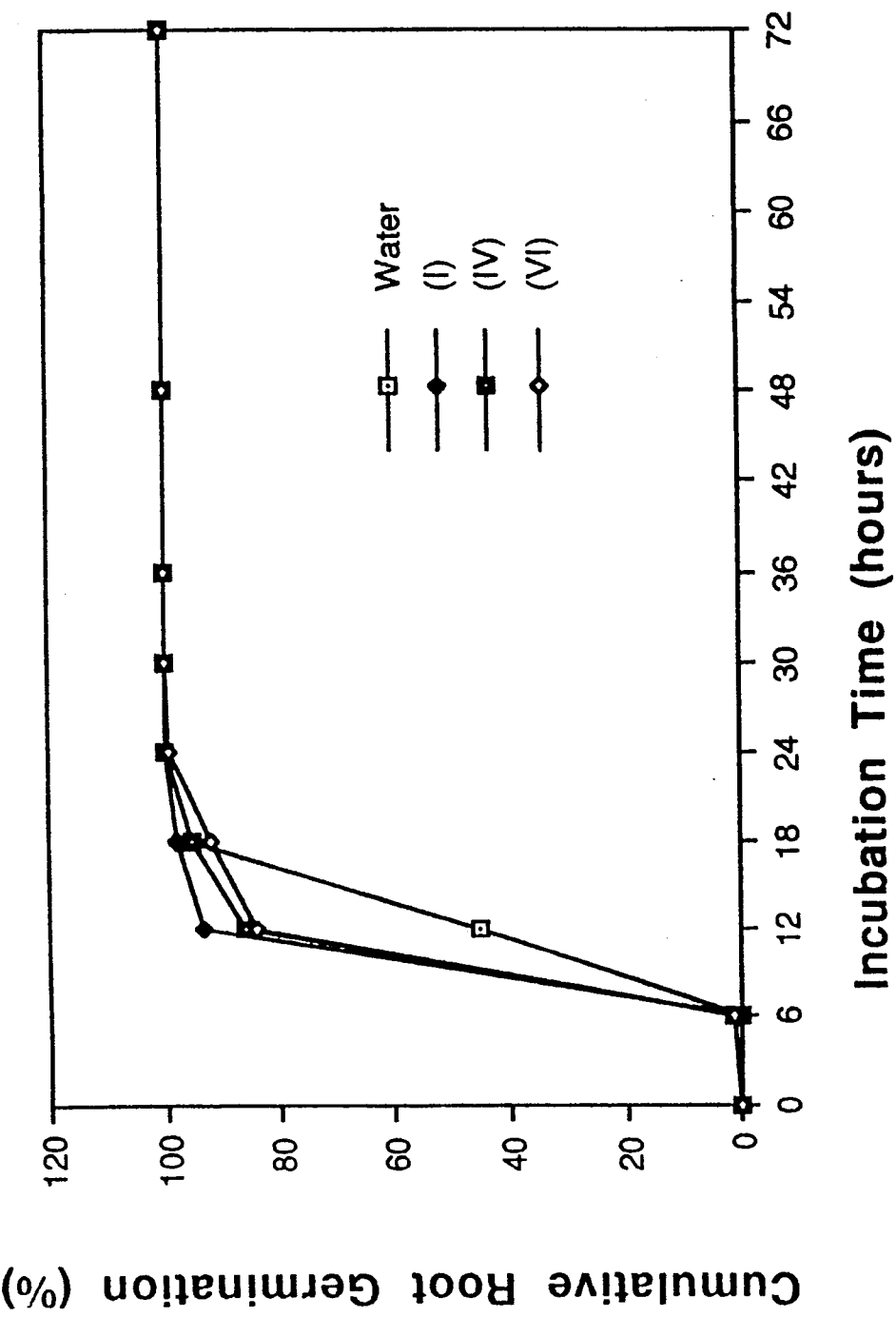
FIG. 1 represents the influence of abscisic acid analogs PBI-03, PBI-07 and PBI-11 on the enhancement of germination of cress seeds.

As used herein, the term halogen includes chlorine, bromine, iodine and fluorine. The terms loweralkyl, loweracyloxyloweralkyl, loweralkanoyl, loweralkoxycarbonyl, loweralkoxy and loweracyloxy, wherever employed, include straight and branched alkyl, acyloxyloweralkyl, alkanoyl, alkoxy and acyloxy groups having 1 to 10 carbon atoms in the alkyl, acyloxyloweralkyl, alkanoyl, alkoxycarbonyl, alkoxy or acyloxy moiety.

DETAILED DESCRIPTION OF THE INVENTION

Growth promoting agricultural compositions comprising abscisic acid related compounds Some of the abscisic acid related compounds that are to be used in the context of the present invention are not novel and have been previously synthesized. Known abscisic acid-related compounds that have been described as growth inhibiting agents but that have been unexpectedly found to possess the properties referred to above fall within the scope of the following composition that also includes novel abscisic acid-related compounds of the present invention. This composition comprises a compound having the following formula (I):

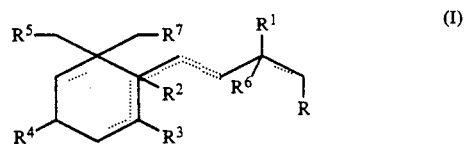

wherein

R may be carboxyl, aldehyde, hydroxy, hydroxyloweralkyl, alkoxyloweralkyl, loweralkoxycarbonyl, loweracyloxyloweralkyl, acetylloweralkyl, loweralkanoyl, loweralkylamino, diloweralkylamino, loweralkoxy, loweracyloxy, loweralkythio, loweralkyl sulphonyl, loweralkyl sulphinyl, amino, carbonyl, halogen, thio, phosphate, sulfoxide, sulfone or deuterium;

$R^1$ may be hydrogen, oxo, hydroxyloweralkyl, loweralkoxy, halogen, thio, sulfoxide, sulfone, phosphate or deuterium; $R^2$ may be hydrogen, oxo, hydroxy, halogen, thio, phosphate, sulfoxide, sulfone or deuterium;

$R^3$ may be carboxyl, aldehyde, loweralkyl, hydroxyloweralkyl, alkoxyloweralkyl, loweralkoxycarbonyl, loweracyloxyloweralkyl, acetylloweralkyl, loweralkanoyl, loweralkylamino, diloweralkylamino, loweralkoxy, loweracyloxy, loweralkylthio, loweralkyl sulphonyl, loweralkyl sulphinyl, or carbonyl; and when $R^2$ is oxo or thio, $R^2$ may be linked to both $C_1$ and $C_2$ carbon atoms to form an epoxy or a thioepoxy ring;

$R^4$ may be hydrogen, oxo, halogen, thio, phosphate, sulfoxide, sulfone, deuterium, hydroxy, loweralkylsiloxane, carboxyl, aldehyde, hydroxyloweralkyl, alkoxyloweralkyl, loweralkoxycarbonyl, loweracyloxyloweralkyl, acetylloweralkyl, loweralkanoyl, loweralkylamino, diloweralkylamino, loweralkoxy, loweracyloxy, loweralkylthio, loweralkyl sulphonyl, loweralkyl sulphinyl, amino, carbonyl, cycloalkyl or cycloalkoxy having from 4 to 6 carbon atoms which is optionally substituted by loweralkyl, halogen, oxygen, hydroxy or loweralkoxy;

$R^5$ may be carboxyl, hydroxy, aldehyde, hydroxyloweralkyl, alkoxyloweralkyl, loweralkoxycarbonyl, loweracyloxyloweralkyl, acetylloweralkyl, acetoxyloweralkyl, loweralkanoyl, loweralkylamino, diloweralkylamino, loweralkoxy, loweracyloxy, loweralkylthio, loweralkyl sulphonyl, loweralkyl sulphinyl, amino, carbonyl, halogen, hydrogen, oxo, thio, phosphate, sulfoxide, sulfone or deuterium, and when $R^5$ is oxo, it may be linked to the carbon atom bearing $R^3$;

$R^6$ may be hydrogen, oxo, hydroxyloweralkyl, loweralkoxy, halogen, thio, sulfoxide, sulfone, phosphate or deuterium;

$R^7$ may be carboxyl, hydroxy, aldehyde, hydroxyloweralkyl, alkoxyloweralkyl, loweralkoxycarbonyl, loweracyloxyloweralkyl, acetylloweralkyl, acetoxyloweralkyl, loweralkanoyl, loweralkylamino, diloweralkylamino, loweralkoxy, loweracyloxy, loweralkylthio, loweralkyl sulphonyl, loweralkyl sulphinyl, amino, carbonyl, halogen, hydrogen, oxo, thio, phosphate, sulfoxide, sulfone or deuterium, and when $R^7$ is oxo, it may be linked to the carbon atom bearing $R^3$; and wherein the dotted lines may each represent a single bond and the double dotted line represents either a double bond or a triple bond, $R^1$ or $R^6$ is absent if the dotted line adjacent to $R^1$ and $R^6$ is a single bond, and isomers and functional derivatives thereof, in admixture with an acceptable agricultural carrier comprising an agriculturally acceptable carrier cation when R, $R^1$, $R^2$, $R^4$, $R^5$, $R^6$ or $R^7$ are phosphate, sulfoxide or sulfone.

A preferred group of the formula I compounds are those in which

R is carboxyl, aldehyde, hydroxyloweralkyl, alkoxyloweralkyl, loweralkoxycarbonyl, loweracyloxyloweralkyl or acetylloweralkyl;

$R^1$ is loweralkyl;

$R^2$ is hydrogen, hydroxy or oxo and wherein the oxo group may be linked to both $C_1$ and $C_2$ carbons to form an epoxy ring;

$R^3$ is loweralkyl;

$R^4$ is hydrogen, oxo, hydroxy or loweralkylsiloxane;

$R^5$ is hydrogen; and $R^6$ is hydroxy.

The most preferred known compounds to be used in the composition of the present invention have the following formulae:

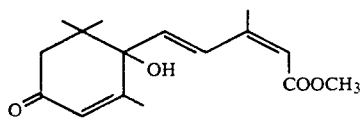
PBI-01

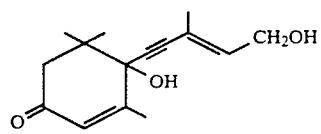
PBI-04

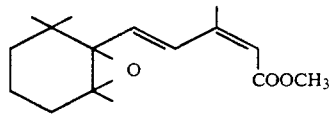
PBI-06

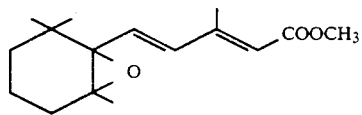
PBI-07

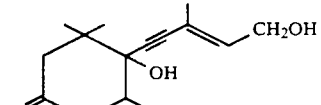
PBI-10

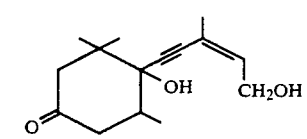
PBI-11

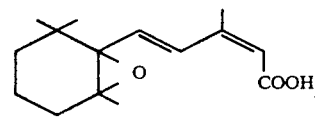
PBI-14

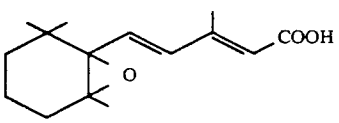
PBI-15

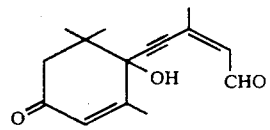
PBI-16

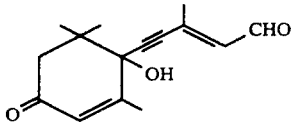
PBI-17

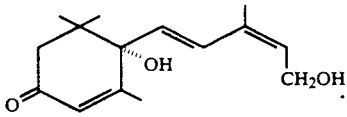
PBI-31

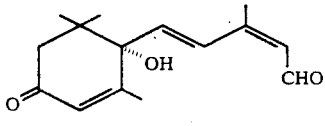
PBI-37

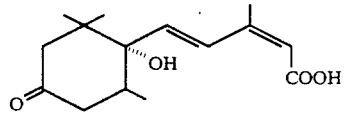
PBI-38

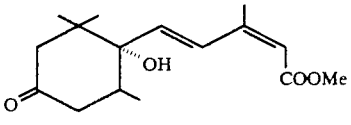
PBI-39

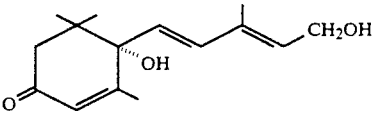
PBI-46

PBI-47

One may refer to the following publications that describe the synthesis of these compounds for which either racemic mixtures or a given isomer may be used: Agr. Biol. Chem. 46(3), 817–818, 1982, Agr Biol. Chem. Vol. 33, No. 2, p. 296–298 (1969), J. Chem. Soc. Pekin Trans. 1, 1984, 2147–2157, Planta 121: 263–272 (1974), Helv. Chim. Acta 59, 1424, (1976) and U.S. Pat. No. 4,153,615. The compounds represented in formula I shown above may therefore be combined with suitable agricultural carriers to provide compositions to be used for the treatment of plant including plant parts used in propagation.

Some of the compounds used in the context of the present invention will have chemical structures containing asymetric carbon atoms, and therefore will be obtained as optical isomers. The present invention therefore intends to cover racemic mixtures as well as isolated optical isomers of the compounds of formulae I and IA, obtained through resolution techniques well-known to those skilled in the art. These isomers may also be obtained through appropriate chemical synthesis, some examples of which are set forth in the present application. Generally speaking, the compounds of formulae I and IA have been used as racemic mixtures unless otherwise indicated.

Novel compounds useful as plant growth promoters

The present invention also relates to novel abscisic acid-related compounds useful as effective growth promoters in plants. These compounds have the following formula (IA):

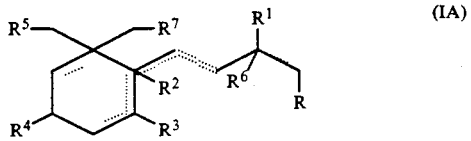

wherein

R may be carboxyl, aldehyde, hydroxy, hydroxyloweralkyl, alkoxyloweralkyl, loweralkoxycarbonyl, loweracyloxyloweralkyl, acetylloweralkyl, loweralkanoyl, loweralkylamino, diloweralkylamino, loweralkoxy, loweracyloxy, loweralkylthio, loweralkyl sulphonyl, loweralkyl sulphinyl, amino, carbonyl, halogen, thio, phosphate, sulfoxide, sulfone or deuterium;

$R^1$ may be hydrogen, oxo, hydroxyloweralkyl, loweralkoxy, halogen, thio, sulfoxide, sulfone, phosphate or deuterium;

$R^2$ may be hydrogen, oxo, hydroxy, halogen, thio, phosphate, sulfoxide, sulfone or deuterium;

$R^3$ may be carboxyl, aldehyde, loweralkyl, hydroxyloweralkyl, alkoxyloweralkyl, loweralkoxycarbonyl, loweracyloxyloweralkyl, acetylloweralkyl, loweralkanoyl, loweralkylamino, diloweralkylamino, loweralkoxy, loweracyloxy, loweralkylthio, loweralkyl sulphonyl, loweralkyl sulphinyl, or carbonyl;

and when $R^2$ is oxo or thio, $R^2$ may be linked to both $C_1$ and $C_2$ carbon atoms to form an epoxy or a thioepoxy ring;

$R^4$ may be hydrogen, oxo, halogen, thio, phosphate, sulfoxide, sulfone, deuterium, hydroxy, loweralkylsiloxane, carboxyl, aldehyde, hydroxyloweralkyl, alkoxyloweralkyl, loweralkoxycarbonyl, loweracyloxyloweralkyl, acetylloweralkyl, loweralkanoyl, loweralkylamino, diloweralkylamino, loweralkoxy, loweracyloxy, loweralkylthio, loweralkyl sulphonyl, loweralkyl sulphinyl, amino, carbonyl, cycloalkyl or cycloalkoxy having from 4 to 6 carbon atoms which is optionally substituted by loweralkyl, halogen, oxygen, hydroxy or loweralkoxy;

$R^5$ may be carboxyl, hydroxy, aldehyde, hydroxyloweralkyl, alkoxyloweralkyl, loweralkoxycarbonyl, loweracyloxyloweralkyl, acetylloweralkyl, acetoxyloweralkyl, loweralkanoyl, loweralkylamino, diloweralkylamino, loweralkoxy, loweracyloxy, loweralkylthio, loweralkyl sulphonyl, loweralkyl sulphinyl, amino, carbonyl, halogen, hydrogen, oxo, thio, phosphate, sulfoxide, sulfone or deuterium, and when $R^5$ is oxo, it may be linked to the carbon atom bearing $R^3$;

$R^6$ may be hydrogen, oxo, hydroxyloweralkyl, loweralkoxy, halogen, thio, sulfoxide, sulfone, phosphate or deuterium;

$R^7$ may be carboxyl, hydroxy, aldehyde, hydroxyloweralkyl, alkoxyloweralkyl, loweralkoxycarbonyl, loweracyloxyloweralkyl, acetylloweralkyl, acetoxyloweralkyl, loweralkanoyl, loweralkylamino, diloweralkylamino, loweralkoxy, loweracyloxy, loweralkylthio, loweralkyl sulphonyl, loweralkyl sulphinyl, amino, carbonyl, halogen, hydrogen, oxo, thio, phosphate, sulfoxide, sulfone or deuterium, and when $R^7$ is oxo, it may be linked to the carbon atom bearing $R^3$; and wherein the dotted lines may each represent a single bond and the double dotted line represents either a double bond or a triple bond, $R^1$ or $R^6$ is absent if the dotted line adjacent to $R^1$ and $R^6$ is a single bond, and isomers and functional derivatives thereof, with the proviso that when R is —CHO, —CH$_2$OH or —COOCH$_3$, $R^1$ is CH$_3$, $R^2$ is oxo or OH, $R^3$ is CH$_3$, $R^4$ is oxo or H and $R^5$ is H, the following compounds are excluded from formula (I):

PBI-01

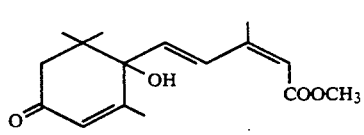

PBI-04

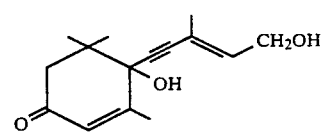

PBI-06

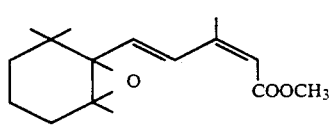

PBI-07

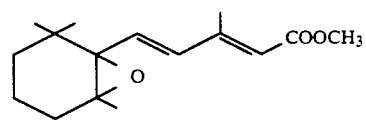

PBI-10

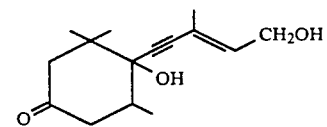

PBI-11

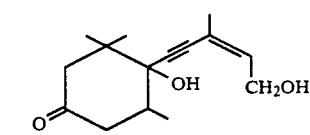

PBI-14

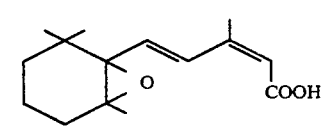

PBI-15

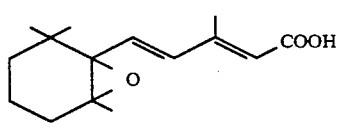

PBI-16

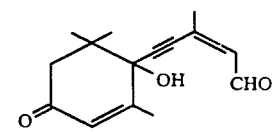

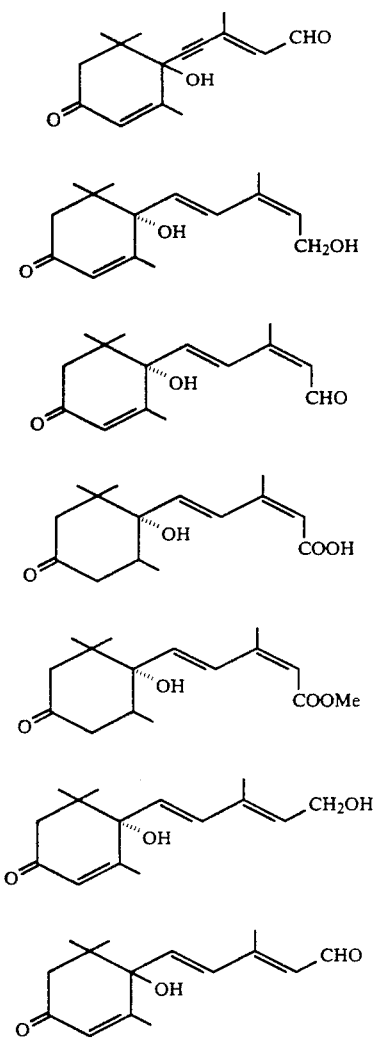

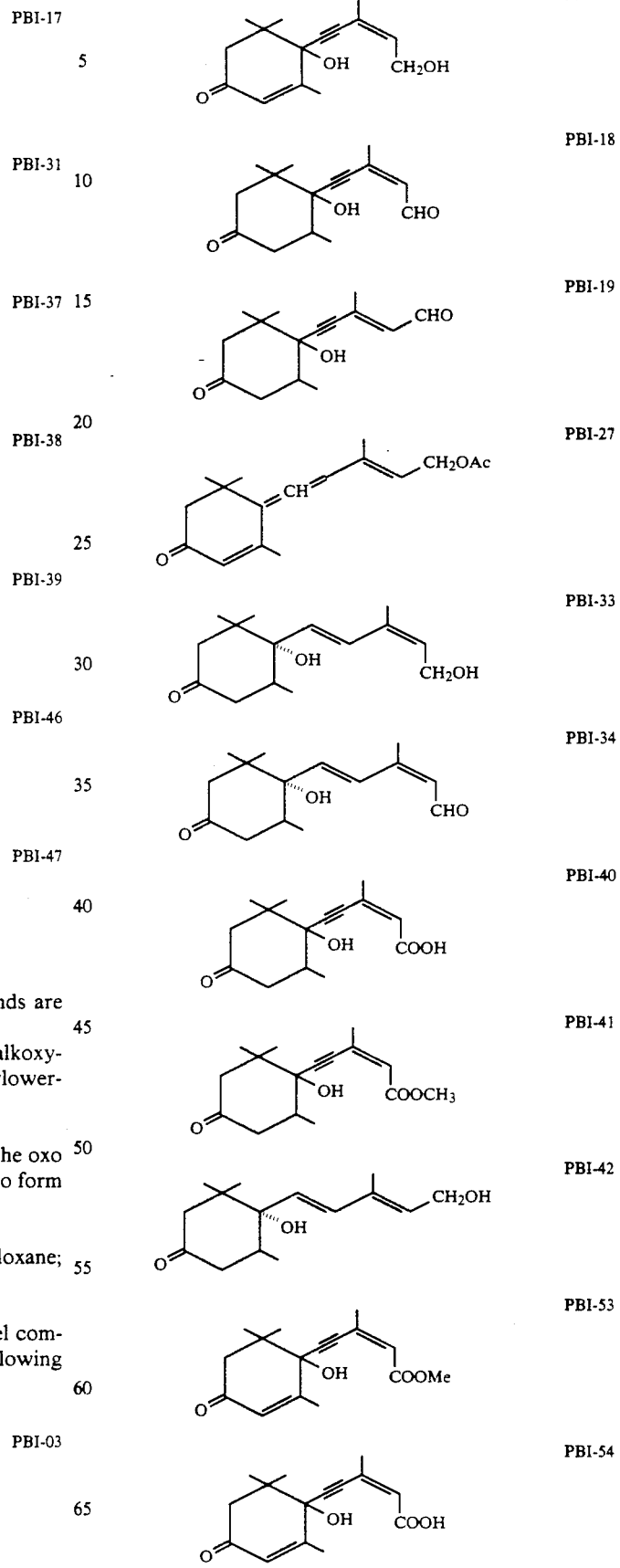

A preferred group of the formula I compounds are those in which

R is carboxyl, aldehyde, hydroxyloweralkyl, alkoxyloweralkyl, loweralkoxycarbonyl, loweracyloxyloweralkyl or acetylloweralkyl, $R^1$ is loweralkyl $R^2$ is hydrogen, hydroxy or oxo and wherein the oxo group may be linked to both $C_1$ and $C_2$ carbons to form an epoxy group;

$R^3$ is loweralkyl;

$R^4$ is hydrogen, oxo, hydroxy or loweralkylsiloxane;

$R^5$ is hydrogen; and $R^6$ is hydroxy.

Particularly, some of the more preferred novel compounds of the present invention have the following formulae:

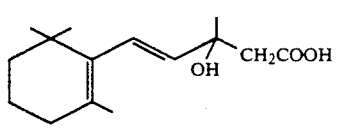

Generally speaking, the novel compounds of the present invention are prepared by alkylation of an appropriate cyclohexanone derivative with an appropriate acetylide derivative. This method is well-known to those skilled in the art.

It will also be understood by those skilled in the art that the compounds having the general formula described above can be found as geometric isomers having cis or trans configuration with respect to the double bond in the carbon chain. Furthermore, although the stereoisomeric configurations have not been indicated in the formulae exemplified above, it is to be understood that all geometric isomers and stereoisomers of the compounds falling within the scope of formula I do fall within the scope of the present invention.

Application of the composition of the present invention to seeds and plant parts ABA related compounds can be applied to seeds or plant parts using various vehicles to insure that the chemicals are active. The rate of application should be such that a sufficient amount of the composition containing the active ingredient is applied to the targeted plant part to obtain the desired plant response and increase in plant yield.

The rate of application will depend on a number of factors, such as environmental conditions, type of crop and the like. It has also been found that timing and rate of application bear a relationship to one another and to the crop to which they are applied, such that the rate of application and the timing thereof bear a relationship to the yield increase. Also, it has been discovered that the activity of some of these compounds on plants is concentration dependent since the compounds seem to be interfering with the action of some of the plant's normal hormones. Furthermore, the tests performed in the field tend to demonstrate that the effects of the compositions of the present invention vary from one species to another depending on the nature and concentration of the compound used. In other words, a given compound may possess germination enhancement properties in Canola while another compound may be active in wheat but not in Canola. Hence, some of the compositions of the present invention are highly specific to certain plant species while others are highly specific to different plant species.

The ABA related compounds, once dissolved in the desired carrier, can be applied in a steep process, as a spray or as a coating. The analogs and metabolites of ABA can also be applied in a paste mixture or through a coating process.

In the case of a spray mixture, the composition will usually be applied at a rate of from about 0.000005 g to 1.5 kg per acre, in a total applied volume of from about 5 l to 100 l per acre.

In the case of a steep process, seeds will be steeped in a solution having a concentration of growth enhancing compound ranging from 0.00000025 g/l to 0.50 g/l for a period of time that may vary from 0.1 to 24 hours. The steeping temperature will usually fall between 10° and 30° C. The seeds are then dried down to about their original moisture content and planted under normal conditions. It is to be mentioned that steeping may be carried out in water or another solvent. The seedlings will usually appear 12 to 72 hours earlier than in the case of normal conditions. Also, increased total germination is observed. Preferably, seeds of wheat, corn, flax, barley, cress and various grasses may be imbibed for 0.1 to 24 hours at a temperature ranging from 10° to 25° C., then air dried to approximately 12% moisture content and sown in the field.

The compounds used in the compositions of the present invention possess the ability to enhance germination and emergence at low temperatures. Cool soils in the spring delay germination, increase the risk of fungal infection and produce uneven stands. The composition described above allows better plants yields at low germination temperatures. Any seed treatment which enhances germination would be of considerable importance for the establishment of grasses which are slow to germinate and only a certain percentage of the seedlings survive to produce a proper coverage.

Also, the use of the compositions of the present invention promotes the obtention of a shorter plant growth cycle. For example, plants grown from seeds imbibed with the composition of the present invention mature faster than plants grown from untreated seeds.

Furthermore, the composition of the present invention, when applied to plant roots, leads to a reduction of the plant's transpiration rate. Water is pulled into the plant via its roots, when a plant transpires water from its leaves. If a plant is transpiring more water than can be pulled into the plant, an automatic mechanism in the plant closes the stomata before irreversible damage occurs. When water becomes available, the stomata open. The transpiration rate of a plant is proportional to the degree at which the plant's stomata are opened. A low transpiration rate therefore indicates that the plant's stomata are practically closed. This property is useful to avoid shock when transplanting from one container to another or from a container to the field.

Finally, application of the composition of the present invention to plants cells is useful to increase the dry matter content of cells during incubation at low temperatures. The increase of the plant's dry matter content is accompanied by a decrease in the plant's water content. Decreases in water content usually signifies an increase in freezing resistance. The compounds of the present invention are therefore useful to promote freezing resistance in plants.

Thus, the compounds of the present invention are useful as seed treatment for agronomic, forestry and horticultural crops. As well, these compounds are useful in the malting and distilling industry, where high alpha-amylase activity in germinating barley is required.

The present invention will be more readily illustrated by referring to the following examples which are introduced only to illustrate rather than limit the scope of the present disclosure.

EXAMPLE 1

Preparation of
(3E)-4-(5-acetoxy-3-methyl-1,3-pentadien-1-ylidene)-3,5,5-trimethyl-2-cyclohexen-1-one PBI-27)

A solution of (2E)-5-(4-oxo-1-hydroxy-2,2,6-trimethylcyclohexyl)-3-methylpent-2-en-4-yn-1-ol (570 mg, 2.3 mmol) and potassium hydrogen sulfate (approx. 20 mg) in acetic acid (3.0 ml) and acetic anhydride (2.0 ml) was heated under argon for 2.5 h at 100° C. The solution was cooled to room temperature, water was added, and the product was extracted three times with ether. The combined ethereal phases were washed first with saturated sodium bicarbonate solution, then with sodium chloride solution and dried over anhydrous sodium sulfate. Evaporation of the solvent afforded an oil (483 mg) which was chromatographed over silica gel eluting with 30% ether/70% hexane, yielding (3E)-4-(5-acetoxy-3-methyl-1,3-pentadien-1-ylidene)-3,5,5-trimethyl-2-cyclohexen-1-one (148 mg, 23%). The product gave a single spot on tlc (silica gel, 50% ether/50% hexane, $R_f$ 0.3); $^1H$ NMR (360 MHz, CDCl$_3$): 6.31 (br s, H-2, 1H), 5.89 (t, J=1.2 Hz, H-2, 1H) 5.61 (br t,J=7.0 Hz, H-4', 1H). 4.68 (d, J=7.0 Hz, H-5', 2H), 2.38 (br s,H-6,2H_), 1.94 (d,J=1.2 Hz, C-3 methyl, 3H), 1.74 (br s, C-3' methyl, 3H), 1.17 (s, C-5 methyl, 3H), and 1.15 (s, C-5 methyl, 3H); IR (film)$_{max}$ 1910,1730,1650 and 1590 cm$^{-1}$; GC/MS m/z 274(5), 232(7), 214(100) and 199(49); UV (hexane) 267 nm (24,400).

EXAMPLE 2

Alternative preparation of (3E)-4-(5-acetoxy-3-methyl-1,3-pentadien-1-ylidene)3,5,5-trimethyl-2-cyclohexen-1-one (PBI-27)

To a solution of (3E)-4-(5-hydroxy-3-methyl-1,3-pentadien-1-ylidene)-3,5,5-trimethyl-2-cyclohexen-1-one (1.2 g, 5.2 mmol) in acetic anhydride (5.0 mL) and triethylamine (5.0 mL) cooled to 0° C., was added 4,4-dimethylaminopyridine (25 n g). After 15 min. water was added to the reaction mixture, and the product was extracted three times with ether. The combined ethereal extracts were washed with sodium chloride solution, and dried over anhydrous sodium sulfate. Evaporation of the solvent and chromatography over silica gel in the manner described in Example 1 above gave the desired product (680 mg, 48%).

EXAMPLE 3

Preparation of (4E)-5-(2,6,6-trimethylcyclohex-1-enyl)-3-hydroxy-3-methylpentenoic acid (PBI-03)

The corresponding methyl ester of (4E)-5-(2,6,6-trimethylcyclohex-1-enyl)-3-hydroxy-3-methyl-pentenoic acid (10 g, 36 mmol) in ethanol (30 mL) was treated with sodium hydroxide solution (3N, 250 mL) and the solution refluxed for 0.5 h. After cooling, the ethanol was removed at reduced pressure. The basic aqueous phase was extracted three times with ether to remove neutral components. The aqueous phase was then made acidic with hydrochloric acid and the product extracted three times with dichloromethane. The pooled organic extracts were washed with sodium chloride solution and then dried over anhydrous sodium sulfate. Evaporation of the solvent afforded 8.5 g of an oil. Treatment of an analytical sample with diazomethane afforded the starting ester. The acid was employed without further purification. $^1H$ NMR (360 MHz, CDCl$_3$): 6.08 (d, J=16.1 Hz, H-5, 1H), 5.45 (d, J=16.1 Hz, H-4, 1H), 2.65 (s, H-2, 2H), 1.93 (m, H-3', 2H), 1.35-1.55 (m, H-4', H-5', 4H), 0.93, 0.92 (s, H-8, H-9, 6H).

EXAMPLE 4

Preparation of PBI-26 (III)

A solution of (2E)-5-(4-oxo-1-hydroxy-2,2,6-trimethylcyclohexyl)-3-methylpent-2-en-4-yn-1-ol (570 mg, 2.3 mmol) and potassium hydrogen sulfate (approx. 20 mg) in acetic acid (3.0 ml) and acetic anhydride (2.0 ml) was heated under argon for 2.5 h at 100° C. The solution was cooled to room temperature, water was added, and the product was extracted three times with ether. The combined ethereal phases were washed first with saturated sodium bicarbonate solution, then with sodium chloride solution and dried over anhydrous sodium sulfate. Evaporation of the solvent afforded and oil (483 mg) which was chromatographed over silica gel eluting with 50% ether/50% hexane yielding compound III (48 mg, 9%).

EXAMPLE 5

Z-5-(5-hydroxy-3-methyl-pent-3-en-1-ynyl)-3,5,5-trimethyl-2-cyclohexen-1-one (1) (PBI-05)

A solution of Z-3-methylpent-2-en-4-yn-1-ol (Fluka, 7.9 g, 80 mmol) in dry THF (200 mL) under an argon atmosphere was cooled to about −60° C. in a dry ice-acetone bath. n-Butyllithium (Aldrich, 1.6M in hexane, 103 mL, 164 mmol) was added dropwise with stirring, followed after 0.5 h by a solution of oxoisophorone (Fluka, 6.1 g, 40 mmol) in dry THF (80 mL). A heavy precipitate was obtained at the end of the addition. The reaction mixture was stirred for 45 min. before it was poured into water and extracted three times with ether. The combined organic extracts were washed twice with saturated NaCl and dried over anhydrous Na2SO4. Evaporation of solvent gave a yellow oil (18 g) as the crude product. Purification of the product by flash column chromatography, with 50% ether+50% hexane followed by 100% ether as eluents, gave the alkylation product (6.9 g, 70% yield) as a yellow oil, ir: 3620 (sharp, medium, OH), 3420 (broad, medium, OH), 2220 (weak, acetylene), 1660 (strong, C=O) cm-1; 1H nmr d: 5.83 (tq, J=6.6, 1.5 Hz, 1H, =CH), 5.76 (q, J=1.3 Hz, 1H, =CH), 4.17 (d, J=6.6 Hz, 2H, CH2OH), 3.3 (1H, OH), 2.37 (m, 2H, CH2), 2.05 (d, J=1.3 Hz, 3H, vinyl CH3), 1.79 (m, 3H, vinyl CH3), 1.12 and 1.03 (2s, 6H, 2CH3); 13C nmr d: 198.76 (s, C=O), 160.89 (s, =C), 136.74 (d, =CH), 125.75 (d, =CH), 120.02 (=C), 92.80 and 85.19 (2s, 2 acetylenic C), 74.59 (s, C—OH), 65.74 and 60.93 (2t, 2CH2), 41.79 (s, C), 25.11, 22.81, 19.74 and 15.12 (4q, 4CH3); ms m/z: 248 (M+, approx. 0.05), 230 (7), 192 (18), and 174 (100).

EXAMPLE 6

9-Z-9-(5-hydroxy-3-methylpent-3-en-1-ynyl)-3,3,8,8,10-pentamethyl-1,5-dioxaspiro[5,5]undecan-9-ol (2)

A mixture of 2,2,6-trimethyl-1,4-cyclohexanedione (1.07 g, 6.9 mmol), 2,2-dimethyl-1,3-propanediol (0.95 g, 9.1 mmol), p-toluenesulfonic acid (59 mg), and benzene (15 mL) was heated to reflux under a Dean-Stark water separator for 2 h. The reaction mixture was allowed to cool to room temperature before it was neutralized with saturated NaHCO3, washed with H2O, and dried over anhydrous Na2SO4. Evaporation of solvent gave a colorless oil (1.76 g) as the crude product, which was distilled using the Kugel-rohr apparatus (about 150° C., 0.5 mm Hg) to give pure ketal as a colorless oil (1.60 g, 96%), ir: 1710 (Strong, C=O) cm-1; 1H nmr d: 3.61 and 3.53 (2d, J=11.4 Hz, 2 axial H of CH2O), 3.48 and 3.41 (2dd, J=11.4, 1.6 Hz, 2 equatorial H of CH2O), 2.85 (m, 1H, CH), 2.47 (dd, J=14.2, 3.7 Hz, 1H, equatorial H of CH2), 2.38 (ddd, J=13.5, 5.3, 3.8 Hz, 1H, equatorial H of CH2), 1.58 (d, J=14.2 Hz, axial H of CH2), 1.56 (dd, J=13.5, 13.5 Hz, axial H of CH2), 1.16 (s, 3H, CH3), 0.97 (s, 6H, 2CH3), 0.91 (d, J=6.6 Hz, 3H, CHCH3), 0.85 (s, 3H, CH3); ms m/e: 240 (M+, 0.58), 141 (27), 155 (98), 83 (27), 69 (100). Ketal 1.31 g, 5.5 mmol) was reacted with Z-3-methylpent-2-en-4-yn-1-ol (0.65 g, 6.7 mmol) and n-butyllithium (1.6M in hexane, 8 mL, 12.8 mmol) in dry THF by the procedure described for the preparation of Z-5-(5-hydroxy-3-methyl-pent-3-en-1-ynyl)-3,5,5-trimethyl-2-cyclohexen-1-one. The crude product (yellow oil, 2.6 g) obtained was purified by flash column chromatography using 75% ether+25% hexane as eluent and subsequent distillation using the Kugel-rohr apparatus (about 250° C., 0.06 mm Hg) to give ketal (2) (1.40 g, 77%), ir: 3610 (strong, sharp, OH), 3440 (broad, medium, OH), 1110 and 1090 (strong, C—O) cm-1; 1H nmr d: 5.50 (ddq, J=6.7, 6.7, 1.5 Hz, 1H, =CH), 4.29 (broad s, 2H, CH2OH), 3.55 (d, J=11.3 Hz, 2H, 2 axial H of CH2O), 3.38 and 3.36 (2dd, J=11.3, 1.9 Hz, 2H, 2 equatorial H of CH2O), 2.51 (dd. J=14.3, 3.2 Hz, 1H, equatorial H of CH2), 2.18 (m, 1H, CH), 1.98 (ddd, J=13.8, 3.4, 3.4 Hz, 1H, equatorial H of CH2), 1.84 (m, 3H, vinyl CH3), 1.53-1.61 (m, 2H, 2 axial H of CH2), 1.11, 1.09, 1.06, 1.05, 1.04 and 0.83 (15H, 5CH3); ms (trimethylsilyl ether) m/z: 408 (M+ of trimethylsilyl ether), 155 (100); high resolution ms (trimethylsilyl ether): calc. for C23H40O4Si 408.2696, found 408.2718.

EXAMPLE 7

Z-4-(5-acetoxy-3-methyl-pent-4-en-1-ynyl)-3,5,5-trimethylcyclohex-3-en-1-one (3)

A mixture of (Z)-4-hydroxy-4-(5-hydroxy-3-methyl-pent-3-en-1-ynyl)-3,5,5-trimethylcyclohexanone 795 mg, 3.1 mmol), glacial acetic acid (5 mL), acetic anhydride (5 mL), and KHSO4 (440 mg, 3.2 mmol) was heated to 70° C. under argon for 5 h. Then the mixture was cooled to room temperature and slowly added to a chilled (ice bath) and stirred mixture of hexane and saturated NaHCO3. More saturated NaHCO3 was added until the pH of the aqueous phase was about 6-7. The organic and aqueous layers were then separated, and the aqueous layer was extracted with hexane. The combined hexane layers were washed with saturated NaHCO3, H2O, and dried over anhydrous Na2SO4. Removal of solvent gave a yellow oil (737 mg) which on purification by flash column chromatography using 75% ether+25% hexane as solvent gave compound (3) (600 mg, 70%) as a yellow oil, ir: 1730 (strong, broad) cm-1; 1H nmr d: 5.77 (ddq, J=7.0, 7.0, 1.5 Hz, 1H, =CH), 4.76 (dd, J=7.0, 1.0 Hz, 2H CH2O), 2.90 (broad s, 2H, CH2), 2.39 (s, 2H, CH2), 2.03 (s, 3H, CH3COO), 1.94 and 1.93 (2m, 6H, 2 vinyl CH3), 1.16 (s, 6H, 2CH3); ms m/z: 274 (M+, 30), 214 (100).

EXAMPLE 8

Z-4-(5-acetoxy-3-methyl-pent-3-en-1-ynyl)-3,4-epoxy-3,5,5-trimethylcyclohexan-1-ol (4)

To a solution of Z-4-(5-acetoxy-3-methyl-pent-3-en-1-ynyl)-3,5,5-trimethylcyclohex-3-en-1-ol (42 mg, 0.15 mmol) in toluene (6 mL) was added t-butyl hydroperoxide (3M solution in 2,2,4-trimethylpentane, 0.07 mL, 0.21 mmol) and vanadyl acetylacetonate (3 mg, 0.01 mmol). The reaction mixture, which was reddish orange in color, was stirred under argon at room temperature for 20 min. and then was heated to 70° C. for 30 min. The color of the mixture changed to yellow. After cooling to room temperature, saturated NaHSO3 was added with stirring until there was no peroxide as indicated by peroxide test tapes. The organic and aqueous layers were separated. The aqueous layer was extracted three times with ether. The combined organic layers were washed with H2O, saturated NaHCO3, H2O and dried over anhydrous Na2SO4. Evaporation of solvent gave yellow oil (46 mg) which was purified using the Chromatotron ™ sold by Harrison Scientific and with 75% ether+25% hexane as solvent to give compound (4) as a colorless oil (17 mg, 38%), ir: 3620 (weak, sharp, OH), 3500 (weak, broad, OH), 1740 (strong, sharp, C=O) cm-1; 1H nmr d: 5.80 (ddq, J=6.9, 6.9, 1.6 Hz, 1H, =CH), 4.71 (dd, 6.9, 1.0 Hz, 2H, CH2O), 3.83 (m, 1H, CHOH), 2.19 (ddd, J=14.7, 6.8, 1.5 Hz, 1H, CH2), 2.03 (s, 3H, CH3COO), 1.89 (m, 3H, vinyl CH3), 1.81 (dd, J=14.7, 8.9 Hz, 1H, CH2), 1.47 (s, CH3), 1.37 (ddd, J=12.7, 4.0, 1.5 Hz, 1H, CH2), 1.18 (s, 6H, 2CH3); ms (isobutane CI) m/z: 293 (M+1), 331 (M+39); (NH4Cl CI): 310 (M+18), 275 (M−17), 233 (M−59).

Alternatively, molybdenum hexacarbonyl could be used in the above procedure instead of vanadyl acetylacetonate but longer reaction time was required.

EXAMPLE 9

Z-4-(5-hydroxy-3-methyl-pent-3-en-1-ynyl)-3,4-epoxy-3,5,5-trimethylcyclohexan-1-ol (5)

A mixture of Z-4-(5-acetoxy-3-methyl-pent-3-en-1-ynyl)-3,4-epoxy-3,5,5-trimethylcyclohexan-1-ol (36 mg, 0.12 mmol), K2CO3 (26 mg, 0.18 mmol), methanol (1 mL) and H2O (1 mL) was stirred at room temperature for 1 h. It was then concentrated by evaporation and the residue was diluted with H2O and extracted with CHCl3. The organic extract was dried over anhydrous Na2SO4. Evaporation of solvent gave compound (5) as a colorless oil (21 mg, 69%), ir: 3620 (sharp, medium, OH) and 3450 (broad, weak, OH) cm-1; 1H nmr d: 5.87 (ddq, J=6.7, 6.7, 1.4 Hz, 1H, =CH), 4.27 (dd, J=6.7, 1.0 Hz, 2H, CH2O), 3.82 (m, 1H, CHOH), 2.18 (ddd, J=14.8, 6.8, 1.4 Hz, 1H, CH2), 1.86 (m, 3H, vinyl CH3), 1.79 (dd, J=14.8, 9.0 Hz, 1H, CH2), 1.46 (s, CH3), 1.36 (ddd, J=12.7, 4.1, 1.5 Hz, 1H, CH2), 1.16 and 1.17 (2s, 6H, 2CH3); 13C nmr d: 136.36 (d, =CH), 119.95 (s, =C), 90.95 and 83.99 (2s, 2 acetylenic C), 65.08 and 64.52 (2s, C—O—C), 63.29 (d, CHOH), 61.15, 41.84 and 38.16 (3t, 3 CH2), 34.83 (s, C), 27.03, 25.60, 22,98 and 22.92 (4q, 4CH3); ms (NH4Cl CI) m/z: 268 (M+18), 251 (M+1), 233 (M−17).

EXAMPLE 10

Trans (−)-(4R,6R)-4-t-Butyldimethylsilyloxy-2,2,6-trimethylcyclohexanone

A mixture of trans (4R,6R)-4-hydroxy-2,2,6-trimethylcyclohexanone (115 mg, 0.73 mmol), t-butyldimethylsilyl chloride (Aldrich, 202 mg, 1.27 mmol), imidazole (100 mg, 1.47 mmol) and dry DMF (3 mL) was stirred at room temperature under an argon atmosphere for 1.5 h. Then water was added and the mixture was extracted three times with ether. The ether extract was washed with saturated NaCl and dried over anhydrous Na2SO4. Evaporation of solvent gave a colorless oil (325 g) which was distilled using the Kugel-rohr apparatus. After some forerun which was discarded, the desired silyl ether was collected as a colorless oil at 150°-180° C., 9-10 mm Hg (156 mg, 80%). The product solidified on storage at −10° C. to form colorless crystals, mp 29.5°-31.5° C.; [a]D −65.1° C. (c 1.06, CH3OH); ir: 1710 cm-1; 1H nmr d: 0.06 and 0.07 (2s, 6H, CH3SiCH3), 0.89 (s, 9H, 3CH3), 0.98 (s, 3H, CH3), 0.98 (d, J=6.4 Hz, 3H, CHCH3), 1.32 (s, 3H, CH3), 1.57 (ddd, J=13.4, 13.2, 2.7 Hz, H-5ax), 1.65 (dd, J=14.2, 3.4 Hz, 1H, H-3ax), 1.88 (ddd, J=14.2, 3.3, 3.2 Hz, 1H, H-3eq), 1.99 (dddd, J=13.0, 5.3, 3.3, 3.2 Hz, 1H, H-

5eq), 3.16 (ddq, J=13.2, 5.3, 6.4 Hz, 1H, H-6ax), 4.08 (q, J=3.2 Hz, 1H, H-4eq); eims m/z: 255 (M+-15, 1), 213 (60), 171 (78), 121 (43), 75 (100); hrms: calc. for C15H30O2Si 270.2015, found 270.2015.

EXAMPLE 11

(−)-1(Z)-(1S,4R,6R)- and (−)-1(Z)-(1R,4R,6R)-1-(5-Acetoxy-3-methylpent-3-en-1-ynyl)-2,2,6-trimethylcyclohexan-1,4-diol (6 and 7)

A solution of Z-3-methylpent-2-en-4-yn-1-ol (Fluka, 1.60 g, 16.7 mmol) in dry THF (20 mL) under an argon atmosphere was cooled to about −60° C. in a dry ice-acetone bath. n-Butyllithium (Aldrich, 1.6M in hexane, 19 mL, 30.4 mmol) was added dropwise with stirring. After all the n-butyllithium had been added the reaction mixture, which was orange in color, was allowed to warm up to −5° C. over 30 min. Then it was again cooled to −60° C. and a solution of trans (−)-(4R,6R)-4-t-Butyldimethylsilyloxy-2,2,6-trimethylcyclohexanone (2.7 g, 10 mmol) in dry THF (20 mL) was added dropwise. After the addition had been completed the reaction mixture was allowed to warm up to 0° C. over 90 min. before it was poured into water and extracted three times with ether. The combined organic extracts were washed twice with saturated NaCl and dried over anhydrous Na2SO4. Evaporation of solvent gave a yellow oil (4.5 g) as the crude product. Purification of the product by flash column chromatography (75% ether+25% hexane as eluent) followed by distillation (Kugel-rohr, 180°-200° C., 0.03 mmHg) gave a mixture of compounds as a yellow oil (2.82 g, 76% yield), gc retention times (DB1701 TM column, 70°-240° C. at 10° C. min-1) 20.05 min. and 19.77 min., ratio of peak areas about 8:1, respectively.

The mixture (2.82 g, 7.6 mmol) was dissolved in pyridine (15 mL). A mixture of acetic anhydride (2.35 g, 23.0 mmol) and pyridine (5 mL) was added, followed by 4-dimethylaminopyridine (Aldrich, 32 mg, 0.26 mmol). The reaction mixture was stirred at room temperature for 1 h before it was worked up by pouring into water and extracting three times with hexane. The combined organic extract was washed with saturated NaCl and dried over anhydrous Na2SO4. Removal of solvent gave a mixture of acetates as a pale yellow oil (3.72 g) which was desilated to give two hydroxyacetates by the procedure below without purification. GC analysis of the crude acetate mixture (DB1701 TM column, 70°-240° C. at 10° C. min-1) showed two components in the ratio of 8:1 (retention times 20.26 min and 20.12 min, respectively).

The crude acetates obtained in the above procedure was stirred with glacial acetic acid (30 mL) and H2O (10 mL), and the mixture was heated to 70° C. under argon for 20 h. After cooling to room temperature, the reaction mixture was diluted with water and extracted three times with CHCl3. The organic extract was washed with H2O, saturated NaHCO3 and dried over anhydrous Na2SO4. Evaporation of solvent gave a yellow oil (2.98 g) as the crude product. Separation by flash column chromatography (75% ether+25% hexane) followed by preparative tlc (same eluent) gave the cis diol (1.26 g, 56% overall yield) and trans diol (0.15 g, 7% overall yield). (−)-1(Z)-(1S, 4R,6R)-1-(5-acetoxy-3-methylpent-3-en-1-ynyl)-2,2,6-trimethylcyclohexan-1,4-diol, colorless oil; gc (DB5 column, 70°-240° C. at 10° C. min-1) retention time 18.37 min.; tlc (90% ether+10% hexane) Rf about 0.30; [a]D −18.4° C. (c 1.02, CH3OH); ir: 3610, 3400, 1735 cm-1; 1 Hnmr d: 1.05 (d, J=6.6 Hz, CHCH3), 1.08 and 1.22 (2s, 6H, 2CH3), 1.55-1.75 (m, 4H, 2CH2), 1.89 (m, 3H, vinyl CH3), 2.03 (s, 3H, CH3COO), 2.34 (m, 1H, CHCH3), 4.02 (m, 1H, CHOH), 4.71 (dd, J=7.0, 1.0 Hz, 2H, CH2O), 5.77 (ddq, J=7.0, 7.0, 1.5 Hz, 1H, =CH); 13C nmr d: 16.05, 20.88, 23.08, 23.28 and 27.39 (5 CH3), 38.77 (C2), 31.92, 40.12 and 44.47 (CH2 and CH), 62.80 and 67.55 (CH2O and CHOH), 79.01 (COH), 84.89 and 95.33 (2 acetylenic C), 123.52 (=C), 130.03 (=CH), 170.83 (C=O); eims m/z: 234 (M+-60, 6), 178 (28), 148 (100).

(−)-1(Z)-(1R, 4R,6R)-1-(5-acetoxy-3-methylpent-3-en-1-ynyl)-2,2,6-trimethylcyclohexan-1,4-diol, colorless oil; gc (DB5 column, 70°-240° C. min-1) retention time 18.50 min.; tlc (90% ether+10% hexane) Rf about 0.35; [a]D −28.3° C. (c 0.92, CH3OH); ir: 3630, 3500, 1735 cm-1; 1H nmr d: 1.05 (s, 3H, CH3), 1.06 (d, J=5.2 Hz, 3H, CHCH3), 1.27, (s, 3H, CH3), 1.43 (ddd, J=14.6, 2.5, 2.5 Hz, 1H, H-3eq), 1.52 (dddd, J=14.3, 3.9, 2.5, 2.5 Hz, 1H, H-5eq), 1.68 (ddd, J=14.3, 12.6, 3.3 Hz, 1H, H-5ax), 1.76 (dd, J=14.6, 3.5 Hz, 1H, H-3ax), 1.89 (m, 3H, vinyl CH3), 2.03 (s, 3H, CH3COO), 2.33 (m, 1H, CHCH3), 4.07 (m, 1H, CHOH), 4.72 (dd, J=7.0, 1.0 Hz, 2H, CH2O), 5.76 (ddq, J=7.0, 7.0, 1.5 Hz, 1H, =CH); 13C nmr d: 16.81, 20.91, 23.21, 26.78 and 27.13 (5 CH3), 38.17 (C2), 30.77, 35.75 and 40.29 (2 CH2 and CH), 62.79 and 67.04 (CH2O and CHOH), 76.53 (COH), 83.52 and 97.37 (2 acetylenic C), 123.62 (=C), 129.99 (=CH), 170.86 (C=O); eims m/z: 234 (M+-60, 3), 178 (10), 148 (100).

EXAMPLE 12

(−)-4-(Z)-(4R,5R)-4-Hydroxy-4-(5-hydroxy-3-methylpent-3-en-1-ynyl)-3,3,5-trimethylcyclohexanone (8)

(Z)-(1R,4R,6R)-1-(5-Acetoxy-3-methylpent-3-en-1-ynyl)-2,2,6-trimethylcyclohexan-1,4-diol (140 mg, 0.47 mmol) was oxidized with pyridinium dichromate (850 mg, 2.26 mmol) in CH2Cl2 (15 mL) to give a keto-acetate as a colorless oil (90 mg, 70%), [a]D −26.0° C. (c 0.78, CH3OH); ir: 3630, 1730 cm-1; 1H nmr d: 1.03 (s, 3H, CH3), 1.17 (d, J=6.3 Hz, 3H, CHCH3), 1.19 (s, 3H, CH3), 1.89 (m, 3H, vinyl CH3), 1.95 (dd, J=13.8, 2.3 Hz, 1H, H-2eq), 2.04 (s, 3H, CH3COO), 2.16 (ddd, J=13.2, 3.8, 2.3 Hz, 1H, H-6eq), 2.31 (ddq, J=12.4, 6.3, 3.8 Hz, 1H, CHCH3), 2.39 (dd, J=13.2, 12.4 Hz, 1H, H-6ax), 2.73 (broad d, J=13.8 Hz, 1H, H-2ax), 4.73 (dd, J=7.0, 0.9 Hz, 2H, CH2O), 5.81 (ddq, J=7.0, 7.0, 1.5 Hz, 1H, =CH); ms m/e: 232 (M+-60, 24), 176 (47), 148 (41), 120 (23), 106 (100); hrms (M+-60 peak): calc. for C15H20O2 232.1463, found 232.1485.

The keto-acetate (90 mg, 0.3 mmol) was hydrolyzed by treating with 5M KOH (5 drops) and methanol (10 mL) to give (−)-4(Z)-(4R,5R)-4-Hydroxy-4-(5-hydroxy-3-methylpent-3-en-1-ynyl)-3,3,5-trimethylcyclo-hexanone as a colorless oil (69 mg, 92%) {(the racemate crystallized on storage at −10° C. to give colorless crystals, mp 72.5°-79.5° C.}, ir: 3630, 1710 cm-1; 1H nmr d: 1.03 (s, 3H, CH3), 1.17 (d, J=6.4 Hz, 3H, CHCH3), 1.19 (s, 3H, CH3), 1.88 (m, 3H, vinyl CH3), 1.96 (dd, J=13.8, 2.3 Hz, 1H, H-2eq), 2.16 (ddd, J=13.3, 3.4, 2.3 Hz, 1H, H-6eq), 2.32 (m, 1H, CHCH3), 2.39 (ddd, J=13.3, 12.8, 0.8 Hz, 1H, H-6ax), 2.72 (ddd, J=13.8, 0.8, 0.8 Hz, 1H, H-2ax), 4.29 (dd, J=6.8, 1.0 Hz, 2H, CH2OH), 5.88 (ddq, J=6.8, 6.8, 1.5 Hz, 1H, =CH); 13C nmr d: 16.76, 23.13, 24.98 and 25.41 (4q, 4CH3), 37.64 (d, CH), 43.06 (s, C3), 44.25, 49.48 and 61.27 (3t, 3CH2), 75.25 (s, COH), 84.47 and 94.85 (2s, 2 acetylenic C), 120.26 (s, =C), 136.08 (d, =CH), 210.86 (s, C=O); ms m/e: 250 (M+, very weak), 232 (5), 179 (23), 165 (66), 106 (100); hrms: calc. for C15H2203 250.1569, found 250.1570.

EXAMPLE 13

(−)-(9Z)-(9S,10R)-9-(5-Hydroxy-3-methylpent-3-en-1-ynyl)-3,3,8,8,10-pentamethyl-1,5-dioxaspiro[5,5]undecan-9-ol (9)

A mixture of (−)-4(Z)-(4S,5R)-4-hydroxy-4-(5-hydroxy-3-methylpent-3-en-1ynyl)-3,3,5-trimethylcyclohexanone (620 mg, 2.49 mmol), 2,2-dimethyl-1,3-propanediol (Aldrich, 460 mg, 4.4 mmol), pyridinium p-tosylate (Aldrich, 19 mg, 0.07 mmol) and benzene (18 mL) was heated to reflux under a Dean-Stark separator for 4 hrs. The reaction mixture was then allowed to cool to room temperature, washed with saturated Na2CO3, saturated NaCl and water. After drying over anhydrous Na2SO4 and evaporation of solvent a yellow oil was obtained as the crude product (1 g). Purification by flash column chromatography (75% ether+25% hexane) gave the desired ketal as a pale yellow oil (750 mg, 90%), [a]D −29.4° C. (c 1.02, CH3OH); ir: 3610, 3440, 1110 and 1090 cm-1; 1H nmr d: 0.83, 1.04, 1.05, 1.06, 1.09, and 1.11 (15H, 5 CH3), 1.53–1.61 (m, 2H, 2 axial H at C7 and C11), 1.84 (m, 3H, vinyl CH3), 1.98 (ddd, J=13.8, 3.4, 3.4 Hz, 1H, H-11eq), 2.18 (m, 1H, CH), 2.51 (dd. J=14.3, 3.2 Hz, 1H, H-7eq), 3.36 and 3.38 (2dd, J=11.3, 1.9 Hz, 2H, 2 equatorial H at C2 and C4), 3.55 (d, J=11.3 Hz, 2H, 2 axial H at C2 and C4), 4.29 (broad s, 2H, CH2OH), 5.50 (ddq, J=6.7, 6.7, 1.5 Hz, 1H, =CH); eims (trimethylsilyl ether) m/z: 408 (M+ of trimethylsilyl ether), 155 (100); hrms (trimethylsilyl ether): calc. for C23H4004Si 408.2696, found 408.2718.

EXAMPLE 14

(−)-9(1E,3Z)-(9R, 10R)-9-(5Hydroxy-3-methyl-1,3-pentadienyl)-3,3,8,8,10-pentamethyl-1,5-dioxaspiro[5,5]-undecan-9-ol (10)

A solution of (−)-(9Z)-(9S,10R)-9-(5-hydroxy-3-methylpent-3-en-1-ynyl)-3,3,8,8,10-pentamethyl-1,5-dioxaspiro[5,5]undecan-9-ol (730 mg, 2.2 mmol) in dry THF (50 mL) was stirred under an argon atmosphere and cooled with an ice-water bath. Sodium is(2-methoxyethoxy)aluminium hydride (RedalR, Alrich, 3.4M in toluene, 1.3 mL, 4.4 mmol) was added dropwise. Some frothing occurred as the RedalR was added. The reaction mixture was stirred at 0° C. until the frothing subsided. Then another portion of RedalR (0.7 mL, 2.2 mmol) was added. After 1.5 h of stirring at 0° C. followed by 1 h at room temperature, the reaction was worked up by pouring into H20 and extracting three times with ether. The combined organic extracts were washed with saturated NaCl and dried over anhydrous Na2SO4. Evaporation of solvent gave a colorless oil (about 1 g) as the crude product which was usually hydrolyzed by the procedure described in Example 15. A small amount of the crude product was purified on the Chromatotron™ (75% ether+25% hexane) to give the desired ketal as a colorless oil, [a]D −64.4° C. (c 1.02, CH3OH); ir: 3600, 1600, 1100, 975, 910 cm-1; 1H nmr d: 0.76, 0.78, 0.85, 1.05 and 1.12 (15H, 5 CH3), 1.34–1.42 (m, 2H, 2 axial H at C7 and C11), 1.85 (d, J=0.9 Hz, 3H, vinyl CH3), 1.97 (ddd, J=14.0, 3.5, 3.5 Hz, 1H, H-11eq), 2.16 (m, 1H, CH), 2.29 (dd, J=14.6, 3.2 Hz, 1H, H-7eq), 3.40 (m, 2H, 2 equatorial H at C2 and C4), 3.57 and 3.58 (2d, J=11.2, 11.4 Hz, respectively, 2H, 2 axial H at C2 and C4), 4.31 (d, J=6.9 Hz, 2H, CH2OH), 5.54 (t, J=8 Hz, 1H, =CH), 5.94 (d, J=15.6 Hz, 1H, =CH), 6.68 (d, J=15.6 Hz, 1H, =CH).

EXAMPLE 15

(−)-4(1E,3Z)-(4R,5R)-4-Hydroxy-4-(5-hydroxy-3-methyl-1,3-pentadienyl)-3,3,5-trimethylcyclohexanone (11)

The crude ketal obtained in the procedure described in Example 14 was hydrolyzed by stirring with 1M HCl (5 drops) and acetone (50 mL) at room temperature for 2 h. After concentration of the acetone solution, saturated NaHCO3 was added and the mixture was extracted with ether. The organic layer was dried with anhydrous Na2SO4 and concentrated to give a yellow oil as the crude product. Flash column chromatography using 90% ether+10% hexane as eluent gave the desired compound as a colorless oil (338 mg, 60%) {The racemate crystallized on standing at room temperature and could be recrystallized from ether-hexane to give colorless crystals, mp 128° C.}, [a]D −41.6° C. (c 0.98, CH3OH); ir: 3610, 3450, 1710, 1610, 975 cm-1; 1H nmr d: 0.84 (d, J=6.3 Hz, CHCH3), 0.89 and 1.01 (2s, 6H, CH3), 1.88 (d, J=0.8 Hz, 3H, vinyl CH3), 2.1–2.3 (m, 4H, H-2eq, CH2 at C6 and CHCH3), 2.46 (d, J=15.8 Hz, 1H, H-2ax), 4.31 (d, J=7.0 Hz, 2H, CH2OH), 5.59 (t, J=7.0 Hz, 1H, =CH), 6.07 (d, J=15.6 Hz, 1H, =CH), 6.81 (dd, J=15.6, 0.4 Hz, 1H, =CH); 13C nmr d: 15.91, 20.78, 22.78 and 25.18 (4q, 4 CH3), 37.39 (d, CH), 41.64 (s, C3), 47.08, 52.88 and 58.34 (3t, 3CH2), 78.12 (s, COH), 128.36, 128.64 and 128.96 (3d, 3 =CH), 134.40 (s, =C), 209.55 (s, C=O); eims (trimethylsilyl ether) m/e: 324 (M+ of trimethylsilyl ether, 3), 73 (100); hrms (trimethylsilyl ether): calc. for C18H3203Si 324.2121, found 324.2109.

EXAMPLE 16

(−)-4(1E,3Z)-(4R,5R)-4-Hydroxy-4-(5-oxo-3-methyl-1,3-pentadienyl)-3,3,5-trimethylcyclohexanone (12)

To a solution of ketoalcohol as described in Example 15 (300 mg, 1.2 mmol) in acetone (30 mL) was added manganese oxide (2.08 g, 24 mmol). The mixture was stirred at room temperature under a drying tube for 1 h before the manganese oxide was removed by filtration. The solid residue was rinsed with acetone and the rinsing was combined with a filtrate. Evaporation of acetone gave the crude aldehyde which was usually oxidized to ester without purification as described in Example 17.

A small amount of aldehyde was purified by preparative tlc (90% ether+10% hexane) followed by recrystallization from ether-hexane to give colorless crystals, mp 106.0°–108.5° C.; [a]D −64.5 (c 0.38, CH3OH); ir: 3550, 1715 and 1665 cm-1; 1H nmr d: 0.89 (d, J=6.4 Hz, 3H, CHCH3), 0.93 and 1.04 (2s, 2CH3), 2.11 (d, J=1.1 Hz, 3H, vinyl CH3), 2.15–2.42 (m, CH2 at C6 and CHCH3), 2.17 (dd, J=14.9, 2.5 Hz, H-2eq), 2.48 (d, J=14.9 Hz, 1H, H-2ax), 5.90 (d, J=7.7 Hz, 1H, =CH), 6.49 and 7.50 (2d, J=15.4 Hz, 2H, 2 =CH), 10.21 (d, J=8.0 Hz, 1H, CH=O); high resolution ms; calc. for C15H2203 250.1569, found 250.1575.

EXAMPLE 17

(−)-(4R, 5R)-Methyl 2′,3′-dihydroabscisate (13)

Crude aldehyde as described in Example 16 (about 1.2 mmol) obtained from the procedure described in Example 16 was dissolved in methanol (30 mL). Manganese oxide (1.79 g, 20 mmol), sodium cyanide (87 mg, 1.7 mmol) and glacial acetic acid (0.10 g, 1.6 mmol) were added. The mixture was stirred at room temperature for 5 h before it was filtered through CeliteR. The manganese oxide residue and celite were rinsed with methanol and the rinsing was combined with the filtrate. The combined rinsing and filtrate was then concentrated, and the residue was partitioned between ether and H2O. the ether layer was separated, dried over anhydrous Na2SO4, and concentrated to give a yellow oil (283 mg) as crude product. Purification on the Chromatotron™ (4 mm silica gel plate, 90% ether+10% hexane) gave (−)-(4R, 5R)-methyl dihydroabscisate as colorless crystals (199 mg, 70% overall yield). Part of the product was recrystallized from ether-hexane to give colorless needles, mp 117.0°–119.5° C.; [a]D −62.7° C. (c 0.90, CH3OH); hplc {Chriacel OD column (18, 19), 10% isopropanol+90% hexane at 1.0 mL min-1} retention time 10.7 min.; ir: 3600, 1710 cm-1; 1H nmr d: 0.88 (d, J=6.3 Hz, 3H, CHCH3), 0.92 and 1.04 (2s, 6H, 2 CH3), 2.03 (d, J=1.2 Hz, 3H, vinyl CH3), 2.15 (dd, J=16.0, 15.0 Hz, H-6ax), 2.15 (dd, J=15.0, 2.5 Hz, H-2eq), 2.30–2.40 (m, 2H, CHCH3 and H-6eq), 2.46 (d, J=14.9 Hz, 1H, H-2ax), 3.69 (s, 3H, OCH3), 5.74 (s, 1H, =CH), 6.46 (d, J=16.0 Hz, 1H, =CH), 7.91 (dd, J=16.0, 0.6 Hz, 1H, =CH); 13C nmr d: 16.00, 21.28, 22.87 and 25.25 (4q, 4 CH3), 37.40 (d, CH), 41.71 (s, C3), 47.10 (t, CH2), 51.10 (q, CH3O), 52.92 (t, CH2), 78.14 (s, COH), 117.62, 129.41 and 135.15 (3d, 3 =CH), 149.41 (s, =C), 166.51 (s, OC=O), 209.12 (s, C=O); eims m/e: 280 (M+, 2), 192 (35), 164 (23), 123 (100); hrms: calc. for C16H24O4 280.1675, found 280.1664. Anal. calc. for C16H24O4: C 68.53%, H 8.63%; found: C 68.67%, H 8.74%.

EXAMPLE 18

(−)-(4R, 5R)-2′,3′-dihydroabscisic acid (14)

A mixture of (−)-(4R, 5R)-methyl 2,′,3′-dihydroabscisate (166 gm, 0.6 mmol), 2M KOH (6 mL) and methanol (3mL) was stirred at room temperature for 4 h. Most of the methanol was then evaporated. The residue was diluted with H2O, extracted with ether, and the ether extract was discarded. The aqueous layer was acidified with 1M HCl and then extracted with CHCl3. The CHCl3 layer gave, after drying over anhydrous Na2SO4 and evaporation of solvent, (−)-(4R, 5R)-dihydroabscisic acid as white crystals (118 mg, 78%). Part of the product was recrystallized from CHCl3-hexane to give white crystals, mp 177°–184° C. {lit. mp of racemate 193.5° C.}; [a]D −65.2° C. (c 0.66, CH3OH); ir: 2800–3200, 1715, 1690 cm-1; 1H nmr d: 0.89 (d, J=6.4 Hz, CHCH3), 0.93 and 1.06 (2s, 6H, 2 CH3), 2.08 (s, 3H, vinyl CH3), 2.14–2.43 (m, 4H, CHCH3, CH2 at C6 and H-2eq), 2.47 (d, J=14.9 Hz, 1H, H-2ax), 5.77 (broad s, 1H, =CH), 6.50 and 7.88 (2d, J=16.0 Hz, 2H, 2 =CH); eims (trimethylsilyl ether) m/z: 338 (M+, 2), 192 (30), 73 (100); hrms (trimethylsilyl ether): calc. for C18H30O4Si 338.1913, found 338.1921. Anal. calc. for C15H22O4: C 67.63%, H 8.33%; found C 67.21%, H 8.30%.

EXAMPLE 19

(−)-(9Z)-(9R,10R)-9-(5-Hydroxy-3-methylpent-3-en-1-ynyl)-3,3,8,8,10-pentamethyl-1,5-dioxaspiro[5,5]undecan-9-ol (15)

(−)-4(Z)-(4R,5R)-4-Hydroxy-4-(5-hydroxy-3-methylpent-3-en-1-ynyl)-3,3,5-trimethylcyclohexanone (130 mg, 0.52 mmol) was treated with a mixture of 2,2-dimethyl-1,3-propanediol (160 mg, 1.53 mmol), pyridinium p-tosylate (9 mg, 0.04 mmol) and benzene (4 mL) according to the procedure described in Example 13. The desired ketal was obtained as a pale yellow oil (149 mg, 89%), [a]D −27.8° C. (c 1.2, CH3OH); ir: 3610, 3440, 1110 and 1090 cm-1; 1H nmr d: 0.84 (s), 1.04 (s), 1.08 (s), 1.09 (d, J=6.8 Hz), and 1.16 (s) (15H, 5 CH3), 1.52 (d, J=14.1 Hz, 1H, H-7ax), 1.58 (dd, J=13.4, 13.2 Hz, 1H, H-11ax), 1.83 (dd, J=13.4, 3.7, 2.9 Hz, 1H, H-11eq), 1.87 (m, J=1 Hz, 3H, vinyl CH3), 2.11 (dd. J=14.1, 2.8 Hz, 1H, H-7eq), 2.13–2.22 (m, 1H, CHCH3), 3.35–3.41 (m, 2H, 2 equatorial H at C2 and C4), 3.58 and 3.54 (2d, J=11.9 and 12.6 Hz, respectively, 2H, 2 axial H at C2 and C4), 4.29 (d, J=6.2 Hz, 2H, CH2OH), 5.84 (ddq, J=6.7, 6.7, 6.7, 1.5 Hz, 1H, =CH); hrms (M+-18 peak): calc. for C20H30O3 318.2195, found 318.2188.

EXAMPLE 20

(−)-9(1E, 3Z)-(9S,10R)-9-(5-Hydroxy-3-methyl-1,3-pentadienyl)-3,3,8,8,10-pentamethyl-1,5-dioxaspiro[5,5]-undecan-9-ol (16)

(−)-(9Z)-(9R,10R)-9-(5-Hydroxy-3-methylpent-3-en-1-ynyl)-3,3,8,8,10-pentamethyl-1,5-dioxaspiro[5,5]-undecan-9-ol (149 mg, 0.44 mmol) was reduced with sodium bis(2-methoxyethoxy)aluminium hydride (RedalR, Aldrich, 3.4M in toluene, 0.8 mL, 2.48 mmol) by the procedure described in Example 14. The crude product obtained was usually hydrolyzed to give the ketodiol without purification. A small amount of the crude product was purified on the Chromatotron™ (75% ether+25% hexane) to give the desired ketal as a colorless oil, ir: 3600, 1600, 1100, 975, 910 cm-1; 1H nmr d: 0.76 (d, J=6.9 Hz), 0.83(s), 0.84 (s), 1.02 (s) and 1.06 (s) (15H, 5 CH3), 1.57 (d, J=14.1 Hz, 1H, H-7ax), 1.59 (dd, J=13.0, 12.7 Hz, 1H, H-11ax), 1.84 (ddd, J=12.7, 3.6, 2.7 Hz, 1H, H-11eq), 1.85 (d, J=0.9 Hz, 3H, vinyl CH3), 2.08 (dd, J=14.1, 2.7 Hz, 1H, H-7eq), 2.16 (ddq, J=13.0, 3.6, 6.8 Hz, 1H, CHCH3), 3.30–3.50 m, 2H, 2 equatorial H at C2 and C4), 3.56 and 3.60 (2d, J=11.7, 11.5 Hz, respectively, 2H, 2 axial H at C2 and C4), 4.30 (d, J= 7.0 Hz, 2H, CH2OH), 5.54 (dd, J=7.0, 6.8 Hz, 1H, =CH), 5.70 (d, J=15.8 Hz, 1H, =CH), 6.60 (d, J=15.8 Hz, 1H, =CH).

EXAMPLE 21

(−)-4(1E, 3Z)-(4S,5R)-4-Hydroxy-4-(5-hydroxy-3-methyl-1,3-pentadienyl)-3,3,5-trimethylcyclohexanone (17)

The crude ketal obtained in the procedure described in Example 20 was hydrolyzed by stirring with 1M HCl (4 drops) and acetone (5 mL) at room temperature for 1 h. Working up in the usual manner followed by purification on the Chromatotron™ (4 mm silica gel plate, 90% ether+10% hexane) gave the desired compound as a colorless oil (33 mg, 30% overall), [a]D −18.3° C. (c 1.1, CH3OH); ir: 3620, 1700 cm-1; 1H nmr d: 0.86 (d, J=6.5 Hz, CHCH3), 0.88 and 0.93 (2s, 6H, CH3), 1.86 (d, J=1.1 Hz, 3H, vinyl CH3), 1.90 (dd, J=13.6, 2.2 Hz, 1H, H-2eq), 2.18 (ddd, J=13.5, 4.3, 2.2 Hz, 1H, H-6eq), 2.23–2.33 (m, 1H, CHCH3), 2.41 (t, J=13.5 Hz, 1H, H-6ax), 2.82 (d, J=13.6 Hz, H-2ax), 4.31 (m, 2H, CH2OH), 5.59 (dd, J=7.0, 6.3 Hz, 1H, =CH), 5.73 (d, J=15.7 Hz, 1H, =CH), 6.69 (d, J=15.7 Hz, 1H, =CH);

13C nmr d: 16.03, 20.72, 24.51 and 24.59 (4q, CH3), 36.83 (d, CH), 42.85 (s, C3), 45.11, 51.46 and 58.34 (3t, 3 CH2), 77.78 (s, COH), 126.70, 128.28 and 134.01 (3d, 3 =CH), 134.51 (s, =C), 211.45 (s, C=O); hrms: calc. for C15H2403 252.1725, found 252.1708.

EXAMPLE 22

(−)-4(1E,3Z)-(4S, 5R)-4-Hydroxy-4-(5-oxo-3-methyl-1,3-pentadienyl)-3,3,5-trimethylcyclohexanone (18)

The ketodiol 17 (30 mg, 0.11 mmol) was oxidized with manganese oxide (420 mg, 4.8 mmol) to give the corresponding aldehyde by the procedure described in Example 17. The crude aldehyde was usually oxidized to ester as described in Example 23 without purification.

A small amount of the aldehyde 18 was purified by preparative tlc (90% ether+10% hexane) to give a colorless oil, [a]D −39.5 (c 0.77, CH3OH); ir: 3610, 3450, 1700 and 1665 cm-1; 1H nmr d: 0.89 (d, J=6.4 Hz, 3H, CHCH3), 0.96 (s, 6H, 2CH3), 1.93 (dd, J=13.6, 2.2 Hz, H-2eq), 2.08 (d, J=1.1 Hz, 3H, vinyl CH3), 2.20–2.46 (m, CH2 at C6 and CHCH3), 2.84 (d, J=13.6 Hz, 1H, H-2ax), 5.90 (d, J=7.8 Hz, 1H, =CH), 6.16 (dd, J=15.47, 0.4 Hz, 1H, =CH), 7.40 (d, J=15.7 Hz, 1H, =CH), 10.20 (d, J=7.8 Hz, 1H, CH=O).

EXAMPLE 23

(−)-(4S, 5R)-2',4'-Methyl dihydroabscisate (19)

Crude (−)-4(1E, 3Z)-(4S, 5R)-4-Hydroxy-4-(5-oxo-3-methyl-1,3-pentadienyl)-3,3,5-trimethylcyclohexanone (about 0.11 mmol) obtained from the procedure described in Example 22 was reacted with a mixture of methanol (5 mL), manganese oxide (310 mg, 3.56 mmol), sodium cyanide (35 mg, 0.71 mmol) and glacial acetic acid (35 mg, 0.58 mmol). The desired product (−)-(4S, 5R)-methyl dihydroabscisate was obtained as colorless crystals (21 mg, 70% overall yield). Part of the product was recrystallized from ether-hexane at 0° C. to give colorless plates, mp 105°–108° C.; [a]D −40.6° C. (c 1.03, CH3OH); ir: 1700 cm-1; 1H nmr d: 0.87 (d, J=6.5 Hz, 3H, CHCH3), 0.94 and 0.96 (2s, 6H, 2 CH3), 1.91 (dd, J=13.6, 2.2 Hz, 1H, H-2eq), 2.01 (d, J=1.2 Hz, 3H, vinyl CH3), 2.20 (ddd, J=13.6, 4.2, 2.2 Hz, H-6eq), 2.33 (m, 1H, CHCH3), 2.44 (dd, J=13.6, 13.0 Hz, 1H, H-6ax), 2.86 (d, J=13.6 Hz, 1H, H-2ax), 3.70 (s, 3H, OCH3), 5.72 (s, 1H, =CH), 6.09 (d, J=15.9 Hz, 1H, =CH), 7.81 (d, J=15.9 Hz, 1H, =CH); eims m/z: 280 (M+, 4), 192 (43), 164 (24), 123 (100); hrms: calc. for C16H2404 280.1675, found 280.1649.

EXAMPLE 24

(−)-(4S, 5R)-2',3'-dihydroabscisic acid (20)

(−)-(4S, 5R)-Methyl dihydroabscisate (15 mg, 0.05 mmol) was hydrolysed with 2M KOH (3 mL) and methanol (3 mL) to give (−)-(4S,5R)-dihydro-abscisic acid as a colorless oil (13 mg, 90%), [a]D −34.50 (c 0.89, CH3OH); ir: 2800–3500, 1680 cm-1; 1H nmr d: 088 (d, J=6.4 Hz, CHCH3), 0.95 and 0.96 (2S, 6H, 2 CH3), 1.91 (dd, J=13.6, 2.1 Hz, 1H, H-2eq), 2.04 (d, J=1.2 Hz, 3H, vinyl CH3), 2.21 (ddd, J=13.4, 4.1, 2.1 Hz, H-6eq), 2.35 (m, 1H, CHCH3), 2.44 (dd, J=13.4, 12.7 Hz, 1H, H-6ax), 2.86 (d, J=13.6 Hz, 1H, H-2ax), 5.75 (s, 1H, =CH), 6.14 and 7.79 (2d, J=16.1 Hz, 2H, 2 =CH); 13C nmr: 16.05, 21.48, 24.58 and 24.63 (4 CH3), 43.00 (C3), 36.67, 45.03 and 51.42 (CH and 2 CH2), 78.00 (COH), 151.77, 140.60, 127.72 and 116.99 (4 =C), 170.63 (COOH), 211.26 (C=O); eims m/z: 266 (M+, about 2), 248 (5), 192 (29), 164 (67), 123 (100 ); hrms: calc. for C15H2204 266.1518, found 266.1519.

EXAMPLE 25

(+)-(4R, 6S)-4-Hydroxy-2,2,6-trimethylcyclohexanone (21)

A mixture of (−)-(4R,6R)-4-hydroxy-2,2,6-trimethyl-cyclohexanone (300 mg, 0.19 mmol), 5M NaOH (1 mL) and ethanol (10 mL) was heated to 85° C. for 24 hrs under an argon atmosphere. Then most of the ethanol was removed by evaporation. The residue was dissolved in ether, and the solution was washed with water. After drying over anhydrous Na2SO4 and evaporation of the solvent, a pale yellow oil (255 mg) was obtained. Purification by flash chromatography (75% ether+25% hexane )gave unreacted trans ketol (46 mg), [a]D −102.3° C. (c 0.92, CH3OH), followed by the desired cis ketol as a colorless oil (195 mg, 73% based on starting material consumed). The product solidified on storage at −10° C. and was recrystallized from ether-hexane to give colorless needles, mp 48.0°–50.0° C. {lit. (13) mp 52°–53° C.}; [a]D +95.0° C. (c 0.88, CH3OH) {lit. (13) [a]D +107.4° C. (c 0.8, CH3OH)}; 1H nmr d: 0.96 (d, J=6.5 Hz, 3H, CHCH3), 1.00 and 1.14 (2s, 3H each, 2 CH3), 1.35 (ddd, J=12.4, 12.4, 11.3 Hz, 1H, H-5ax), 1.53 (dd, J=12.2, 11.5 Hz, 1H, H-3ax), 2.00 (ddd, J=12.2, 4.2, 3.5 Hz, H-3eq), 2.22 (m, 1H, H-5eq), 2.67 (m. 1H, H-6ax), 4.25 (tt, J=11.3, 4.3 Hz, 1H, H-4ax); eims m/z: 156 (M+, 10), 138 (8), 83 (66), 74 (50), 69 (60), 57 (100).

EXAMPLE 26

(+)-(4R,6S)-4-t, Butyldimethylsilyloxy-2,2,6-trimethyl-cyclo hexanone (22)

The cis ketol obtained in Example 25 (66 mg, 0.42 mmol) was treated with a mixture of t-butyldimethylsilyl chloride (130 mg, 0.86 mmol), imidazole (73 mg, 1.07 mmol) and dry DMF (2 mL). After working up and purification by distillation (kugel-rohr, 150°–180° C, 8–10 mm Hg), the desired silyl ether was obtained as a colorless oil (111 mg, 99%); [a]D +58.0° C. (c 0.98, CH3OH); ir: 1710 cm-1; 1H nmr d: 0.97 (s, 6H, CH3SiCH3), 0.87 (s, 9H, 3 CH3), 0.98 (d, J=6.5 Hz, 3H, CHCH3), 1.03 and 1.17 (2s, 3H each, 2 CH3), 1.43 (ddd, J=13.6, 12.8, 11.0 Hz, 1H, H-5ax), 1.58 (dd, J=13.1, 11.1 Hz, 1H, H-3ax), 1.89 (ddd, J=13.1, 4.3, 3.5 Hz, 1H, H-3eq), 2.11 (m, 1H, H-5eq), 2.68 (ddq, J=12.8, 6.5, 6.5 Hz, 1H, H-6ax), 4.24 (tt, J=11.0, 4.4 Hz, 1H, H-4ax); cims (isobutane) m/e: 271 (M++1); hrms: calc. for C15H3002Si 270.2015, found 270.2004.

EXAMPLE 27

(+)-1(Z)-(1R, 4R,6S)-4-t-Butyldimethylsilyloxy-1-(5-hydroxy-3-methylpent-3-en-1-ynyl)-2,2,6-trimethylcyclohexanol (23)

The ketosilyl ether from Example 26 (5.7 g, 21 mmol) was treated with Z-3-methylpent-2-en-4-yn-1-ol (3.0 g, 32 mmol) and n-butyllithium (1.6M in hexane, 40 mL, 63 mmol). The desired product was obtained as a colorless oil (4.9 g, 64%) which solidified on storage at 0° C. to give colorless crystals, gc (DB1701 column, 70°–240° C. at 10° C. min-1) retention time 19.11 min.; mp 89°–94° C.; [a]D +19.1° C. (c 0.82, CH3OH); ir: 3620 cm-1; 1H nmr d: 0.03 (s, 6H, CH3SiCH3), 0.86 (s, 9H, 3 CH3), 1.01 (s, 3H, CH3), 1.05 (d, J=6.5 Hz, 3H, CHCH3), 1.11 (s, 3H, CH3), 1.40, 1.55 and 1.73 (3m, 2 CH2), 1.89 (d, J=1.0 Hz, 3H, vinyl CH3), 1.92-2.00 (m, 1H, CHCH3), 3.83 (tt, J=10.8, 5.2 Hz, 1H, CHOSi), 4.32 (m, 2H, CH2OH), 5.86 (ddd, J=6.7, 6.7, 1.5 Hz, 1H, =CH); cims (isobutane) m/e: 367 (M++1), 349.

EXAMPLE 28

(+)-1(Z)-(1R,4R, 6S)-1-(5-Acetoxy-3-methylpent-3-en-1-ynyl)-2,2,6-trimethylcyclohexan-1,4-diol (24)

The dihydroxysilyl ether described in Example 27 (2.5 g, 6.9 mmol) was reacted with acetic anhydride (2.5 g, 18.6 mmol), pyridine (25 mL) and 4-dimethylaminopyridine (32 mg, 0.2 mmol) by the procedure previously described. A small amount of the crude acetate obtained was purified on the Chromatotron TM (1 mm silica gel plate, 50% ether+50% hexane) to give a colorless oil, gc (DB1701 column, 70°-240° C. at 10° C. min-1) retention time 19.37 min.; [a]D +17.6° C. (c 1.07, CH3OH); ir: 3610, 3500, 1725 cm-1; 1H nmr d: 0.03 (s, 6H, CH3SiCH3), 0.86 (s, 9H, 3 CH3), 1.01 (s, 3H, CH3), 1.05 (d, J=6.5 Hz, 3H, CHCH3), 1.11 (s, 3H, CH3), 1.37, 1.56 and 1.73 (3m, 2 CH2), 1.90 (d, J=1.3 Hz, 3H, vinyl CH3), 1.96 (m, 1H, CHCH3), 2.03 (s, 3H, CH3C=O), 3.84 (tt, J=11.0, 5.0 Hz, 1H, CHOSi), 4.74 (dd, J=7.1, 0.9 Hz, CH2O), 5.79 (dd, J=7.1, 7.1, 1.5 Hz, 1H, =CH); eims m/e: 348 (M+ −60); cims (isobutane) m/e: 409 (M++1), 349.

The crude acetate was desilated by heating (80° C.) with glacial acetic acid (30 mL) and water (10 mL) to give, after work up and purification, the desired product as a colorless oil (1.46 g, 73% overall yield), [a]D +23.8° C. (c 0.4, CH3OH); ir: 3610, 1735 cm-1; 1H nmr d: 1.03 (s, 3H, CH3), 1.06 (d, J=6.5 Hz, 3H, CHCH3), 1.12 (s, 3H, CH3), 1.37 and 1.57 (2m, H-3ax and CH2 at C5), 1.70 (ddd, J=12.7, 4.6, 2.3 Hz, 1H, H-3eq), 1.91 (d, J=1.3 Hz, vinyl CH3), 2.00 (m, 1H, CHCH3), 2.04 (s, 3H, CH3C=O), 3.84 (m, 1H, CHOH), 4.77 (d, J=7.3 Hz, CH2O), 5.70 (ddd, J=7.1, 7.1, 1.5 Hz, 1H, =CH); 13C nmr: 16.43, 20.73, 20.95, 23.17 and 26.96 (5 CH3), 39.92 (C2), 35.86, 41.76 and 46.38 (CH and 2 CH2), 62.89 and 66.10 (CHOH and CH2O), 78.31 (COH), 85.43 and 95.17 (2 acetylenic C), 123.68 (=C), 129.96 (=CH), 171.04 (C=O); eims m/e: 294 (M+, very weak), 234 (10), 148 (100).

EXAMPLE 29

(+)-4(Z)-(4R,5S)-4Hydroxy-4-(5-hydroxy-3-methylpent-3-en-1-ynyl)-3,3,5-trimethylcyclohexanone (25)

The dihydroxy acetate obtained in Example 28 (1.44 g, 4.9 mmol) was oxidized with pyridinium dichromate (6.07 g, 16.1 mmol) in CH2Cl2 (30 mL). A keto-acetate was obtained as colorless needles (0.94 g, 70%), mp 118.0°-120.0° C.; [a]D +20.5° C. (c 0.58, CH3OH); ir, 1H and 13C nmr identical with those of the (−)-enantiomer.

The keto-acetate (0.94 g, 3.2 mmol) was hydrolysed by stirring with 5M NaOH (1 mL) and methanol (25 mL) at room temperature for 1 h. After working up and purification, the desired product (+)-4(Z)-(4R,5S)-4-hydroxy-4-(5-hydroxy-3-methylpent-3-en-1ynyl)-3,3,5-trimethylcyclohexanone was obtained as colorless crystals (0.80 g, 100%, mp 96.5°-98.0° C.; [a]D +22.3° C. (c 0.53, CH3OH); ir, 1H and 13C nmr identical with those of the (−)-(4S, 5R) enantiomer.

EXAMPLE 30

(+)-9Z)-(9R,10S)-9-(5-Hydroxy-3-methylpent-3-en-1-ynyl)-3,3,8,8,10-pentamethyl-1,5-dioxaspiro[5,5]undecan-9-ol (26)

(+)-4(Z)-(4R,5S)-4-Hydroxy-4-(5-hydroxy-3-methylpent-3-en-1-ynyl)-3,3,5-trimethylcyclohexanone was treated with 2,2-dimethylpropane-1,3-diol in benzene with a catalytic amount of p-toluenesulfonic acid to afford the ketal, [a]D +27.1° C. (c 0.90, CH3OH).

EXAMPLE 31

(+)-9(1E, 3Z)-(9S,10S)-9-(5-Hydroxy-3-methyl-1,3-pentadienyl)-3,3,8,8,10-pentamethyl-1,5-dioxaspiro[5,5]-undecan-9-ol and (+)-4(1E,3Z)-(4S,5S)-4-Hydroxy-4-(5-hydroxy-3-methyl-1,3-pentadienyl)-3,3,5-trimethylcyclohexanone (27)

Reduction of (+)-(9Z)-(9R,10S)-9-(5-Hydroxy-3-methylpent-3-en-1-ynyl)-3,3,8,8,10-pentamethyl-1,5-dioxaspiro[5,5]undecan-9-ol with RedalR as described in Example 14 afforded the dienoic system and the product was hydrolyzed with 1M HCl and acetone as previously described to give the desired product ketone, [a]D +42.6° C. (c 1.03, CH3OH).

EXAMPLE 32

(+)-4-(1E,3Z)-(4S,5S)-4-Hydroxy-4-(5-oxo-3-methyl-1,3-pentadienyl)-3,3,5-trimethylcyclohexanone (29)

The aldehyde was prepared by the oxidation of (+)-4(12E,3Z)-(4S,5S)-4-Hydroxy-4-(5-hydroxy-3-methyl-1,3-pentadienyl)-3,3,5-trimethylcyclohexanone with manganese oxide and was further oxidized to (+)-(4S, 5S)-methyl 2',3'-dihydroabscisate without purification.

EXAMPLE 33

(+)-(4S, 5S)-2',3'-Methyl dihydroabscisate (30)

The aldehyde obtained in Example 32 was reacted with MnO2, NaCN, methanol and glacial acetic acid according to the procedure previously described to give (+)-(4S, 5S)-methyl dihydroabscisate as colorless needles, mp 117.5°-118.5° C.; [a]D +65.7° C. (c 0.9, CH3OH); hplc (chiracel OD column, 10% isopropanol+90% hexane at 1.0 mL min-1) retention time 8.7 min.

EXAMPLE 34

(+)-(4S, 5S)-2',3'-Dihydroabscisic acid (31)

(+)-(4S, 5S)-methyl dihydroabscisate was hydrolyzed with 2M KOH and methanol to give (+)-(4S, 5S)-dihydroabsciscic acid as colorless crystals, 173°-180° C.; [a]D +63.5° C. (c 1.17, CH3OH).

EXAMPLE 35

(−)-(10R)-3,3,8,8,10-Pentamethyl-1,5-dioxaspiro[5,5]-undecan-9-one (32)

A mixture of (−)-(6R)-2,2,6-trimethyl-1,4-cyclohexandione (924 mg, 6.0 mmol), 2,2-dimethyl-1,3-propandiol (791 mg, 7.6 mmol), pyridinium p-tosylate (34 mg, 0.13 mmol), and benzene (15 mL) was heated to reflux under a Dean-Stark water separator for 4 h. The reaction mixture was allowed to cool to room temperature before it was washed with H2O, and dried over anhydrous Na2SO4. Evaporation of solvent gave a pale yellow oil (1.43 g) as the crude product, which was distilled using the Kugel-rohr apparatus (80°–100° C., 0.03 mm Hg) to give pure ketal as a colorless oil (1.31 g, 91%), [a]D −87.7° C. (c 1.10, CH3OH); ir: 1710 cm-1; 1H nmr d: 0.85 (s, 3H, CH3), 0.91 (d, J=6.6 Hz, 3H, CHCH3), 0.97 (s, 6H, 2CH3), 1.16 (s, 3H, CH3), 1.56 (dd, J=13.5, 13.5 Hz, H-11ax), 1.58 (d, J=14.2 Hz, H-7ax), 2.38 (ddd, J=13.5, 5.3, 3.8 Hz, 1H, H-11eq), 2.47 (dd, J=14.2, 3.8 Hz, 1H, H-7eq), 2.85 (m, 1H, CHCH3), 3.41 and 3.48 (2dd, J=11.4, 1.6 Hz, 2H, 2 equatorial H at C2 and C4), 3.53 and 3.61 (2d, J=11.4 Hz, 2H, 2 axial H at C2 and C4); ms m/e: 240 (M+, 0.58), 141 (27), 155 (98), 83 (27), 69 (100).

EXAMPLE 36

(−)-(9Z)-9S, 10R)-9-(5-Hydroxy-3-methylpent-3-en-1-ynyl)-3,3,8,8,10-pentamethyl-1,5-dioxaspiro[5,5]undecan-9-ol (33)

(−)-(10R)-3,3,8,8,10-Pentamethyl-1,5-dioxaspiro[5,-5]undecan-9-one (1.31 g, 5.5 mmol) was reacted with Z-3-methylpent-2-en-4-yn-1-ol (0.65 g, 6.7 mmol) and n-butyllithium (1.6M in hexane, 8 mL, 12.8 mmol) in dry THF. The crude product obtained (yellow oil, 2.6 g) was purified by flash column chromatography (75% ether+25% hexane) followed by distillation using the Kugel-rohr apparatus (about 250° C., 0.06 mm Hg) to give the product as a colorless oil (1.40 g, 77%), [a]D +30.0° C. (c 1.05, CH3OH); ir and 1H nmr identical to those reported above for its antipode.

EXAMPLE 37

(±)-Z-4-hydroxy-4-(5-oxo-3-methylpent-3-en-1-ynyl)-3,3,5-trimethylcyclohexone (34) (PBI-18)

To pyridinium dichromate (1.14 g, 3.75 mmol) in dry DMF (6mL), at 5°–10° C. was slowly added (±)-Z-4-hydroxy-4-(5-hydroxy-3-methylpent-3-en-1-ynyl)-3,3,5-trimethylcyclohexone (750 mg, 3.0 mol) in DMF (5 mL). The reaction was maintained at 5° C. for 2.5 h, and then water was added and the product extracted three times with ether. The combined ethereal phases were washed with water, then with saturated NaCl solution, then dried over Na2SO4 and the solvent evaporated to afford 570 mg of crude product which was crystallized from ether to give 410 mg (54%) aldehyde that gave m.p. 126°–127° C.; ir (CHCl3) 3600 strong, 2200 weak, 1710, 1670, 1600, 1100, 1060, and 1020 cm-1; 1H nmr: 1.01 and 1.22 (s, gem, CH3, 6H), 1.16 (d, J=5.8 Hz, CHCH3, 3H), 2.16 (d, J=1.5 Hz, =CCH3, 3H), 2.1–2.4 (m, 4H), 2.61 (d, J=14.4 Hz, H-2ax, 1H), 6.22 (dq, J=8.1, 1.5 Hz, =CH, 1H), and 10.03 (d, J=8.1 Hz, CHO, 1H).

EXAMPLE 38

(±)-E-4-hydroxy-4-(5-oxo-3-methylpent-3-en-1-ynyl)-3,3,5-trimethylcyclohexone (35) (PBI-19)

A mixture of (±)-E-4-hydroxy-4-hydroxy-4-(5-hydroxy-3-methylpent-3-en-1-ynyl)-3,3,5-trimethylcyclohexone (2.0 g, 8.0 mol), manganese dioxide (14 g, 160 mmol), and acetone (50 mL) were combined and stirred for 1.5 h. The mixture was filtered, the solvent removed by evaporation, and the residue chromatographed over silica eluting with 75% ether and 25% hexane to afford 1.17 g (±)-E-4-hydroxy-4-(5-oxo-3-methylpent-3-en-1-ynyl)-3,3,5-trimethylcyclohexone (58%, as an oil, that gave ir: 3600 (strong), 220 (weak), 1710, 1660, 900 cm-1; gc/eims; 248 (M+, 15%) 233 (9), 219 (19), 205 (16), 192 (42), 163 (95) and 121 (100); 1H nmr: 0.99 and 1.20 (s, gem CH3, 6H), 1.14 (d, J=5.9 Hz, HCCH3, 3H), 2.11 (dd, J=J=14.3, 2.3 Hz, H-2 eq, 1H), 2.18 (m, H-6eq, 1H), 2.3 (m, 2H), 2.32 (d, J=1.5 Hz, =CCH3, 3H), 2.60 (d, J=14.3 Hz, H-2-ax, 1H), 6.22 (dq, J=7.7, 1.5 Hz, =CH, 1H), and 10.03 (d, J=7.7 Hz, CHO, 1H).

EXAMPLE 39

Methyl 2-Z 5-(4-oxo-2,2,6-trimethylcyclohexan-1-ol)-3-methylpenten-4-ynoate (36) (PBI-41)

Z-4-hydroxy-4-(5-oxo-3-methylpent-3-en-1-ynyl)-3,3,5-trimethylcyclohexanone (34) 350 mg, 1.4 mmol) was treated with manganese dioxide (1.9 g, 22 mmol), sodium cyanide (165 mg, 3.4 mmol), acetic acid (80 uL, 1.4 mL) in methanol (15 mL). After 2 h the mixture was filtered, the solid washed with ether. The combined organic phases were washed twice with water, then saturated NaCl solution, dried over anhydrous Na2SO4, and the solvent removed at reduced pressure. The product 36 was obtained pure by chromatography over silica (Chromatotron, elution with 50% ether 50% hexane, as an oil that gave: ir (CHCl3) 3600 (weak), 1710 (strong) cm-1; 1H nmr: 0.99 and 1.23 (s, gem CH3, 6H), 1.16 (d, J=6.3 Hz, HCCH3, 3H), 2.06 (d, J=1.5 Hz, =CCH3, 3H), 2.1–2.6 (m, 4H), 2.86 (d, J=14.3 Hz, H-3ax, 1H), 3.67 (s, OCH3, 3H), and 6.02 (q, J=1.5 Hz, =CH, 1H); gc/eims m/z 278 (m+, 4), 247 (6), 219 (46) and 137 (100).

EXAMPLE 40

2-Z5-(4-oxo-2,2,6-trimethylcyclohexan-1-ol)-3-methylpenten-4-ynoic acid (37) (PBI-40)

The ester 36 was saponified as for compound 30 to afford the enynoic acid 37 in 83% yield. The product gave ir (CHCl3) 3600 (weak), 3300 (br,strong) and 1690 (strong) cm-1; 1H nmr d: 0.99 and 1.21 (s, gem CH3, 6H), 1.14 (d, J=6.2 Hz, HCCH3, 3H), 2.25–2.35 (m, 4H), 2.47 (d, J=14.1 Hz, H-3eq, 1H), 2.82 (d, J=14.1 Hz, H-3ax, 1H), and 6.03 (q, J=1.4 Hz, =CH, 1H).

EXAMPLE 41

Influence of Compositions Containing Abscisic Acid Related Compounds PBI-03 (I), PBI-07 (IV) and PBI-11 (VI) on the Enhancement of Germination of Cress Seeds The results of these experiments are set forth in FIG. 1. Seeds (100) of cress were placed on two layers of Whatman Number 1 filter paper placed in 100×15 mm petri dishes. To each petri dish was added 5 ml of a solution containing abscisic acid related compound PBI-03 (I), PBI-07 (IV) or PBI-11 (VI) in the concentration range of $10^{-4}$ to $10^{-9}$M. Each treatment was replicated a minimum of 3 times. The seeds were steeped in this solution at 25° C. in the dark. At either 4, 6 or 8 hours intervals, the number of seeds which germinated was determined. Germination was determined by the protrusion and elongation of the radical. Cress seeds provide an excellent model for the determination of analogs on germination, because they germinate very quickly (within 13 to 24 hours) and are responsive to abscisic acid.

The results of this experiment which are set forth in FIG. 1 show that agricultural compositions containing compounds PBI-03 (I), PBI-07 (IV) and PBI-11 (VI) abscisic acid promoted the germination of cress seeds.

EXAMPLE 42

Influence of a Composition Containing Abscisic Acid Related Compound PBI-11 (VI) on the Enhancement of Germination of Katepwa Wheat Seeds at Low Temperatures The effect of abscisic acid related compound PBI-11 (VI) on the emergence of Katepwa seedlings grown at 10° C. was evaluated. Seeds of Katepwa wheat were steeped in PBI-11 (VI) made to a concentration of $10^{-5}$ to $10^{-7}$M in distilled water. The seeds were steeped for 4 hours at 22° C. Then the seeds were dried at 35° C. to a moisture content of approximately 12 percent. The seeds were then planted in a soil mixture of 1 part soil, 1 part peat and 1 part vermiculite at a uniform depth of 3 cm. The seeds in the soil were then transferred to a ConViron Model E-15 controlled environment chamber maintained at 10° C., in the dark. The number of seeds which emerged was determined twice a day.

Figure 2:
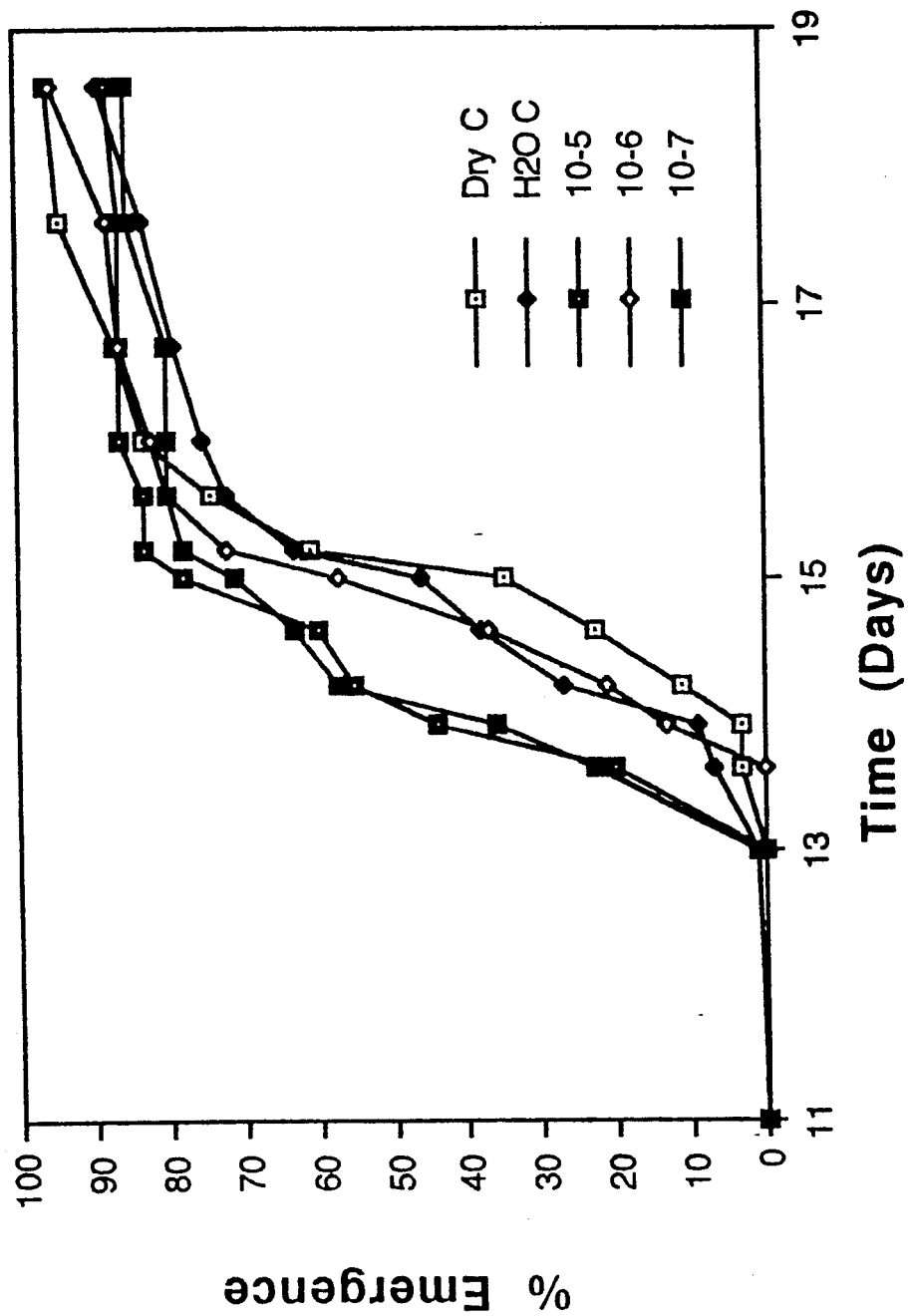
FIG. 2 represents the influence of abscisic acid analog PBI-11 on the enhancement of germination of Katepwa wheat seeds (Triticum aestivum).

The results of this experiment which are set forth in FIG. 2 demonstrate that PBI-11 (VI) at concentrations of $10^{-5}$ and $10^{-7}$M promoted the emergence of Katepwa wheat seedlings at 10° C. with respect to the water controls ($H_2O$ C).

EXAMPLE 43

Effects of Compositions Containing Compounds PBI-03 and PBI-10 on the Germination of Bluegrass Seeds

Methods

Approximately 200 seeds were placed om a petri plate containing filter paper and 3 ml of one concentration of 100, 10, 1, 0.1, 0.01 and 0.001 μM of Gibberellic Acid (GA) or ABA related compounds PBI-03 and PBI-10. Each compound (at100 μM) was dissolved in 1% acetone; lower concentrations were made by serial dilution with water. A Control treatment consisted of water + 1% acetone. Plates were sealed and covered with aluminum foil to exclude light from the plates. Plates were incubated at 17° C. and seeds were examined every 48 hours, from Day 7 to Day 35, for the emergence of coleoptiles (shoots) and roots form the seed. Seeds, which had germinated, were removed from the plate on each examination day.

Results

Figure 3:
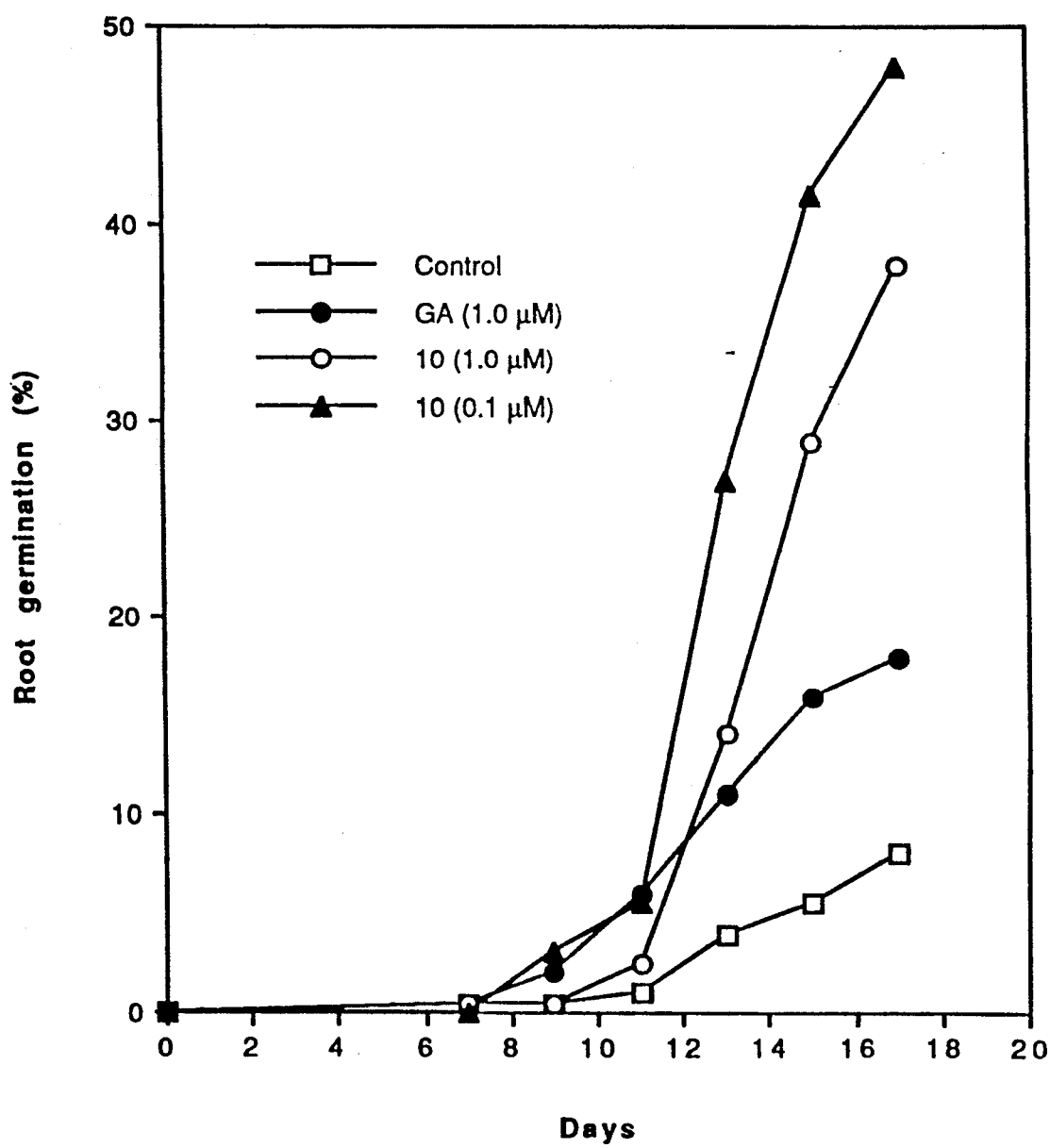
FIG. 3 represents the percentage of cumulative germination obtained by treatment of Kentucky Bluegrass (Poa pratensis) seeds with ABA related compounds PBI-03 and PBI-10.

At 17 days, the cumulative germination of GA-treated seeds was twice that of the Control seeds as shown in FIG. 3. GA is used for other recalcitrant seeds to overcome dormancy and/or promote germination by counteracting a light requirement. The results illustrated in FIG. 3 also demonstrate that seeds treatments of 0.01 μM PBI-03 has considerably higher germination that the Control as early as day 9. Also, it can be seen that the enhanced effect of PBI-10 was specific to the concentration.

EXAMPLE 44

Effect of Compositions Containing Compound PBI-10 on the Emergence of Canola at 10° C.

Methods

'Tobin' (7.3 g) and 7.4 g of 'Westar' canola were soaked for 8 hours at 25° C., in each of the following solutions: water; and one of 10, 1, or 0.1 μM PBI-10 in glass beakers. Beakers were sealed with aluminum foil to prevent evaporation and to exclude light. After incubation, solutions were removed and seeds were blotted dry with paper towels. Seeds were sandwiched between 4 layers of paper towels, which were daily changed and seeds were separated, and dried at 25° C., until their dried weight was close to their pre-soaking weight. About 100 seeds/treatment were sown, 2.5 cm deep in flats of 1:1:1 soil mix of peat, soil, and 'Vermiculite' in 4 rows 2.5 cm apart, and incubated at 10° C. in darkness. Flats were watered with cold tap water to saturation point, before incubation, and as needed. Flats were examined at daily intervals, until plants began emerging, and at 12 and 8 h. intervals as emergence progressed. The number of plants which had emerged in each interval were recorded. Results are shown in FIGS. 4 and 5 wherein 10-5, 10-6 and 10-7 respectively correspond to concentrations of 10 μM, 1 μM and 0.1 μM of PBI-10 in solution.

Results

Figure 4:
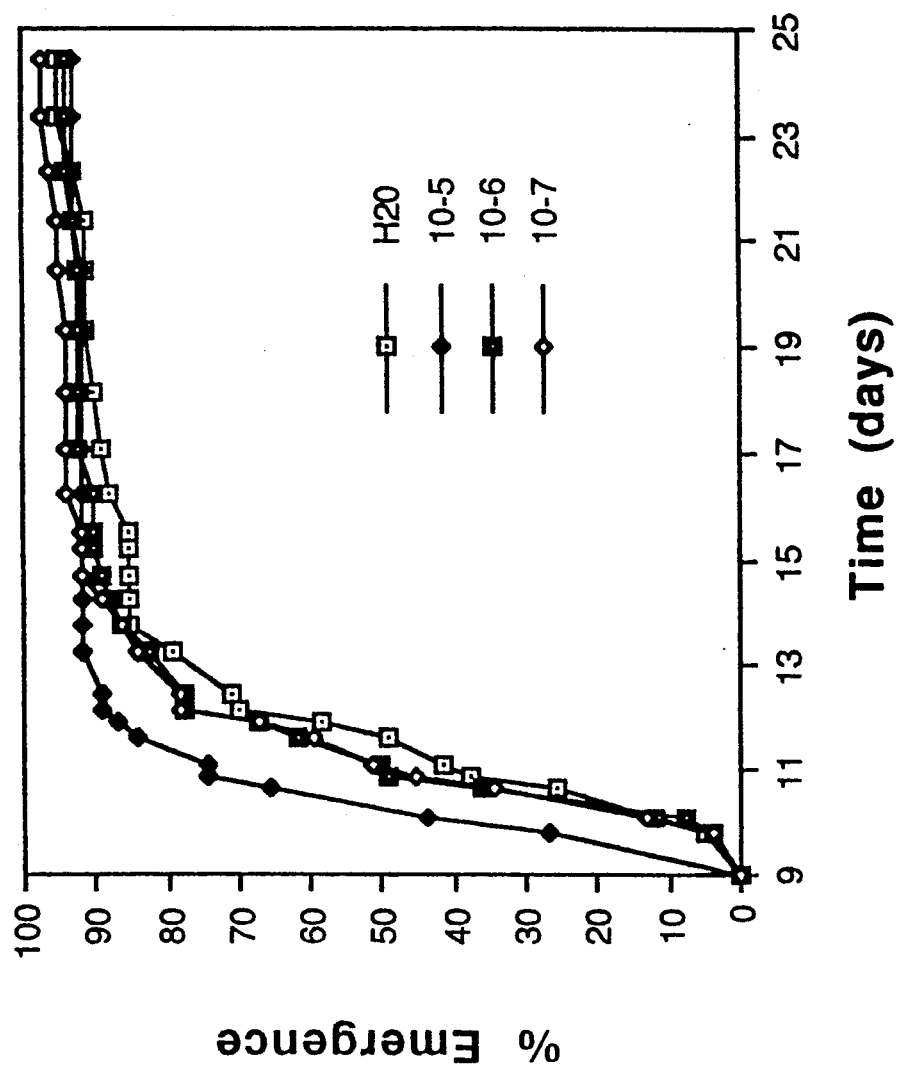
FIG. 4 represents the percentage of emergence of Canola obtained by treatment of Tobin Canola (Brassica campestris) seeds with ABA related compound PBI-10.
Figure 5:
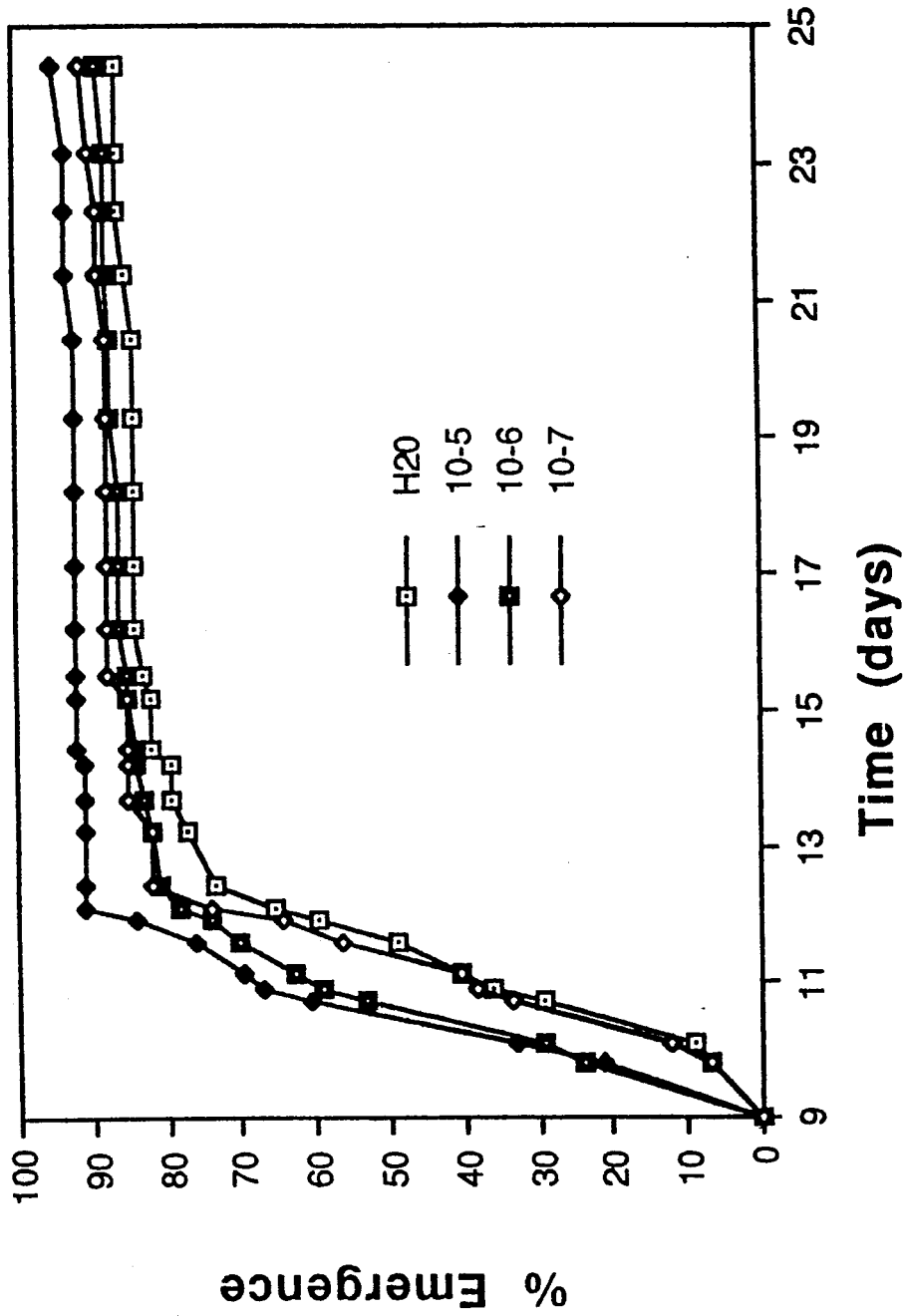
FIG. 5 represents the percentage of emergence of Canola obtained by treatment of Westar Canola seeds with ABA related compound PBI-10.

As shown in FIG. 4, 'Tobin' seedlings from 10 μM PBI-10 treated seed emerged at 10° C. more than a day earlier than those of the control (H2O). 'Westar' seedlings from the 10 and 1 μM PBI-10 treatments also emerged earlier than those of Water as shown in FIG. 5, 'Westar' seeds probably responded to the 1 μM solution and 'Tobin' did not, because 'Westar' seeds are larger and could imbibe more 1μM solution, and consequently reach a "treshhold level" to respond. Emergence of the seedlings was promoted by these seed treatments, even though the soil was wet and the temperature less than optimal.

EXAMPLE 45

Field Emergence of Canola and Wheat Seeds Treated with Compositions Containing Compounds PBI-03, PBI-07, PBI-10, PBI-11, PBI-19 and PBI-27.

Methods

Seeds of 'Westar' canola and 'Katepwa' Hard Red Spring wheat were soaked for 4 h. in 10, 1, and 0.1 μM solutions each of PBI-03, PBI-07, PBI-10, PBI-11, PBI-19, PBI-27, and ABA, and in water. Wheat seed (1500 g) was soaked in 2 liters of solution, while air was bubbled through the mix to agitate it and prevent anerobiosis; 50 g of canola seed was soaked in 100 ml of each solution and agitated on a rotary shaker. After soaking, solutions were removed and seeds were placed in cloth bags, and dried at room temperature with forced air for 24 h. Included in the field design of 22 treatments (3 concentrations of 7 compounds and a water Control), was a dry Control. Each treatment was replicated 6 times in a RCBD study. 'Katepwa' was sown Apr. 28, 1988 at Watrous, Saskatchewan, and 'Westar' was sown May 12, 1988 at Saskatoon, Saskatchewan. In each plot, 2-1 meter central rows were designated as count sites and the number of seedlings in each count site were recorded at 8 AM and at 4 PM, daily. Results are shown in FIGS. 6 and 7 wherein numerals −5, −6 and −7 respectively indicate concentrations of 10, 1 and 0.1 μM of either PBI-07 or PBI-10.

Results

When 'Westar' seeds were soaked in0.1 μM PBI-07 or in 1 μM PBI-10, their seedlings emerged earlier than seedlings from unsoaked seeds as shown in FIGS. 6 and 7 respectively. By the 8th day, the number of seedlings from water-soaked seeds were similiar to those from seeds soaked in 1 μM PBI-10. Hot, dry winds damaged or seared seedlings off as they emerged during most of the period of emergence.

More seedlings emerged on day 13 from the 0.1 μM PBI-19 seed-soaking from either the dry or the water-soaked seeds. Results are shown in Table 1. Also, the 0.1 μM PBI-19 seed-soaking produced more seedlings on day 14 than those from either the dry or the water-soaked treatments. Results are shown in Table 2. However, the number of plants in different Replicates were extremely variable.

On day 13, neither ABA, PBI-07, PBI-11, PBI-27 produced significantly more seedlings than either of the Controls according to Duncan's Multiple Range Test (Table 1). With the exception of PBI-07 and PBI-11, at least one concentration of all other compounds produced more seedlings than the Controls 1 day later (day 13-8 AM to day 14-4 PM) Table 2). The effects of compositions containing compounds PBI-03, PBI-10, PBI-19 and PBI-27 on emergence of Katepwa wheat with the dry Control (DRY-C) and the water Control (WET-C) are respectively illustrated in FIGS. 8 through 11. The numbers −5, −6 and −7 respectively represent concentrations of 10 μM, 1 μM and 0.1 μM.

TABLE 1

Average emergence and standard deviations (STD) of 'Katepwa' wheat at Watrous on Day 13 (8 AM, May 12), as affected by the seed treatments. The concentrations of compounds are, as follows: '−5' = 10 μM; '−6' = 1 μM; and '−7' = 0.1 μM

| TREATMENT | AVERAGE EMERGENCE | STD |
| --- | --- | --- |
| DRY CONTROL | 2.33 A* | 2.42 |
| WATER CONTROL | 2.83 A | 2.14 |
| ABA-6 | 3.33 A | 4.08 |
| PBI-10-7 | 3.33 A | 5.47 |
| PBI-07-5 | 7.00 AB | 8.90 |
| PBI-27-7 | 7.33 AB | 8.60 |
| PBI-11-5 | 7.83 AB | 7.14 |
| PBI-07-7 | 9.67 ABC | 8.04 |
| PBI-11-6 | 10.17 ABC | 8.66 |
| PBI-27-5 | 10.17 ABC | 10.25 |
| PBI-27-6 | 10.50 ABC | 11.04 |
| PBI-07-6 | 12.67 ABC | 15.33 |
| PBI-11-7 | 13.17 ABC | 9.68 |
| PBI-03-7 | 13.67 ABC | 13.00 |
| ABA-5 | 14.50 ABC | 10.43 |
| PBI-10-5 | 15.67 ABC | 18.43 |
| PBI-03-5 | 16.50 ABC | 8.64 |
| ABA-7 | 16.50 ABC | 11.49 |
| PBI-19-6 | 17.33 ABC | 14.86 |
| PBI-03-6 | 20.00 BC | 18.23 |
| PBI-19-5 | 20.17 BC | 15.79 |
| PBI-10-6 | 21.67 BC | 13.25 |
| PBI-19-7 | 24.67 C | 22.09 |

*Means followed by the same letter are not significantly different by Duncan's Multiple Range Test (Alpha = 0.5, N = 6).

TABLE 2

Average emergence and Standard deviation (STD) of 'Katepwa' wheat at Watrous on day 14 (4 PM, May 13), as affected by the seed treatment. The concentrations of compounds are, as follows: '−5' = 10 μM; '−6' = 1 μM; and '−7= = 0.1 μM.

| TREATMENT | AVERAGE EMERGENCE | STD |
| --- | --- | --- |
| WATER CONTROL | 25.17 A* | 6.05 |
| DRY CONTROL | 28.67 AB | 11.86 |
| ABA-6 | 32.33 ABC | 19.04 |
| PBI-07-6 | 33.33 ABC | 30.94 |
| PBI-10-7 | 36.67 ABC | 24.34 |
| PBI-07-5 | 37.00 ABC | 19.80 |
| PBI-11-5 | 38.17 ABC | 13.21 |

TABLE 2-continued

Average emergence and Standard deviation (STD) of 'Katepwa' wheat at Watrous on day 14 (4 PM, May 13), as affected by the seed treatment. The concentrations of compounds are, as follows: '−5' = 10 μM; '−6' = 1 μM; and '−7= = 0.1 μM.

| TREATMENT | AVERAGE EMERGENCE | STD |
| --- | --- | --- |
| PBI-07-7 | 43.50 ABC | 18.08 |
| PBI-27-6 | 47.00 ABCD | 18.07 |
| PBI-03-7 | 47.00 ABCD | 19.43 |
| ABA-7 | 47.50 ABCD | 22.55 |
| PBI-11-7 | 50.83 ABCD | 21.18 |
| PBI-11-6 | 50.83 ABCD | 26.23 |
| PBI-19-5 | 51.67 ABCD | 21.46 |
| PBI-27-5 | 51.83 ABCD | 13.91 |
| PBI-03-5 | 54.00 ABCD | 9.96 |
| PBI-19-6 | 54.50 BCD | 26.31 |
| PBI-10-6 | 55.33 BCD | 27.57 |
| PBI-27-7 | 56.33 BCD | 19.32 |
| ABA-5 | 57.67 BCD | 30.19 |
| PBI-10-5 | 59.33 CD | 19.46 |
| PBI-03-6 | 60.00 CD | 22.35 |
| PBI-19-7 | 73.67 D | 18.63 |

*Means followed by the same letter are not significantly different by Duncan's Multiple Range Test (Alpha = .05, N = 6).

EXAMPLE 46

Field Development of Corn and Duram Seeds and of Tomato Plants Treated with Various ABA Related Compounds a) Corn Methods Seeds were steeped for 4 hours (h.) with agitation in 10, 1, or 0.1 μM solutions of ABA, PBI-03, PBI-07, PBI-10, PBI-11, PBI-19, and PBI-27, and in water. Solutions were removed and seeds were dried for 24 h. with forced air at 20° to 25° C. Twelve grams (about 50 seeds) were sown 3 cm deep, 6 cm apart in 3.6 meter rows spaced 60 cm apart. Four replications of each treatment, including a DRY (no soak) Control, were sown on May 10, 1988. Plots were irrigated weekly, starting May 18. Haun values were recorded from 5 randomly selected plants in each plot of the study on May 28 and the data were analyzed. Characteristics of maturity, such as total plants, number of mature ears, and total ears, were recorded for all plots on Aug. 24, 1988. Data were transformed to mature ears/plant an total ears/plant. Data were analyzed.

Results

A 0.1 μM PBI-27 seed-soaking produced plants, which had 1.6 leaves more than the Dry Control plants as shown in Table 3. Also, all concentrations of PBI-03 produced plants which had at least 1 or more leaf than those of the Dry Control. Consequently, plants from these treatments were further ahead in their growth cycle than those of the Dry Control. The advancement of growth was evident, when plants form PBI-03 seed treatments had significantly more mature ears/plot and more mature ears/plant than those from Control seed treatments as can be seen in Table 4 and 5.

TABLE 3

Average Haun rating/plot of 'Sunnyvee' corn, sown May 10th, as affected by the seed treatments. Concentrations of compounds are denoted as follows: 1) 10 μM = '−5', 2) 1 μM = '−6', and 3) 0.1 μM = '−7'.

| TREATMENT | AVERAGE HAUN | | STD. DEV. |
|---|---|---|---|
| PBI-07-7 | 3.367 | A* | 1.502 |
| DRY CONTROL | 4.367 | B | 1.882 |
| PBI-10-7 | 4.440 | BC | 1.507 |
| PBI-07-6 | 4.515 | BCD | 1.918 |
| ABA-6 | 4.740 | BCDE | 1.285 |
| PBI-27-6 | 4.947 | BCDEF | 1.330 |
| PBI-10-5 | 5.013 | BCDEFG | 0.931 |
| PBI-11-5 | 5.033 | BCDEFG | 0.919 |
| WATER CONTROL | 5.047 | BCDEFG | 0.583 |
| PBI-19-6 | 5.107 | BCDEDGH | 0.776 |
| PBI-27-5 | 5.147 | BCDEFGH | 1.132 |
| ABA-7 | 5.220 | BCDEFGH | 0.658 |
| PBI-19-5 | 5.293 | BCDEFGH | 1.074 |
| PBI-11-7 | 5.373 | CDEFGH | 0.874 |
| PBI-19-7 | 5.373 | CDEFGH | 0.787 |
| PBI-03-7 | 5.413 | DEFGH | 1.023 |
| PBI-03-5 | 5.473 | EFGH | 0.869 |
| PBI-07-5 | 5.500 | EFGH | 0.605 |
| PBI-10-6 | 5.573 | EFGH | 0.757 |
| PBI-11-6 | 5.573 | EFGH | 0.665 |
| ABA-5 | 5.813 | FGH | 0.970 |
| PBI-03-6 | 5.940 | GH | 0.605 |
| PBI-27-7 | 6.020 | H | 0.661 |

*Means followed by the same letter are not significantly different by Duncan'Multiple Range Test (Alpha = .05, N = 15).

TABLE 4

Number of mature ears of corn, as affected by the compounds with which seed was treated.

| COMPOUND | MATURE EARS | | STANDARD DEV. |
|---|---|---|---|
| CONTROL | 13.452 | A* | 7.918 |
| PBI-07 | 14.375 | AB | 8.314 |
| PBI-10 | 15.208 | AB | 5.365 |
| ABA | 15.792 | ABC | 5.124 |
| PBI-27 | 17.417 | ABC | 5.664 |
| PBI-19 | 17.458 | ABC | 5.664 |
| PBI-11 | 18.083 | BC | 6.763 |
| PBI-03 | 19.542 | C | 2.934 |

*Means followed by the same letter are not significantly different by Duncan's Multiple Range Test (Alpha = .05, N = 24).

TABLE 5

Number of mature ears/plant (MEP) as affected by the compounds in the seed treatments.

| COMPOUND | MEP | | STANDARD DEV. |
|---|---|---|---|
| CONTROL | 0.728 | A* | 0.423 |
| PBI-07 | 0.825 | AB | 0.366 |
| PBI-10 | 0.850 | ABC | 0.283 |
| PBI-11 | 0.953 | BC | 0.215 |
| PBI-19 | 0.987 | BC | 0.304 |
| PBI-27 | 0.999 | BC | 0.327 |
| ABA | 1.013 | BC | 0.284 |
| PBI-03 | 1.039 | C | 0.184 |

*Means followed by the same letter are not significantly different by Duncan's Multiple Range Test (Alpha = .05, N = 24).

b) Durum

Methods

ABA, PBi-04, -05, -10, -11, -16, -17, -18, and PBI-19 were dissolved in 50 ml of methanol for an end equivalent of 10 μM when diluted with hexane at 1 volume methanol to 10 of hexane. Solutions were diluted to 1 and 0.1 μM concentrations with hexane. Seeds of 'Kyle' durum wheat were immersed in a hexane÷methanol solvent which was thereafter removed n less than 10 min under vacuum to volatilize the solvent while maintaining the active compound on the seed. Seeds were aired in a fume hood to remove any traces of hexane. Seeds (50 g) were packaged and sown at Scott, Saskatchewan. Each study consisted of 6 replications of each compound at each concentrations with 3 plots each of the solvent, a Dry control, and a Filler in each of 6 replications. Treatments were set out in a RCB-Design in 5 m² plots. After 40 days of growth, 10 randomly selected plants were dug from each plot in 3 randomly selected Replicates and Haun values were recorded for each plant. Data were analyzed.

Results

Haun values of 40 day-old duram plants from PBI-11 and PBI-16 seed treatments were significantly greater than those of the Controls (Table 6).

TABLE 6

Effect of the compounds in the seed treatment on the average Haun values, the Standard deviation (STD), and the coefficient of variability (CV) of 40 day-old 'Kyle' durum plants at Scott in 1989.

| COMPOUND | HAUN | | STD | CV |
|---|---|---|---|---|
| PBI-17 | 7.038 | A* | 0.887 | 0.126 |
| DRY CONTROL | 7.178 | AB | 0.720 | 0.100 |
| PBI-10 | 7.188 | AB | 0.794 | 0.110 |
| PBI-18 | 7.196 | AB | 1.061 | 0.147 |
| PBI-05 | 7.211 | AB | 1.004 | 0.139 |
| SOLVENT ONLY | 7.212 | AB | 0.896 | 0.124 |
| PBI-04 | 7.229 | AB | 0.845 | 0.117 |
| ABA | 7.422 | BC | 0.823 | 0.110 |
| PBI-19 | 7.459 | BC | 1.004 | 0.135 |
| PBI-11 | 7.510 | C | 0.667 | 0.088 |
| PBI-16 | 7.622 | C | 0.915 | 0.120 |

*Means followed by the same letter are not significantly different by Duncan's Multiple Range Test (Alpha = .05, N = 90).

c) Tomatoes—Days to Flower

Methods

'Manitoba' tomato plants were grown in 'Vermiculite'-filled individual plastic "mini-pots" in 8-plant trays. Ten and one μM solutions (<50 ml) of ABA, PBI-16, -18, -19, -34, -43, -37 and PBI-47 were placed in 27 by 28 cm plastic "Ziploc" freezer bags and the 8-plant trays of tomatoes were set in the solutions. A 0.1% acetone solution was used withi 2 trays (a solvent control) and 2 trays were not bagged, and were watered from overhead (no drench control). Approximately 16 hours later, transpiration rates (rate of evaporation of water from leaves =cm s$^{-1}$) were recorded with a "Licor" porometer. After transpiration rates were recorded, a side leaflet from the same leaf, as that from which a porometer reading was taken, was removed to determine the gm water/gm dry weight of leaves. After leaflets were removed, solutions in the bags were topped up to 150 ml. Plants were transplanted the following day and the day after transplanting, transpiration rates were recorded in the field. This experiment was repeated 1 week later. In Run #1, solutions in the bags were renewed after the first set of data were collected; in Run #2, solutions in the bags were brought to volume with 100 ml of water. Data of both Runs were analyzed together to compare methods. To determine when the first flower appeared, plants were examined daily from 18 days after transplanting.

Results

Tomato plants soil-drenched with PBI-37, prior to transplanting came into flower significantly sooner than plants, which had a drench with 0.1% acetone or no Drench at all (Table 7).

TABLE 7

The effect of compounds used in soil drench, prior to transplanting, on the number of days to flower after transplanting.

| COMPOUND | DAYS TO FLOWER | STD. DEV. |
|---|---|---|
| PBI-37 | 23.91 A* | 4.13 |
| PBI-19 | 26.69 B | 5.11 |
| SOLVENT | 26.72 B | 6.65 |
| PBI-16 | 26.97 B | 6.14 |
| PBI-47 | 27.97 B | 6.53 |
| NO DRENCH | 28.44 B | 7.17 |
| PBI-34 | 28.47 B | 4.76 |
| PBI-43 | 28.78 B | 4.55 |
| PBI-17 | 28.81 B | 4.76 |
| PBI-18 | 28.88 B | 4.98 |
| ABA | 28.91 B | 4.50 |

*Means followed by the same letter are not significantly different by Duncan's Multiple Range Test (N = 32, Alpha = .05).

EXAMPLE 47

Effect of Various ABA Related Compounds on the Transpiration Rate of Tomato Plants a) Growth Chamber Studies on Manitoba tomato plants.

Methods

'Manitoba' tomato plants were grown in "Econobloc" flats (80/flat), for 6 weeks in 'Vermiculite', at 25° C.±5° C., under fluorescent lights with a 16 hour photoperiod with an irradiance of 90 W m$^2$. Roots, which protruded from the bottom of the flat, were pruned off. Corks were placed in teh bottom of each well containing a plant. Ten ml of each of 10 and 1 μM solutions of PBI-33, PBI-34, PBI-05, PBI-11, PBI-31, PBI-37, PBI-38, PBI-53, PBI-54, PBI-34, PBI-15, PBI-18, PBI-01, PBI-39, PBI-41, PBI-57(ABA) and PBI-40 were placed in each of 8 plant wells. Although no synthesis process is specifically set forth for PBI-31, PBI-38, PBI-53 and PBI-54, those skilled in the art will appreciate that these compounds can be readily synthesized based on the information contained in the present application. Ten ml of 0.1% acetone were added to each of 16 plant wells as water controls. Transpiration rates (cm s$^{-1}$) were recorded and leaflet samples for moisture content of the leaves were collected on each of the 3 successive days. Plants were watered daily after data were collected. Theoretically, the concentrations of compounds in solution would become progressively weaker with each watering, so that the persistent effects of the compounds could be detected.

Results

As shown in FIG. 12, plants, drenched with PBI-41, had significantly lower cm s$^{-1}$ than those drenched with ABA, on each of the days in this study. A cm s$^{-1}$ value of 0.01 means that the stomata are completely closed; a value of 1.0 means that the stomata are completely open. The anti-transpiration effect of ABA was lost after the first day while the anti-transpiration effect of PBI-41 remained relatively constant throughout the study period. On day 2, the transpiration rate of the control approached that of PBI-41.

b) Transplant studies on Manitoba tomato plants

Methods

'Manitoba' tomato plants were grown in 'Vermiculite'-filled individual plastic "mini-pots" in 8-plant trays in the same environment as in the environment described in a). Ten and one μM solutions (150 ml) of ABA, PBI-16, -17, -18, -19, -34, -43, -37, and PBI-47 were placed in 27 by 28 cm plastic "Ziploc" freezer bags and the 8-plant trays of tomatoes were set in the solutions. A 0.1% acetone solution was used with 2 trays (a solvent control) and 2 trays were not bagged, and were watered from overhead (no drench control). Approximately 16 hours later, transpiration rates (cm s$^{-1}$) were recorded with a "Licor" porometer. After transpiration rates were recorded, a side leaflet was removed (as in a)), to determine the gm water/gm dry weight of leaves. After leaflets were removed, solutions in the bags were topped up to 150 ml. The next day, plants were transplanted to the field, and transpiration rates were recorded in the field the following day. This experiment was repeated 1 week later, with one change in procedure. After the first set of data were collected, the solutions in the bags were topped up to 150 ml with water. Transpiration data for before and after transplanting, and gm water/dry weight were analyzed, to compare effects of these two compounds.

Results

Even though the tomato plants were handled exactly the same prior to topping off the solutions in both Runs of this study, Table 8 shows that the average first transpiration rate of all treatments in Run #1 was significantly less than the average of treatments in Run #2. The gm water value of Run #1 was also significantly greater than that of Run #2 as demonstrated by Table 9. Plants in Run #1 were 7 days younger at the time of treatment than those in Run #2. After transplanting, none of the treatments had transpiration rates that were significantly less than those of the controls.

TABLE 8

Effects of the age (in weeks) of tomato plants, after 20 hours exposure to Analog soil drenches, on the first transpiration rates (cm s$^{-1}$ and Standard Deviation (STD) of their leaves.

| AGE (weeks) | CM S$^{-1}$ | STD |
|---|---|---|
| 7 (run #1) | 0.331 A* | 0.222 |
| 8 (run #2) | 0.431 B | 0.218 |

*Means are significantly different (Alpha = .001, N = 176).

TABLE 9

Effects of the age (in weeks) of tomato plants, after 20 hours exposure to Analog soil drench, on the gm water/gm dry weight (gm water) and Standard Deviation (STD) of leaflets.

| AGE (weeks) | GM WATER | STD |
|---|---|---|
| 7 (run #1) | 5.981 B | 1.05 |
| 8 (run #2) | 5.517 A* | 1.35 |

*Means are significantly different (Alpha = .001, N = 176).

c) Transplanting studies on Coldset tomato plants.

Methods

'Coldset' tomato plants were grown in 'Vermiculite'-filled individual plastic "mini-pots" in 8-plant trays in a greenhouse (Horticulture Dept.) for 5 weeks from late June to early August. Three days prior to the soil drench treatment, plants were moved outdoors to harden off. Solutions of ABA, PBI-04, PBI-05, PBI-10, PBI-11, PBI-32, PBI-31, PBI-42, PBI-46 and PBI-33 were used exactly like those in the previous section. Although no synthesis process is specifically set forth for PBI-31, PBI-32, PBI-42 and PBI-46, those skilled in the art will appreciate that these compounds can be radily synthesized based on the information contained in the present application. A water drench was used as 1 control treatment and normal overhead watering was used as the other control, while 10 and 1 μM solutions of each compound were used for the soil-drench treatments.

Plants were slightly wilted and the soil was relatively dry when 8-plant trays were immersed in plastic "Ziploc" bags, which each contained 200 ml of the drench solution. Bags were kept open to preent "cooking" in the hot sun. Plants of the "no-drench" treatment wee watered.

Sixteen hours later, transpiration rates (cm s$^{-1}$) were recorded (1 reading on each of the 8 plants/treatment). Soil-drench treatments were brought up to volume by the addition of 100 ml of the respective solutions. Plants were transplated (and watered in) to the field 24 hours (h) later and given a 1 h soaking with overhead irrigation. Transpiration rates (cm s$^{-1}$) were recorded for each 24 h later. As a measure of the stability of the plant under stress (transplanting), a ratio was formed of the 'after transplanting' transpiration rate divided by the 'before transplanting' transpiration rate. The transpiration data, 1) before transplanting, 2) the after transplanting, and 3) the ratio of after:before transplanting, were analyzed.

Results

The results set forth in Table 10 demonstrate that several compounds acted like ABA, in the reduction of the transpiration rate of the tomato leaves; transpiration rate values of these compounds were significantly lower than those of the controls. Including ABA, these compounds were PBI-04, PBI-05, PBI-11, and PBI-33. The results shown in Table 11 demonstrate that PBI-05 was equally effecitve at both 10 and 1 μM, as well as 10 μM PBI-04 and 1 μM ABA, to significantly lower than transpiration rate below those of the "no Drench" Control (Table 11). These compounds effectively counteracted the effect of the "water Drench", which almost doubled the transpiration rate of the "no drench" control.

TABLE 10

Transpiration rates (cm s$^{-1}$) of tomato leaves before transplanting, as affected by specific compounds of a preceding soil drench.

| COMPOUNDS | CM S$^{-1}$ | STD. DEV. |
|---|---|---|
| PBI-05 | 0.155 A* | 0.042 |
| ABA | 0.189 AB | 0.056 |
| PBI-11 | 0.204 AB | 0.082 |
| PBI-31 | 0.208 AB | 0.091 |
| PBI-04 | 0.209 AB | 0.075 |
| PBI-33 | 0.215 AB | 0.101 |
| PBI-10 | 0.309 BC | 0.049 |
| PBI-46 | 0.364 CD | 0.129 |
| CONTROLS | 0.373 CD | 0.178 |
| PBI-42 | 0.391 CD | 0.069 |
| PBI-32 | 0.453 D | 0.143 |

*Means followed by the same letter are not significantly different by Duncan's Multiple Range Test (Alpha = .01, N = 16).

TABLE 11

Transpiration rates (cm s1) of tomato leaves before transplanting, as affected by specific treatments.

| TREATMENT | CM S$^{-1}$ | STD. DEV. |
|---|---|---|
| PBI-31-5 | 0.129 A* | 0.042 |
| PBI-05-6 | 0.136 A | 0.044 |
| PBI-04-5 | 0.160 AB | 0.065 |
| ABA-6 | 0.170 ABC | 0.033 |

TABLE 11-continued

Transpiration rates (cm s1) of tomato leaves before transplanting, as affected by specific treatments.

| TREATMENT | CM S$^{-1}$ | STD. DEV. |
|---|---|---|
| PBI-05-5 | 0.174 ABC | 0.032 |
| PBI-11-5 | 0.183 ABCD | 0.053 |
| PBI-33-5 | 0.189 ABCDE | 0.084 |
| ABA-5 | 0.209 ABCDEF | 0.069 |
| PBI-11-6 | 0.225 ABCDEFG | 0.103 |
| PBI-33-6 | 0.241 BCDEFG | 0.116 |
| PBI-04-6 | 0.258 BCDEFG | 0.050 |
| PBI-46-5 | 0.269 CDEFG | 0.045 |
| NO-DRENCH | 0.279 DEFG | 0.081 |
| PBI-31-6 | 0.288 EFG | 0.042 |
| PBI-10-5 | 0.303 FGH | 0.051 |
| PBI-10-6 | 0.316 GHI | 0.044 |
| PBI-42-5 | 0.383 HIJ | 0.054 |
| PBI-32-5 | 0.391 HIJ | 0.097 |
| PBI-42-6 | 0.399 IJ | 0.084 |
| PBI-46-6 | 0.459 JK | 0.113 |
| WATER-DRENCH | 0.466 JK | 0.204 |
| PBI-32-6 | 0.514 K | 0.162 |

*Means followed by the same letter are not significantly different by Duncan's Multiple Range Test (Alpha = .05, N = 8).

EXAMPLE 48

Effect of ABA Related Compounds on Cold Hardiness of Bromegrass Cells.

Methods

Suspension cell cultures of bromegrass (*Bromus inermis* Leyss.) grown at 25° C., in darkness for 1 week in liquid Ericksson's medium containing 75 μM ABA were hardy to −40° C. This method was the Model, on each the cold hardiness tests of the compounds, were based. However, these compounds are organic and contain hydrophobic. components, which limit their solubility at high concentrations in water. The Tests were divided into 2 groups, as follows: 1) compounds were dissoled in water, and 2) compounds were dissolved in 1% dimethylsulfoxide (DMSO). Compounds in Group 1 were ABA, PBI-01, PBI-04, PBI-05, PBI-06, PBI-07, PBI-10, PBI-11, PBI-14 and PBI-15; compounds in Group 2 were ABA, PBI-16, PBI-17, PBI-18, PBI-19, PBI-34, PBI-43, PBI-37, and PBI-47. Compounds at the highest concentration (1000 or 100 μM) were serially diluted with water until at 0.01 μM concentration was reached. Five ml of each concentration was aseptically added to 45 ml of sterile liquid Erikssson's media (5 ml of 1000 μM 'X' in 45 ml media=100 μM of Compound 'X'). A control of Ericksson's media (Group 1) or Ericksson's media with and without 1% DMSO (Group 2) was used. Bromegrass cells (1 gram), aseptically added to each concentration and control(s), were incubated for 1 week at 25° C. in darkness on a rotary shaker at 150 rpm. Each treatment was repeated twice for Group 1 and 3 times for Group 2. After incubation, cells were removed and weighed to determine the growth of cells in each concentration. Cells were sampled for gm water/gm dry weight and for a Freeze Test to determine the lethal temperature for 50% (LT$_{50}$) of the cells. About 0.25 g of cells was used to determine the gm water/gm dry weight of cells; about 0.1 g of cells was put into each test tubes, noted as 3, −3, −5, −7, −9, −11, −14, −17, −20, −25, −30, −35, and −40° C. for each concentration of each compound plus the control. All tubes were sealed to prevent desiccation and held at −3° C., except the Controls which were held at 3° C. After 1 hour at −3° C., the cells were nucleated and held at −3° C. overnight. The temperature of the water bath was lowered at $-3°$ C. $h^{-1}$, until $-40°$ C. was reached. Tubes were removed at each of the temperatures and thawed at $3°$ C. overnight. Three ml of filtered, 0.08% 2,3,5-triphenyltetrazolium chloride (TTC), buffered with sodium phosphate to a pH of 7.5, was added to each test tube. Tubes were incubated for 24 h. at $25°$ C. in darkness. TTC was removed and 3 ml of 95% ethanol was added to extract the red pigment from the cells. Cells were incubated for 48 h. at $25°$ C. Approximately 2 ml of the liquid was removed from the cells and used in a 'Beckmann' spectrophotometer set at 486 nm to determine the abosrbance value for each sample. TTC forms the red pigment only with living cells, so a gradient curve of high to low absorbance values is formed. The $LT_{50}$ is that part of the curve where the absorbance value of the frozen treatment in less than one half the value of the unfrozen control.

Results

None of the compounds induced cells to $-30°$ C. as did 10 μM ABA, but PBI-04, PBI-05, PBI-34, and PBI-43 gave cells a lower $LT_{50}$ than ABA at concentrations as low as 0.01 μM as shown in Tables 12 and 13. The compounds induced categories of response. These categories were, as follows: 1) hardeners (lower $LT_{50}$ than the control); 2) same as the control; and 3) dehardeners (higher $LT_{50}$ than control). Tables 12 and 13 also show that each response was dependent on the concentration.

In Group 1, the categories were as follows: 1) the hardeners were 10 μM PBI-01, and all of both PBI-04 and PBI-05; 2) PBI-06, PBI-07, PBI-11, PBI-14, and PBI-15 were the same as control; and 3) the dehardeners were 0.1, 1, 10 and 100 μM PBI-10.

In Group 2, the categories were as follows: 1) the hardeners were 0.01 to 10 μM PBI-34 and all of PBI-43; 2) PBI-16 gave no response; and 3) the dehardeners were PBI-17, PBI-18, PBI-19, PBI-37, and PBI-47 (Table 13).

These categories were derived by consideration of the moisture content and growth rates, as well as the $LT_{50}$ of the cells. Compounds, which are hardeners tend to reduce the weight of cells during incubation and the gm water/gm dry weight of cells is lower than that of the control. Dehardeners often increase the weight of cells during incubation, but the moisutre content of the cells is always higher than that of the control.

TABLE 12

Effects of concentration and of compounds on the $LT_{50}$ (°C.) of bromegrass cells incubated in compounds dissolved in water (Group 1)

| COMPOUND | $LT_{50}$ (°C.) at each Concentration in μM | | | | | |
|---|---|---|---|---|---|---|
| | 0.001 | 0.01 | 0.1 | 1 | 10 | 100 |
| CONTROL | −10 | −10 | −10 | −10 | −10 | −10 |
| ABA | −10 | −10 | −10 | −15 | −25 | −35 |
| PBI-01[X] | −12.5 | −12.5 | −12.5 | −12.5 | −15.5 | |
| PBI-04[X] | −14 | −17 | −17 | −17 | −17 | −17 |
| PBI-05[X] | −15 | −15 | −15 | −20 | −20 | −20 |
| PBI-06 | −8 | −11 | −13 | −10 | −13 | |
| PBI-07 | −9 | −10 | −14 | −11 | −12.5 | |
| PBI-10* | −8 | −9 | −9 | −2 | −3 | −5 |
| PBI-11 | −9 | −11 | −10 | −12.5 | −12.5 | −14 |
| PBI-14 | −10 | −12.5 | −10 | −10 | −10 | |
| PBI-15 | −8 | −8 | −8 | −8 | −6 | |

[X]Hardener
*Dehardener.

TABLE 13

Effect of concentration and compound on the $LT_{50}$ (°C.) of bromegrass cells incubated in compounds which have been dissolved in 1% DMSO (Group 2).

| COMPOUND | $LT_{50}$ (°C.) at each Concentration in μM | | | | |
|---|---|---|---|---|---|
| | 0.001 | 0.01 | 0.1 | 1 | 10 |
| CONTROL | −12.5 | −12.5 | −12.5 | −12.5 | −12.5 |
| ABA | −12.5 | −12.5 | −13.5 | −17 | −30 |
| PBI-16[X] | −11.3 | −11.3 | −11.3 | −11.3 | −11.3 |
| PBI-17 | −8.3 | −8.3 | −9 | −9.3 | −4 |
| PBI-18 | −6.3 | −5 | −5 | −6.3 | −4 |
| PBI-19 | −7 | −4 | −3 | −5 | −6 |
| PBI-37 | 0 | 0 | 0 | 0 | −5 |
| PBI-47 | −3 | −2 | −5 | −6 | −4 |
| PBI-34* | −5 | −15.5 | −15.5 | −14.5 | −17 |
| PBI-43* | −17 | −20.5 | −15.5 | −15.5 | −17 |

[X]Same as control.
*Hardener.

We claim:
1. A method for enhancing germination and growth of plants which comprises treating plant parts used in propagation with a solution comprising an effective amount of a compound having the following general formula:

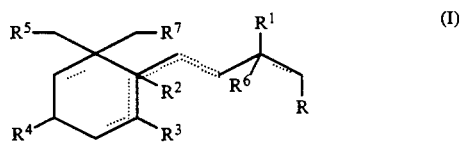

wherein

R is carboxyl, aldehyde, hydroxy, hydroxyloweralkyl, alkoxyloweralkyl, loweralkoxycarbonyl, loweracyloxyloweralkyl, acetylloweralkyl, loweralkanoyl, loweralkylamino, diloweralkylamino, loweralkoxy, loweracyloxy, loweralkylthio, loweralkyl sulphonyl, loweralkyl sulphinyl, amino, carbonyl, halogen, thio, phosphate, sulfoxide, sulfone or deuterium;

$R^1$ is loweralkyl hydrogen, oxo, hydroxyloweralkyl, loweralkoxy, halogen, thio, sulfoxide, sulfone, phosphate or deuterium;

$R^2$ may be hydrogen, oxo, hydroxy, halogen, thio, phosphate, sulfoxide, sulfone or deuterium;

$R^3$ is carboxyl, aldehyde, loweralkyl, hydroxyloweralkyl, alkoxyloweralkyl, loweralkoxycarbonyl, loweracyloxyloweralkyl, acetylloweralkyl, loweralkanyol, loweralkylamino, diloweralkylamino, loweralkoxy, loweracyloxy, loweralkythio, loweralkyl sulphonyl, loweralkyl sulphinyl, or carbonyl; and when $R^2$ is oxo or thio, $R^2$ maybe linked to both $C_1$ and $C_2$ carbon atoms to form an epoxy or a thioepoxy ring; $R^4$ is hydrogen, oxo, halogen, thio, phosphate, sulfoxide, sulfone, deuterium, hydroxy, loweralkylsiloxane, carboxyl, aldehyde, hydroxyloweralkyl, alkoxyloweralkyl, loweralkoxycarbonyl, loweracyloxyloweralkyl, acetylloweralkyl, loweralkanoyl, loweralkylamino, diloweralkylamino, loweralkoxy, loweracyloxy, loweralkylthio, loweralkyl sulphonyl, loweralkyl sulphinyl, amino, carbonyl, cycloalkyl or cycloalkoxy having from 4 to 6 carbon atoms which is optionally substituted by loweralkyl, halogen, oxygen, hydroxy or loweralkoxy;

$R^5$ is carboxyl, hydroxy, aldehyde, hydroxyloweralkyl, alkoxyloweralkyl, loweralkoxycarbonyl, loweracyloxyloweralkyl, acetylloeralkyl, acetoxyloweralkyl, loweralkanoyl, loweralkylamino, diloweralkylamino, loweralkoxy, loweracyloxy, loweralkylthio, loweralkyl sulphonyl, loweralkyl sulphinyl, amino, carbonyl, halogen, hydrogen oxo, thio, phosphate, sulfoxide, sulfone or deuterium, and when $R^5$ is oxo, it maybe linked to the carbon atom bearing $R^3$;

$R^6$ is hydrogen, oxo, hydroxyloweralkyl, loweralkoxy, halogen, thio, sulfoxide, sulfone, phosphate or deuterium;

$R^7$ may be carboxyl, hydroxy, aldehyde, hydroxyloweralkyl, alkoxyloweralkyl, loweralkoxycarbonyl, loweracyloxyloweralkyl, acetylloweralkyl, acetoxyloweralkyl, loweralkanoyl, loweralkylamino, diloweralkylamino, loweralkoxy, loweracyloxy, loweralkylthio, loweralkyl sulphonyl, loweralkyl sulphinyl, amino, carbonyl, halogen, hydrogen, oxo, thio, phosphate, sulfoxide, sulfone or deuterium, and when $R^7$ is oxo, it maybe linked to the carbon atom bearing $R^3$; and wherein the dotted lines may each represent a single bond and the double dotted line represents either a double bond or a triple bond, $R^1$ or $R^6$ is absent if the dotted line adjacent to $R^1$ and $R^6$ is a single bond, $R_2$ is absent if either of the dotted lines adjacent to $R_2$ is a single bond, the alkyl group bearing $R_7$ is absent if the dotted line adjacent to the alkyl group bearing $R_7$ is a single bond. and isomers and functional derivatives thereof, in admixture with an acceptable agricultural carrier comprising an agriculturally acceptable carrier cation when R, $R^1$, $R^2$, $R^4$, $R^5$, $R^6$ or $R^7$ are phosphate, sulfoxide or sulfone.

2. A method according to claim 1, wherein the plant parts to be treated are seeds.

3. A method according to claim 1, wherein the plants are selected from wheat, corn, flax, barley, cress and various grasses.

4. A method according to claim 3, wherein the plant parts to be treated are seeds.

5. The method of claim 1, wherein R is carboxyl, aldehyde, hydroxyloweralkyl, alkoxyloweralkyl, loweralkoxycarbonyl, loweracyloxyloweralkyl or acetylloweralkyl;

$R^1$ is loweralkyl;

$R^2$ is hydrogen, hydroxy or oxo and wherein the oxo group may be linked to both $C_1$ and $C_2$ carbons to form an epoxy group;

$R^3$ is loweralkyl;

$R^4$ is hydrogen, oxo, hydroxy or loweralkylsiloxane;

$R^5$ is hydrogen; and $R^6$ is hydroxy.

6. The method of claim 1, wherein said compound of formula I is selected from the group consisting of:

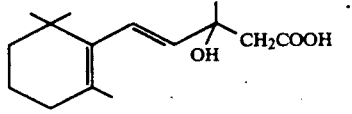
PBI-03

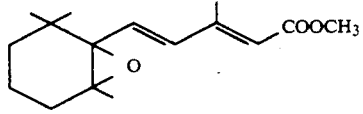
PBI-07

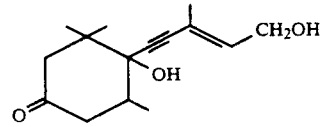
PBI-10 and

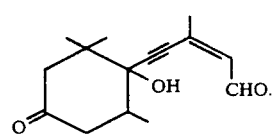
PBI-18

* * * * *